(12) United States Patent
Schmoll et al.

(10) Patent No.: US 12,396,640 B2
(45) Date of Patent: *Aug. 26, 2025

(54) FREQUENCY-DOMAIN INTERFEROMETRIC BASED IMAGING SYSTEMS AND METHODS

(71) Applicant: CARL ZEISS MEDITEC, INC., Dublin, CA (US)

(72) Inventors: Tilman Schmoll, Dublin, CA (US); Alexandre R. Tumlinson, San Leandro, CA (US); Matthew J. Everett, Livermore, CA (US); Nathan D. Shemonski, San Francisco, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/543,068

(22) Filed: Dec. 18, 2023

(65) Prior Publication Data
US 2024/0115128 A1 Apr. 11, 2024

Related U.S. Application Data

(60) Division of application No. 17/014,374, filed on Sep. 8, 2020, now Pat. No. 11,890,052, which is a
(Continued)

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0025* (2013.01); *A61B 3/0041* (2013.01);
(Continued)

(58) Field of Classification Search
CPC ........ A61B 3/00; G01B 9/00; G01N 21/4795; G02B 21/0056; G02B 27/0927
(Continued)

(56) References Cited

U.S. PATENT DOCUMENTS 5,815,242 A 9/1998 Anderson et al.
6,263,227 B1 7/2001 Boggett et al.
(Continued)

FOREIGN PATENT DOCUMENTS

EP 519105 B1 8/1995
EP 2271249 B1 3/2016
(Continued)

OTHER PUBLICATIONS

Abramoff et al., (2006). "Visual Stimulus-Induced Changes in Human Near-Infrared Fundus Reflectance", Investigative Ophthalmology & Visual Science, vol. 47, No. 2, pp. 715-721.
(Continued)

*Primary Examiner* — Wyatt A Stoffa
*Assistant Examiner* — Grant A Gagnon
(74) *Attorney, Agent, or Firm* — SNELL & WILMER L.L.P.

(57) ABSTRACT

Systems and methods for improved interferometric imaging are presented. One embodiment is a partial field frequency-domain interferometric imaging system in which a light beam is scanned in two directions across a sample and the light scattered from the object is collected using a spatially resolved detector. The light beam could illuminate a spot, a line or a two-dimensional area on the sample. Additional embodiments with applicability to partial field as well as other types of interferometric systems are also presented.

3 Claims, 12 Drawing Sheets

Related U.S. Application Data continuation of application No. 15/311,499, filed as application No. PCT/EP2015/062771 on Jun. 9, 2015, now Pat. No. 10,799,111.

(60) Provisional application No. 62/112,577, filed on Feb. 5, 2015, provisional application No. 62/031,619, filed on Jul. 31, 2014, provisional application No. 62/010,367, filed on Jun. 10, 2014.

(51) Int. Cl.

| | | |
|---|---|---|
| *A61B 3/12* | (2006.01) | |
| *A61B 3/15* | (2006.01) | |
| *G01B 9/02* | (2022.01) | |
| *G01B 9/02004* | (2022.01) | |
| *G01B 9/02015* | (2022.01) | |
| *G01B 9/02055* | (2022.01) | |
| *G01B 9/02091* | (2022.01) | |
| *G01B 9/02097* | (2022.01) | |
| *G01N 21/47* | (2006.01) | |
| *G02B 21/00* | (2006.01) | |
| *G02B 27/09* | (2006.01) | |
| *G01N 21/45* | (2006.01) | |

(52) U.S. Cl.
CPC .......... *A61B 3/0075* (2013.01); *A61B 3/1025* (2013.01); *A61B 3/1225* (2013.01); *A61B 3/152* (2013.01); *G01B 9/02004* (2013.01); *G01B 9/0203* (2013.01); *G01B 9/02032* (2013.01); *G01B 9/02043* (2013.01); *G01B 9/02044* (2013.01); *G01B 9/02072* (2013.04); *G01B 9/02077* (2013.01); *G01B 9/02085* (2013.01); *G01B 9/02091* (2013.01); *G01B 9/02097* (2013.01); *G01N 21/4795* (2013.01); *G02B 21/0056* (2013.01); *G02B 27/0927* (2013.01); *G01N 2021/458* (2013.01)

(58) Field of Classification Search
USPC .......................................................... 351/208
See application file for complete search history.

(56) References Cited

U.S. PATENT DOCUMENTS

| | | |
|---|---|---|
| 7,365,856 B2 | 4/2008 | Everett et al. |
| 7,602,501 B2 | 10/2009 | Ralston et al. |
| 7,643,155 B2 | 1/2010 | Marks et al. |
| 8,125,645 B2 | 2/2012 | Ozawa et al. |
| 8,480,579 B2 | 7/2013 | Serov et al. |
| 2005/0170572 A1 | 8/2005 | Hongo et al. |
| 2006/0164653 A1 | 7/2006 | Everett et al. |
| 2006/0244973 A1 | 11/2006 | Yun et al. |
| 2007/0091267 A1 | 4/2007 | Steinhuber |
| 2007/0291277 A1 | 12/2007 | Everett et al. |
| 2011/0267340 A1 | 11/2011 | Kraus et al. |
| 2012/0069303 A1 | 3/2012 | Seesselberg et al. |
| 2012/0261583 A1 | 10/2012 | Watson et al. |
| 2012/0274897 A1 | 11/2012 | Narasimha-Iyer et al. |
| 2012/0307035 A1 | 12/2012 | Yaqoob et al. |
| 2013/0010260 A1 | 1/2013 | Tumlinson et al. |
| 2013/0093997 A1 | 4/2013 | Utsunomiya et al. |
| 2013/0301000 A1 | 11/2013 | Sharma et al. |
| 2014/0028974 A1 | 1/2014 | Tumlinson |
| 2014/0050382 A1 | 2/2014 | Adie et al. |
| 2014/0063450 A1 | 3/2014 | Sternal et al. |
| 2014/0104569 A1 | 4/2014 | Yamazaki |
| 2014/0218684 A1 | 8/2014 | Carl et al. |
| 2015/0092195 A1 | 4/2015 | Leitgeb et al. |
| 2015/0233700 A1 | 8/2015 | Everett et al. |

FOREIGN PATENT DOCUMENTS

| | | |
|---|---|---|
| GB | 2413022 A | 10/2005 |
| JP | 2001523334 A | 11/2001 |
| JP | 2005217213 A | 8/2005 |
| JP | 2005530128 A | 10/2005 |
| JP | 2006116028 A | 5/2006 |
| JP | 2007105479 A | 4/2007 |
| JP | 2012010960 A | 1/2012 |
| JP | 2012502674 A | 2/2012 |
| JP | 2013085758 A | 5/2013 |
| JP | 2013525035 A | 6/2013 |
| JP | 2014048126 A | 3/2014 |
| JP | 2014079464 A | 5/2014 |
| JP | 2014094313 A | 5/2014 |
| WO | WO-1998043042 A1 | 10/1998 |
| WO | WO-2003060423 A2 | 7/2003 |
| WO | WO-2003063677 A1 | 8/2003 |
| WO | WO-2011139895 A1 | 11/2011 |
| WO | WO-2012143113 A1 | 10/2012 |
| WO | WO-2014140256 A2 | 9/2014 |
| WO | WO-2014179465 A1 | 11/2014 |
| WO | WO-2015024663 A1 | 2/2015 |
| WO | WO-2015052071 A1 | 4/2015 |
| WO | WO 2015189174 | 12/2015 |

OTHER PUBLICATIONS

Adie et al., (2012). "Computational Adaptive Optics for Broadband Optical Interferometric Tomography of Biological Tissue", PNAS, vol. 109, No. 19, pp. 7175-7180.

Adie et al., (2012). "Guide-Star-based Computational Adaptive Optics for Broadband Interferometric Tomography", Applied Physics Letters, vol. 101, pp. 221117-1-221117-5.

Aganj et al., (2012). "A 3D Wavelet Fusion Approach for the Reconstruction of Isotropic-Resolution MR Images from Orthogonal Anisotropic-Resolution Scans", Magn Reson Med., vol. 67, No. 4, pp. 1167-1172.

Beverage et al., (2002). "Measurement of the Three-Dimensional Microscope Point Spread Function Using A Shack-Hartmann Wavefront Sensor", Journal of Microscopy, vol. 205, pp. 61-75.

Bizheva et al., (2006). "Optophysiology: Depth-Resolved Probing of Retinal Physiology with functional Ultrahigh-Resolution Optical Coherence Tomography", PNAS, vol. 103, No. 13, pp. 5066-5071.

Blatter et al., (2013). "Angle Independent Flow Assessment with Bidirectional Doppler Optical Coherence Tomography", Optics Letters, vol. 38, No. 21, pp. 4433-4436.

Blazkiewicz et al., (2005). "Signal-to-Noise Ratio Study of Full-Field Fourier-Domain Optical Coherence Tomography", Applied Optics, vol. 44, No. 36, pp. 7722-7729.

Boccara et al., (2013). "Full-Field Oct: A Non-Invasive Tool for Diagnosis and Tissue Selection", SPIE Newsroom, 4 pages.

Bonesi et al., (2014). "Akinetic All-Semiconductor Programmable Swept-Source At 1550 nm and 1310 nm With Centimeters Coherence Length", Optics Express, vol. 22, No. 3, pp. 2632-2655.

Bonin et al., (2010). "In Vivo Fourier-Domain Full-Field OCT of the Human Retina with 1.5 Million A-lines/s", Optics Letters, vol. 35, No. 20, pp. 3432-3434.

Choma et al., (2003). "Sensitivity Advantage of Swept Source and Fourier Domain Optical Coherence Tomography", Optics Express, vol. 11, No. 18, pp. 2183-2189.

Choma et al., (2005) "Spectral-Domain Phase Microscopy", Optics Letters, vol. 30, No. 10, pp. 1162-1164.

Colomb et al., (2006). "Numerical Parametric Lens for Shifting, Magnification, and Complete Aberration Compensation in Digital Holographic Microscopy", J. Opt. Soc. Am. A, vol. 23, No. 12, pp. 3177-3190.

Coquoz et al., (1993)."Performance of on-Axis Holography with a Flexible Endoscope", SPIE, vol. 1889, pp. 216-223.

Coquoz et al., (1994). "Microendoscopic Holography with Flexible Fiber Bundle: Experimental Approach", SPIE, vol. 2083, pp. 314-318.

(56) References Cited

OTHER PUBLICATIONS

Cuche et al., (2000). "Spatial Filtering for Zero-Order and Twin-Image Elimination in Digital Off-Axis Holography", Applied Optics, vol. 39, No. 23, pp. 4070-4075.
Cui et al., (2017). "Multifiber Angular Compounding Optical Coherence Tomography for Speckle Reduction", Optics Letters, vol. 42, No. 1, pp. 125-128.
Dan, (2013). "DMD-based LED-Illumination Super-Resolution and Optical Sectioning Microscopy", Scientific Reports, vol. 3, No. 1116, pp. 1-7.
Endo et al., (2005). "Profilometry with Line-Field Fourier-Domain Interferometry", Optics Express, vol. 13, No. 3, pp. 695-701.
Everett et al., (1998). "Birefringence Characterization of Biological Tissue by use of Optical Coherence Tomography", Optics Letters, vol. 23, No. 3, pp. 228-230.
Fechtig et al., (2015). "Line-Field Parallel Swept Source MHz OCT for Structural and Functional Retinal Imaging", Biomedical Optics Express, vol. 6, No. 3, pp. 716-735.
Fercher et al., (1988). "Eye-length Measurement by Interferometry with Partially Coherent Light", Optics Letters, Optical Society of America, vol. 13, No. 3, pp. 186-188.
Fercher et al., (1995). "Measurement of Intraocular Distances by Backscattering Spectral Interferometry", Optics Communications, vol. 117, pp. 43-48.
Fercher, Adolf F., (1996). "Optical Coherence Tomography", Journal of Biomedical Optics, vol. 1, No. 2, pp. 157-173.
Fernández et al., (2005). "Three-Dimensional Adaptive Optics Ultrahigh-Resolution Optical Coherence Tomography using a Liquid Crystal Spatial Light Modulator", Vision Research, vol. 45, pp. 3432-3444.
Ftimia, (2008). "Dual-Beam Fourier Domain Optical Doppler Tomography of Zebrafish", Optics Express, vol. 16, No. 18, pp. 13624-13636.
Götzinger et al., (2005). "High Speed Spectral Domain Polarization Sensitive Optical Coherence Tomography of the Human Retina", Optics Express, vol. 13, No. 25, pp. 10217-10229.
Götzinger et al., (2009). "Polarization Maintaining Fiber Based Ultra-High Resolution Spectral Domain Polarization Sensitive Optical Coherence Tomography", Optics Express, vol. 17, No. 25, pp. 22704-22717.
Grajciar et al., (2005). "Parallel Fourier Domain Optical Coherence Tomography for in Vivo Measurement of the Human Eye", Optics Express, vol. 13, No. 4, pp. 1131-1137.
Grajciar et al., (2010). "High Sensitivity Phase Mapping with Parallel Fourier Domain Optical Coherence Tomography at 512 000 A-scan/s", Optics Express, vol. 18, No. 21, pp. 21841-21850.
Grajciar et al., (2011). "High-Resolution Phase Mapping with Parallel Fourier Domain Optical Coherence Microscopy for Dispersion Contrast Imaging", Photonics Letters of Poland, vol. 3, No. 4, pp. 135-137.
Grieve et al., (2008). "Intrinsic Signals from Human Cone Photoreceptors", Investigative Ophthalmology & Visual Science, vol. 49, No. 2, pp. 713-719.
Grulkowski et al., (2012). "Retinal, Anterior Segment and full Eye Imaging using Ultrahigh Speed Swept Source OCT with vertical-cavity surface emitting lasers", Biomedical Optics Express, vol. 3, No. 11, pp. 2733-2751.
Gustafsson, M. G. L., (2000). "Surpassing the Lateral Resolution Limit by a factor of two using Structured Illumination Microscopy", Journal of Microscopy, vol. 198, Pt 2, pp. 82-87.
Haindl et al., (2014). "Absolute Velocity Profile Measurement by 3-beam Doppler Optical Coherence Tomography Utilizing a MEMS Scanning Mirror", Biomedical Optics, BT3A.74, 3 pages.
Haindl et al., (2014). "Three-beam Doppler Optical Coherence Tomography using a facet Prism Telescope and MEMS Mirror for Improved Transversal Resolution", Journal of Modern Optics, pp. 1-8.
Hammer et al. "Multimodal adaptive optics retinal imager: design and performance." Journal of the Optical Society of America. A, Optics, image science, and vision vol. 29, (2012) doi:10.1364/JOSAA.29.002598. pp. 2598-2607.
Hamilton et al., (1994). "Crisscross" MR Imaging: Improved Resolution by averaging Signals with Swapped Phase-Encoding Axes, Radiology, vol. 193, pp. 276-279.
Hanazono et al., (2007). "Intrinsic Signal Imaging in Macaque Retina Reveals Different Types of Flash-Induced Light Reflectance Changes of Different Origins", IOVS, vol. 48, No. 6, pp. 2903-2912.
Heintzmann et al., (1999). "Laterally Modulated Excitation Microscopy: Improvement of Resolution by using a Diffraction Grating", SPIE Proceedings, vol. 3568, pp. 185-196.
Hermann et al., (2004). "Adaptive-Optics Ultrahigh-Resolution Optical Coherence Tomography", Optics Letters, vol. 29, No. 18, pp. 2142-2144.
Hillmann et al., (2011). "Holoscopy-Holographic Optical Coherence Tomography", Optics Letters, vol. 36, No. 13, pp. 2390-2392.
Hillmann et al., (2012). "Common Approach for Compensation of Axial Motion Artifacts in Swept-Source OCT and Dispersion in Fourier-Domain OCT", Optics Express, vol. 20, No. 6, pp. 6761-6776.
Hillmann et al., (2012). "Efficient Holoscopy Image Reconstruction", Optics Express, vol. 20, No. 19, pp. 21247-21263.
Hillmann et al., (2016). "Aberration-free Volumetric High-Speed Imaging of in Vivo Retina", Scientific Reports, vol. 6, 35209, 11 pages.
Hillmann et al., (2016). "In Vivo Optical Imaging of Physiological Responses to Photostimulation in Human Photoreceptors", Proc. Natl. Acad. Sci. U.S.A. 113, pp. 13138-13143.
Hillmann et al., (2016). "In Vivo Optical Imaging of Physiological Responses to Photostimulation in Human Photoreceptors", arXiv preprint, arXiv:1605.02959, pp. 1-8.
Hiratsuka et al., (1998). "Simultaneous Measurements of three-Dimensional Reflectivity Distributions in Scattering Media Based on Optical Frequency-Domain Reflectometry", Optics letters, Optical Society of America, vol. 23, No. 18, Sep. 15, 1998, pp. 1420-1422.
Huang et al., (1991). "Optical Coherence Tomography", Science, vol. 254, pp. 1178-1181.
Huber et al., (2005). "Three-Dimensional and C-mode OCT imaging with a Compact, Frequency Swept Laser Source at 1300 nm", Optics Express, vol. 13, No. 26., pp. 10523-10538.
Iftimia et al., (2006). "Hybrid Retinal Imager Using Line-Scanning Laser Ophthalmoscopy and Spectral Domain Optical Coherence Tomography", Optics Express, vol. 14, No. 26, pp. 12909-12914.
Inomata et al., (2008). "Distribution of Retinal Responses Evoked by Transscleral Electrical Stimulation Detected by Intrinsic Signal Imaging in Macaque Monkeys", IOVS, vol. 49, No. 5, pp. 2193-2200.
International Preliminary Report on Patentability received for PCT Application No. PCT/EP2015/062771, mailed on Dec. 22, 2016, 13 pages.
International Search Report and Written Opinion received for PCT Application No. PCT/EP2015/062771, mailed on Dec. 15, 2015, 20 pages.
Jain et al., (2011). "Modified full-field Optical Coherence Tomography: A novel tool for Rapid Histology of Tissues", J Pathol Inform, vol. 2, No. 28, 9 pages.
Jayaraman et al., (2014). "Recent Advances in MEMS-VCSELs for High Performance Structural and Functional SS-OCT Imaging", Proc. of SPIE, vol. 8934, pp. 893402-1-893402-11.
Jonnal et al., (2007). "In Vivo Functional Imaging of Human Cone Photoreceptors", Optics Express, vol. 15, No. 24, pp. 16141-16160.
Kak et al., (1988). "Principles of Computerized Tomographic Imaging", Society for Industrial and Applied Mathematics, 333 pages.
Kim, M. K., (1999). "Wavelength-Scanning Digital Interference Holography for Optical Section Imaging", Optics Letters, vol. 24, No. 23, pp. 1693-1695.
Kim, M. K., (2000). "Tomographic Three-Dimensional Imaging of a Biological Specimen Using Wavelength-Scanning Digital Interference Holography", Optics Express, vol. 7, No. 9, pp. 305-310.
Klein et al., (2013). "Joint Aperture Detection for Speckle Reduction and Increased Collection Efficiency in Ophthalmic MHz OCT", Biomedical Optics Express, vol. 4, No. 4, pp. 619-634.

(56) References Cited

OTHER PUBLICATIONS

Kraus, (2012). "Motion Correction in Optical Coherence Tomography Volumes on a per A-Scan Basis Using Orthogonal Scan Patterns", Biomedical Optics Express, vol. 3, No. 6, pp. 1182-1199.

Kühn et al., "Submicrometer Tomography of Cells by Multiple-Wavelength Digital Holographic Microscopy in Reflection", Optics Letters, vol. 34, No. 5, Mar. 1, 2009, pp. 653-655.

Kumar et al., (2013). "Subaperture Correlation based Digital Adaptive Optics for Full Field Optical Coherence Tomography", Optics Letters, vol. 21, No. 9, pp. 10850-10866.

Kumar et al., (2014). "Numerical Focusing Methods for Full Field OCT: A Comparison Based on a Common Signal Model", Optics Express, vol. 22, No. 13, pp. 16061-16078.

Kumar et al., (2015). "Anisotropic Aberration Correction Using Region of Interest Based Digital Adaptive Optics in Fourier Domain OCT", Optics Express, vol. 6, No. 4, pp. 1124-1134.

Laubscher et al., (2002). "Video-Rate Three-Dimensional Optical Coherence Tomography", Optics Express, vol. 10, No. 9, pp. 429-435.

Lee et al., (2008). "Line-Field Optical Coherence Tomography Using Frequency-Sweeping Source", IEEE Journal of Selected Topics in Quantum Electronics, vol. 14, No. 1, pp. 50-55.

Leitgeb et al., (2003). "Performance of Fourier Domain vs. Time Domain Optical Coherence Tomography", Optics Express, vol. 11, No. 8, pp. 889-894.

Leitgeb et al., (2003). "Real-Time Assessment of Retinal Blood Flow with Ultrafast Acquisition by Color Doppler Fourier Domian Optical Coherence Tomography", Optics Express, vol. 11, No. 23, pp. 3116-3121.

Leitgeb et al., (2004). "Real-Time Measurement of in Vitro Flow by Fourier-Domain Color Doppler Optical Coherence Tomography", Optics Letters, vol. 29, No. 2, pp. 171-173.

Liang et al., (1997). "Confocal Pattern Period in Multiple-Aperture Confocal Imaging Systems with Coherent Illumination", Optics Letters, vol. 22, No. 11, pp. 751-753.

Lippok et al., (2012). "Dispersion Compensation in Fourier Domain Optical Coherence Tomography Using the Fractional Fourier Transform", Optics Express, vol. 20, No. 21, pp. 23398-23413.

Liu et al., (2012). "Distortion-Free Freehand-Scanning OCT Implemented with Real-Time Scanning Speed Variance Correction", Optics Express, vol. 20, No. 15, pp. 16567-16583.

Liu et al., (2014). "Quantitative Phase-Contrast Confocal Microscope", Optics Express, vol. 22, No. 15, pp. 17830-17839.

Machida et al., (2008). "Correlation between Photopic Negative Response and Retinal Nerve Fiber Layer Thickness and Optic Disc Topography in Glaucomatous Eyes", Investigative Ophthalmology & Visual Science, vol. 49, No. 5, pp. 2201-2207.

Marks et al., (2007). "Inverse Scattering for Frequency-Scanned Full-Field Optical Coherence Tomography", Journal of the Optical Society of America A, vol. 24, No. 4, pp. 1034-1041.

Maznev et al., (1998). "How to Make Femtosecond Pulses Overlap", Optics Letters, vol. 23, No. 17, pp. 1378-1380.

Montfort et al., (2006). "Submicrometer Optical Tomography by Multiple-Wavelength Digital Holographic Microscopy", Applied Optics, vol. 45, No. 32, pp. 8209-8217.

Moreau et al., (2003). "Full-field Birefringence Imaging by Thermal-Light Polarization-Sensitive Optical Coherence Tomography. II. Instrument and Results", Applied Optics, vol. 42, No. 19, pp. 3811-3818.

Mujat et al., (2009). "Swept-Source Parallel OCT", Proc. of SPIE, vol. 7168, pp. 71681E-1-71681E-8.

Museth et al., (2002). "Level Set Segmentation from Multiple Non-Uniform Volume Datasets", Visualization, IEEE, pp. 179-186.

Nakamura et al., (2007). "Complex Numerical Processing for In-Focus Line-Field Spectral-Domain Optical Coherence Tomography", Japanese Journal of Applied Physics, vol. 46, No. 4A, pp. 1774-1778.

Nakamura et al., (2007). "High-Speed Three-Dimensional Human Retinal Imaging by Line-Field Spectral Domain Optical Coherence Tomography", Optics Express, vol. 15, No. 12, pp. 7103-7116.

Nankivil et al., (2014). "Coherence revival multiplexed, buffered swept source optical coherence tomography: 400 kHz imaging with a 100 kHz source", Optics Letters, Optical Society of America, vol. 39, No. 13, pp. 3740-3743.

Ng et al., (2005). "Light Field Photography with a Hand-held Plenoptic Camera", Stanford Tech Report CTSR, pp. 1-11.

Office Action received for Japanese Patent Application No. 2016-569071, mailed on Feb. 26, 2019, 9 pages (4 pages of English Translation and 5 pages of Official Copy).

Pavillon et al., (2009). "Suppression of the Zero-Order Term in Off-Axis Digital Holography through Nonlinear Filtering", Applied Optics, vol. 48, No. 34, pp. H186-H195.

Pedersen, Cameron J., (2007). "Measurement of Absolute Flow Velocity Vector Using Dual-Angle, Delay-Encoded Doppler Optical Coherence Tomography", Optics Letters, vol. 32, No. 5, pp. 506-508.

Pircher et al., (2007). "Simultaneous SLO/OCT Imaging of the human Retina with Axial Eye Motion Correction", Optics Express, vol. 15, No. 25, pp. 16922-16932.

Platt et al., (2001). "History and Principles of Shack Hartmann Wavefront Sensing", Journal of Refractive Surgery, vol. 17, pp. S573-S577.

Polans et al., (2017). "Wide-Field Retinal Optical Coherence Tomography with Wavefront Sensorless Adaptive Optics for Enhanced Imaging of Targeted Regions", Biomedical Optics Express, vol. 8, No. 1, pp. 16-37.

Potsaid et al., (2010). "Ultrahigh Speed 1050nm Swept Source / Fourier Domain OCT Retinal and Anterior Segment Imaging at 100,000 to 400,000 Axial Scans per Second", Optics Express, vol. 18, No. 19, pp. 20029-20048.

Považay et al., (2003). "Enhanced Visualization of Choroidal Vessels Using Ultrahigh Resolution Ophthalmic OCT at 1050 nm", Optics Express, vol. 11, No. 17, pp. 1980-1986.

Považay et al., (2006). "Full-Field Time-Encoded Frequency-Domain Optical Coherence Tomography", Optics Express, vol. 14, No. 17, pp. 7661-7669.

Ralston et al., (2006). "Inverse Scattering for High-Resolution Interferometric Microscopy", Optics Express, vol. 31, No. 24, pp. 3585-3587.

Ralston et al., (2008). "Real-Time Interferometric Synthetic Aperture Microscopy", Optics Express, vol. 16, No. 4, pp. 2555-2569.

Rodríguez-Ramos et al., (2009). "The Plenoptic Camera as a Wavefront Sensor for the European Solar Telescope (EST)", Astronomical and Space Optical Systems, pp. 74390I-74399.

Roullota et al., (2004). "Modeling Anisotropic Undersampling of Magnetic Resonance Angiographies and Reconstruction of a High-Resolution Isotropic Volume Using Half-Quadratic Regularization Techniques", Signal Processing, vol. 84, pp. 743-762.

Rueckel et al., (2006). "Adaptive Wavefront Correction In Two-Photon Microscopy Using Coherence-Gated Wavefront Sensing", PNAS, vol. 103, No. 46, pp. 17137-17142.

Sarunic et al., (2006). "Full-Field Swept-Source Phase Microscopy", Optics Letters, vol. 31, No. 10, pp. 1462-1464.

Sasaki et al., (2012). "Extended Depth of Focus Adaptive Optics Spectral Domain Optical Coherence Tomography", Biomedical Optics Express, vol. 3, No. 10, pp. 2353-2370.

Schmoll et al., (2009). "Ultra-High-Speed Volumetric Tomography Of Human Retinal Blood Flow", Optics Express, vol. 17, pp. 4166-4176.

Schmoll et al., (2010). "In Vivo Functional Retinal Optical Coherence Tomography", Journal of Biomedical Optics, vol. 15, No. 4, pp. 041513-1-041513-8.

Schmoll et al., (2010). "Single-Camera Polarization-Sensitive Spectral-Domain Oct By Spatial Frequency Encoding", Optics Letters, vol. 35, No. 2, pp. 241-243.

Sharon et al., (2007). "Cortical Response Field Dynamics in Cat Visual Cortex", Cerebral Cortex, vol. 17, No. 12, pp. 2866-2877.

Shemonski et al., (2014). "Stability in computed optical interferometric tomography (Part I): Stability requirements", Optics Express, vol. 22, No. 16, pp. 19183-19197.

Shemonski et al., (2014). "Stability in computed optical interferometric tomography (Part II): in vivo stability assessment", Optics Express, vol. 22, No. 16, pp. 19314-19326.

(56) References Cited

OTHER PUBLICATIONS

Shemonski et al., (2015). "Computational high-resolution optical imaging of the living human retina", Nature Photonics, Advance Online Publication, pp. 440-443.
Spahr et al., (2015). "Imaging pulse wave propagation in human retinal vessels using full-field swept-source optical coherence tomography", Optics Letters, vol. 40, No. 20, pp. 4771-4774.
Srinivasan et al., (2009). "In Vivo Functional Imaging of Intrinsic Scattering Changes in the Human Retina with High-speed Ultrahigh Resolution OCT", Optics Express, vol. 17, No. 5, pp. 3861-3877.
Stifter et al., (2010). "Dynamic Optical Studies in materials Testing with Spectral-domain Polarization-Sensitive optical Coherence Tomography", Optics Express, vol. 18, No. 25, pp. 25712-25725.
Sudkamp et al., (2016). "In-Vivo Retinal Imaging With Off-Axis Full-Field Time-Domain Optical Coherence Tomography", Optics Letters, vol. 41, No. 21, pp. 4987-4990.
Sun et al., (2010). "3D In Vivo Optical Coherence Tomography based on a Low-Voltage, Large-Scan-Range 2D MEMS Mirror", Optics Express, vol. 18, No. 12, pp. 12065-12075.
Tajahuerce et al., (2014). "Image Transmission through Dynamic Scattering Media by Single-Pixel Photodetection", Optics Express, vol. 22, No. 14, pp. 16945-16955.
Tamez-Peña et al., (2001). "MRI Isotropic Resolution Reconstruction from two Orthogonal Scans", Proceedings of SPIE vol. 4322, pp. 87-97.
Tippie et al., (2011). "High-Resolution Synthetic-Aperture Digital Holography with Digital Phase and Pupil Correction", Optics Express, vol. 19, No. 13, pp. 12027-12038.
Trasischker et al., (2013). "In vitro and in vivo three-dimensional Velocity Vector measurement by Threebeam Spectral-Domain Doppler Optical Coherence Tomography", Journal of Biomedical Optics, vol. 18, No. 11, pp. 116010-1-116010-11.
Tsunoda et al, (2004). "Mapping Cone- and Rod-Induced Retinal Responsiveness in Macaque Retina by Optical Imaging", Investigative Ophthalmology & Visual Science, vol. 45, No. 10, pp. 3820-3826.
Unterhuber et al., (2005). "In vivo Retinal Optical Coherence Tomography at 1040 nm—Enhanced Penetration into the Choroid", Optics Express, vol. 13, No. 9, pp. 3252-3258.
Wang et al., (2011). "Megahertz Streak-Mode Fourier Domain Optical Coherence Tomography", Journal of Biomedical Optics, vol. 16, No. 6, pp. 066016-1-066016-8.
Wartak et al., (2016). "Active-Passive Path-Length Encoded (APPLE) Doppler OCT", Biomedical Optics Express, vol. 7, No. 12, pp. 5233-5251.
Werkmeister et al., (2008). "Bidirectional Doppler Fourier-Domain Optical Coherence Tomography For Measurement Of Absolute Flow Velocities In Human Retinal Vessels", Optics Letters, vol. 33, No. 24, pp. 2967-2969.
Wieser et al., (2010). "Multi-Megahertz Oct: High Quality 3d Imaging At 20 Million A-Scans And 4.5 Gvoxels Per Second", Optics Express, vol. 18, No. 14, pp. 14685-14704.
Wojtkowski et al., (2004). "Ultrahigh-Resolution High-Speed, Fourier Domain Optical Coherence Tomography and Methods for Dispersion Compensation", Optics Express, vol. 12, No. 11, pp. 2404-2422.
Wolf, Emil, (1969). "Three-Dimensional Structure Determination of Semi-Transparent Objects from Holographic Data", Optics Communications, vol. 1, No. 4, pp. 153-156.
Xu et al., (2014). "Multifocal Interferometric Synthetic Aperture Microscopy", Optics Express, vol. 22, No. 13, pp. 16606-16618.
Yu et al., (2006). "Variable Tomographic Scanning With Wavelength Scanning Digital Interference Holography", Optics Communications, vol. 260, pp. 462-468.
Yun et al., (2004). "Motion artifacts in optical coherence tomography with frequency-domain ranging", Optics Express, vol. 12, No. 13, pp. 2977-2998.
Zawadzki et al., (2005). "Adaptive-Optics Optical Coherence Tomography for High-Resolution and High-Speed 3D Retinal in Vivo Imaging", Optics Express, vol. 13, No. 21, pp. 8532-8546.
Zhang et al., (2004). "Integrated Fluidic Adaptive Zoom Lens", Optics Letter, vol. 29, No. 24, pp. 2855-2857.
Zuluaga et al., (1999). "Spatially Resolved Spectral Interferometry for Determination of Subsurface Structure", Optics Letters, vol. 24, No. 8, Apr. 15, 1999, pp. 519-521.
Final Office Action received for U.S. Appl. No. 15/311,499, mailed on Sep. 20, 2018, 15 pages.
Final Office Action received for U.S. Appl. No. 15/311,499, mailed on Sep. 9, 2019, 15 pages.
Non-Final Office Action received for U.S. Appl. No. 15/311,499, mailed on Feb. 9, 2018, 15 pages.
Non-Final Office Action received for U.S. Appl. No. 15/311,499, mailed on Jan. 14, 2019, 15 pages.
Non-Final Office Action received for U.S. Appl. No. 15/311,499, mailed on Jan. 2, 2020, 18 pages.
USPTO; Notice of Allowance dated Jun. 16, 2020 in U.S. Appl. No. 15/311,499.
USPTO; Notice of Allowance dated Sep. 19, 2023 in U.S. Appl. No. 17/014,374.
USPTO; Corrected Notice of Allowance dated Sep. 27, 2023 in U.S. Appl. No. 17/014,374.

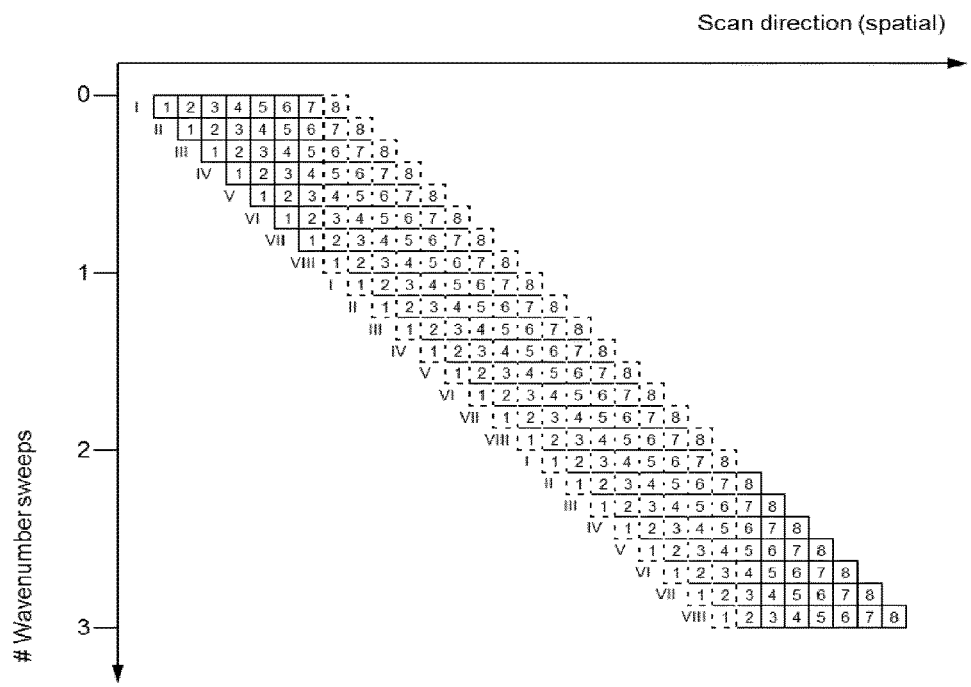
FIG. 7
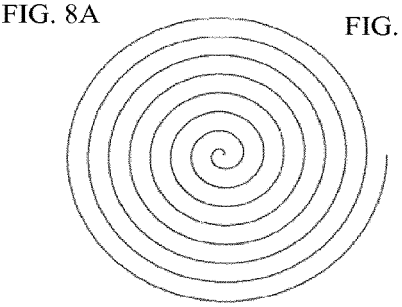
FIG. 8A
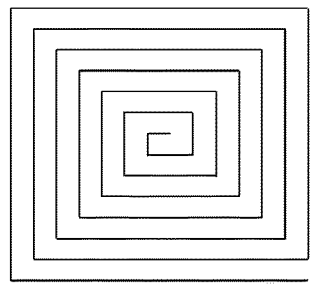
FIG. 8B
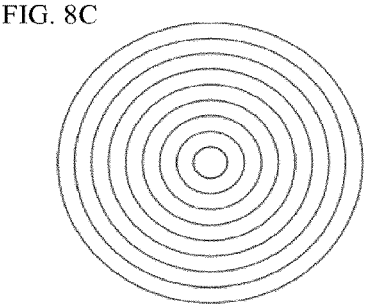
FIG. 8C
FIG. 8

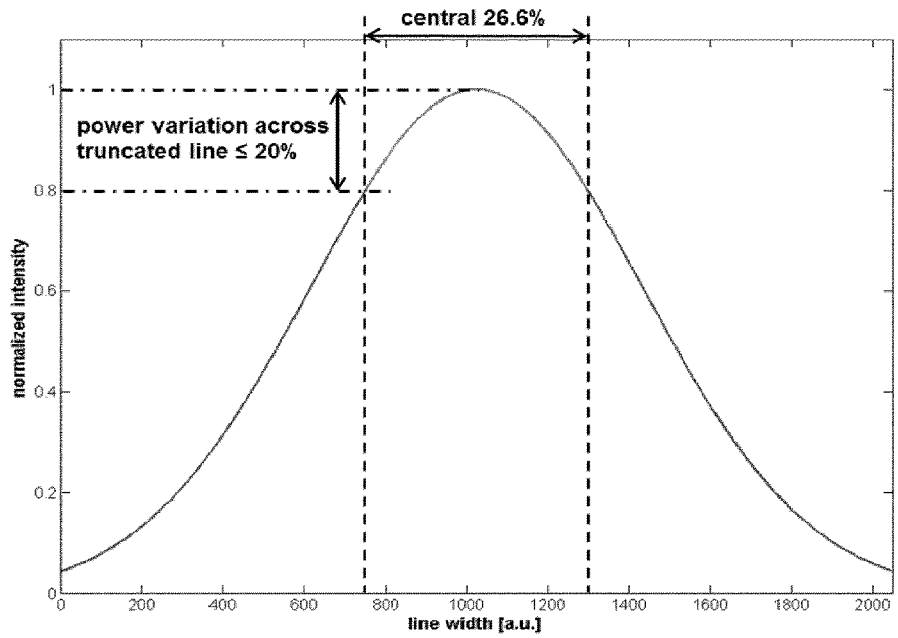
FIG. 11
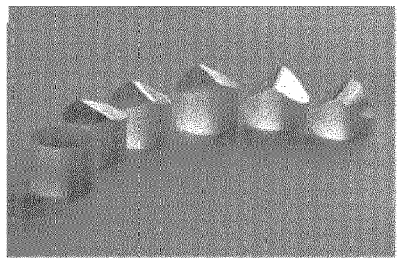
FIG. 12A
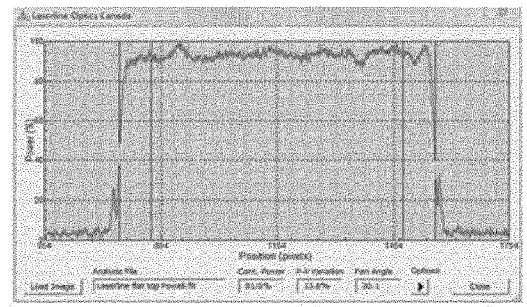
FIG. 12B
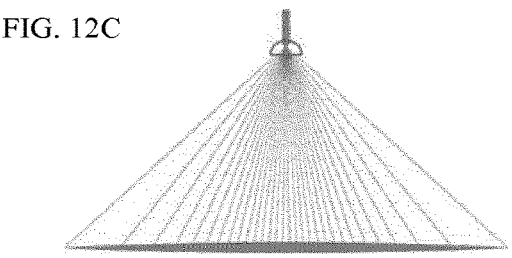
FIG. 12C
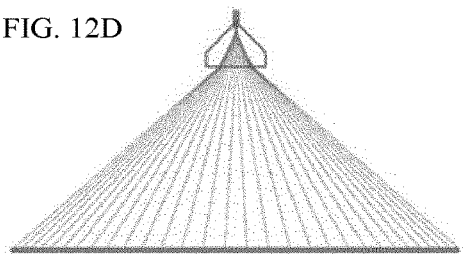
FIG. 12D
FIG. 12
(Prior Art)

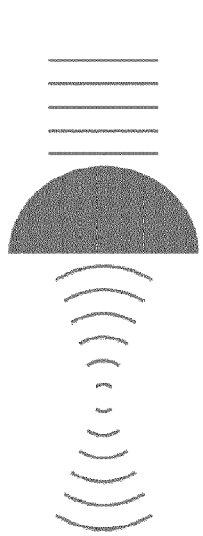
FIG. 13A
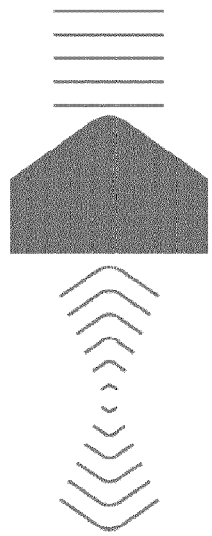
FIG. 13B
FIG. 13
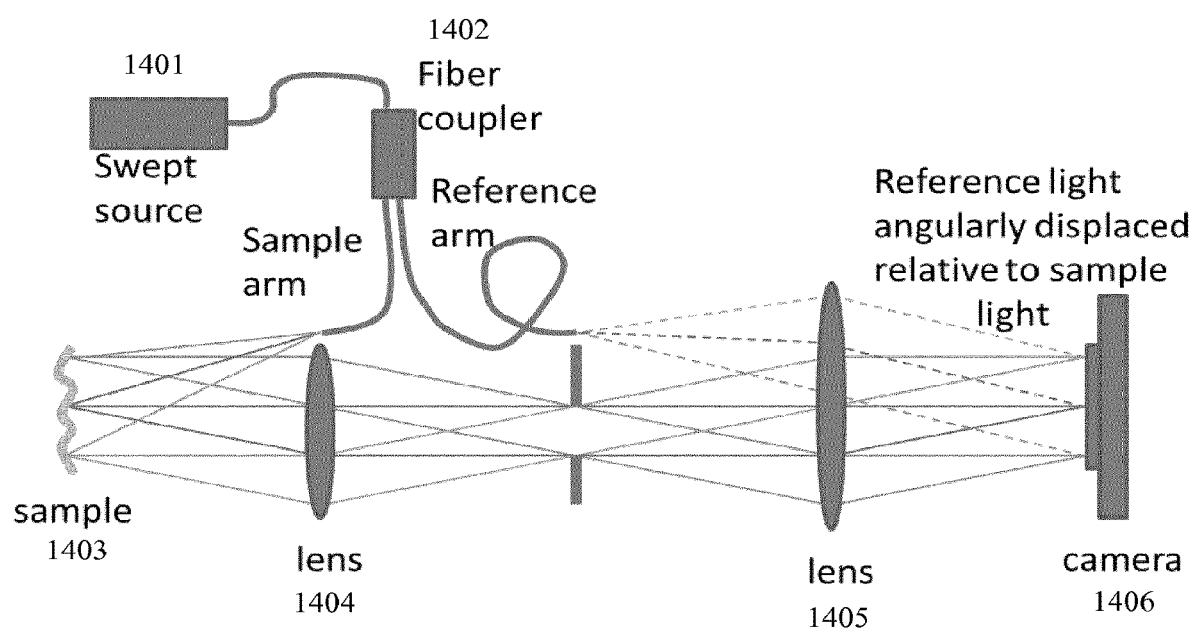
FIG. 14

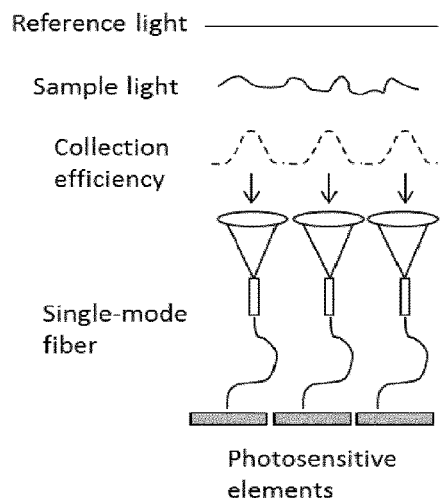
FIG. 18A
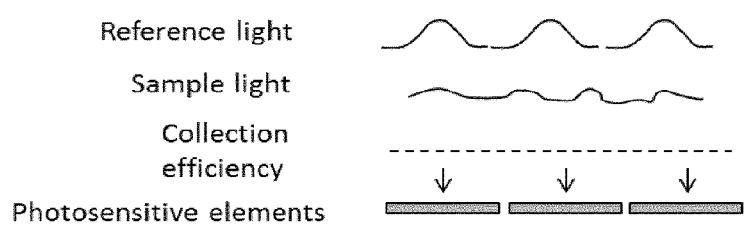
FIG. 18B  FIG. 18C
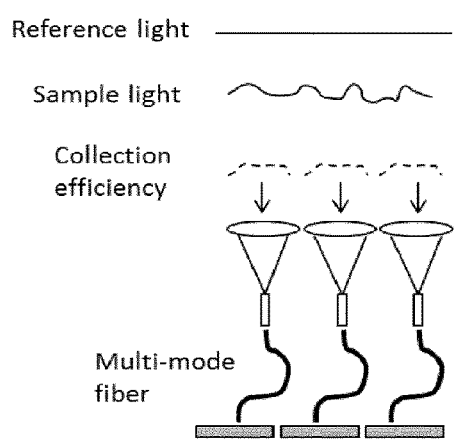
FIG. 18D
FIG. 18

FREQUENCY-DOMAIN INTERFEROMETRIC BASED IMAGING SYSTEMS AND METHODS

CROSS-REFERENCE TO RELATED APPLICATIONS

This application is a divisional of, claims priority to U.S. application Ser. No. 17/014,374 filed on Sep. 8, 2020 and titled "FREQUENCY-DOMAIN INTERFEROMETRIC BASED IMAGING SYSTEMS AND METHODS" (hereinafter the '374 application). The '374 application is a continuation of, claims priority to U.S. National Stage application Ser. No. 15/311,499 filed on Nov. 15, 2016 and titled "IMPROVED FREQUENCY-DOMAIN INTERFEROMETRIC BASED IMAGING SYSTEMS AND METHODS," (U.S. Pat. No. 10,799,11 issued on Oct. 13, 2020) (hereinafter the '499 application). The '499 application claims priority to International Application Serial No. PCT/EP2015/062771 filed on Jun. 9, 2015 and titled "IMPROVED FREQUENCY-DOMAIN INTERFEROMETRIC BASED IMAGING SYSTEMS AND METHODS" (hereinafter the '771 application). The '771 application claims priority to, and benefit of, U.S. Provisional Application Ser. No. 62/112,577 filed Feb. 5, 2015 and titled "IMPROVED FREQUENCY-DOMAIN INTERFEROMETRIC BASED IMAGING SYSTEMS AND METHODS" (hereinafter the '577 application). The '771 application claims priority to, and benefit of, U.S. Provisional Application Ser. No. 62/031,619 filed Jul. 31, 2014 and titled "IMPROVED FREQUENCY-DOMAIN INTERFEROMETRIC BASED IMAGING SYSTEMS AND METHODS" (hereinafter '619 application). The '771 application claims priority to, and benefit of, U.S. Provisional Application Ser. No. 62/010,367 filed on Jun. 10, 2014 and titled "IMPROVED FREQUENCY-DOMAIN INTERFEROMETRIC BASED IMAGING SYSTEMS AND METHODS" (hereinafter the '367 application). Each of the foregoing applications are hereby incorporated by reference in their entirety for all purposes.

FIELD

The present application relates to the field of interferometric imaging systems.

BACKGROUND

A wide variety of interferometric based imaging techniques have been developed to provide high resolution structural information of samples in a range of applications. Optical Coherence Tomography (OCT) is an interferometric technique that can provide images of samples including tissue structure on the micron scale in situ and in real time (Huang, D. et al., Science 254, 1178-81, 1991). OCT is based on the principle of low coherence interferometry (LCI) and determines the scattering profile of a sample along the OCT beam by detecting the interference of light reflected from a sample and a reference beam (Fercher, A. F. et al., Opt. Lett. 13, 186, 1988). Each scattering profile in the depth direction (z) is reconstructed individually into an axial scan, or A-scan. Cross-sectional images (B-scans), and by extension 3D volumes, are built up from many A-scans, with the OCT beam moved to a set of transverse (x and y) locations on the sample.

Many variants of OCT have been developed where different combinations of light sources, scanning configurations, and detection schemes are employed. In time domain OCT (TD-OCT), the pathlength between light returning from the sample and reference light is translated longitudinally in time to recover the depth information in the sample. In frequency-domain or Fourier-domain OCT (FD-OCT), a method based on diffraction tomography (Wolf, E., Opt. Commun. 1, 153-156, 1969), the broadband interference between reflected sample light and reference light is acquired in the spectral frequency domain and a Fourier transform is used to recover the depth information (Fercher, A. F. et al., Opt. Commun. 117, 43-48, 1995). The sensitivity advantage of FD-OCT over TD-OCT is well established (Leitgeb, R. et al., Opt. Express 11, 889, 2003; Choma, M. et al., Opt. Express 11, 2183-9, 2003).

There are two common approaches to FD-OCT. One is spectral domain OCT (SD-OCT) where the interfering light is spectrally dispersed prior to detection and the full depth information can be recovered from a single exposure. The second is swept-source OCT (SS-OCT) where the source is swept over a range of optical frequencies and detected in time, therefore encoding the spectral information in time. In traditional point scanning or flying spot techniques, a single point of light is scanned across the sample. These techniques have found great use in the field of ophthalmology. However, current point scanning systems for use in ophthalmology illuminate the eye with less than 10% of the maximum total power possible for eye illumination spread over a larger area, detect only about 5% of the light exiting the pupil and use only about 20% of the eye's numerical aperture (NA). It may not be immediately possible to significantly improve these statistics with the current point-scanning architectures since the systems already operate close to their maximum permissible exposure for a stationary beam, suffer from out of focus signal loss, and do not correct for aberrations. Parallel techniques may be able to overcome these challenges.

In parallel techniques, a series of spots (multi-beam), a line of light (line-field), or a two-dimensional field of light (partial-field and full-field) is directed to the sample. The resulting reflected light is combined with reference light and detected. Parallel techniques can be accomplished in TD-OCT, SD-OCT or SS-OCT configurations. Spreading the light on the retina over a larger area will enable higher illumination powers. A semi- or non-confocal parallel detection of a larger portion of the light exiting the pupil will significantly increase the detection efficiency without losing out of focus light. The fast acquisition speed will result in comprehensively sampled volumes which are required for applying computational imaging techniques. Several groups have reported on different parallel FD-OCT configurations (Hiratsuka, H. et al., Opt. Lett. 23, 1420, 1998; Zuluaga, A. F. et al., Opt. Lett. 24, 519-521, 1999; Grajciar, B. et al., Opt. Express 13, 1131, 2005; Blazkiewicz, P. et al., Appl. Opt. 44, 7722, 2005; Považay, B. et al., Opt. Express 14, 7661, 2006; Nakamura, Y. et al., Opt. Express 15, 7103, 2007; Lee, S.-W. et al., IEEE J. Sel. Topics Quantum Electron. 14, 50-55, 2008; Mujat, M. et al., Optical Coherence Tomography and Coherence Domain Optical Methods in Biomedicine XIII 7168, 71681E, 2009; Bonin, T. et al., Opt. Lett. 35, 3432-4, 2010; Wieser, W. et al., Opt. Express 18, 14685-704, 2010; Potsaid, B. et al., Opt. Express 18, 20029-48, 2010; Klein, T. et al., Biomed. Opt. Express 4, 619-34, 2013; Nankivil, D. et al., Opt. Lett. 39, 3740-3, 2014).

The related fields of holoscopy, digital interference holography, holographic OCT, and Interferometric Synthetic Aperture Microscopy are also interferometric imaging techniques based on diffraction tomography (Kim, M. K., Opt. Lett. 24, 1693-1695, 1999; Kim, M.-K., Opt. Express 7, 305, 2000; Yu, L. et al., Opt. Commun. 260, 462-468, 2006; Marks, D. L. et al., J. Opt. Soc. Am. A 24, 1034, 2007; Hillmann, D. et al., Opt. Lett. 36, 2390-2, 2011). All of these techniques fall in the category of computational imaging techniques, meaning that post-processing is typically necessary to make the acquired data comprehendible for humans. They are commonly implemented in full-field configurations, although interferometric synthetic aperture microscopy is often also used in a point-scanning configuration.

SUMMARY

I. Introduction
 a. Definitions
 b. System Descriptions
II. Partial field frequency-domain interferometric imaging
III. Scanning Related Improvements
 a. Scanning of a two-dimensional area or line in X&Y
 b. Creating a spatial oversampling through scanning
 c. Use of DMD in parallel frequency-domain imaging
 d. Scanning with MEMS mirror array
 e. Scanning with a single MEMS mirror
 f. Orthogonal scan patterns
 g. Wide field scanning—Non-raster scan to reduce scan depth variability
 h. Wide field scanning—reflective delivery optics
 i. High speed scanning
 j. Scanner-less systems
IV. Acquisition related improvements
 a. Streak mode line field frequency-domain imaging
 b. Optical fiber bundles
 c. Pupil camera
V. Reconstruction and Computational Adaptive Optics
 a. Computational Chromatic Aberration Correction
 b. Hybrid hardware/computational adaptive optics
 c. Sub-aperture auto-focusing
 d. Taking image distortions into account for reconstruction
 e. Stacking of holoscopy acquisitions
 f. Reconstructions for preview and alignment mode
 g. Synthetic aperture off-axis holoscopy
VI. Motion correction
 a. Tracking and correction of motion and rotation occurring during acquisition of parallel frequency-domain imaging data
 b. Off-axis detection for tracking and correction of motion and rotation
 c. Tracking and correction of motion and rotation using a single contiguous patch
 d. Tracking of motion by absolute angle resolved velocity measurements
 e. Errors in motion measurements
VII. Illumination
 a. 1060 nm holoscopy
 b. Intentionally aberrated illumination optics
 c. Light source arrays
 d. Separation of illumination and detection path
 e. Continuous scanning with time-varying illumination
 f. Variable optical power
VIII. Reference signal and reference arm design related improvements
 a. Record reference signal at edge of detector
 b. Record source light at edge of detector
 c. Lensless line-field reference arm
IX. Applications
 a. Fundus imaging and enface imaging
 b. Directional scattering
 c. Tissue specific directional scattering
 d. Dark field imaging
 e. Absolute angle resolved velocity measurements
 f. Stereoscopic viewing
 g. Functional imaging
 h. Angiography
 i. Polarization sensitive holoscopy

BRIEF DESCRIPTION OF THE FIGURES

FIG. 7 shows a schematic of the order in which data is acquired and how it should be grouped for reconstruction in continuous fast scanning mode.

FIG. 8 illustrates several alternative scan patterns that could be used to scan the illumination in two-dimensional scanning based systems.

FIG. 8A shows a spiral scan pattern.

FIG. 8B shows a square spiral pattern, and FIG. 8C shows a concentric circle scan pattern.

FIG. 11 shows a plot of a Gaussian normalized intensity distribution.

FIG. 12A illustrates a collection of Powell lenses as is known from the prior art.

FIGS. 12C and 12D illustrate how the components of the Powell lens change the intensity distribution along its two axes.

FIG. 12B illustrates the homogeneous intensity distribution that results.

FIG. 13A shows the cylindrical wavefronts that result from light traveling through a cylindrical lens.

FIG. 13B illustrates how Powell lenses can create non-cylindrical wavefronts.

FIG. 14 illustrates an embodiment of a parallel field frequency-domain interferometric system in which the incident and returning sample light are separated in space.

FIG. 18 illustrates the beam properties and collection efficiencies for four different light and detection configurations.

FIG. 18A shows the case where light is detected using single mode fibers.

FIG. 18B shows the case where reference light having Gaussian profiles is detected by photosensitive elements.

FIG. 18C shows the case where uniform reference light is detected by photosensitive elements.

FIG. 18D shows the case where light is detected using multi-mode fibers.

DETAILED DESCRIPTION

I. Introduction

Figure 1:
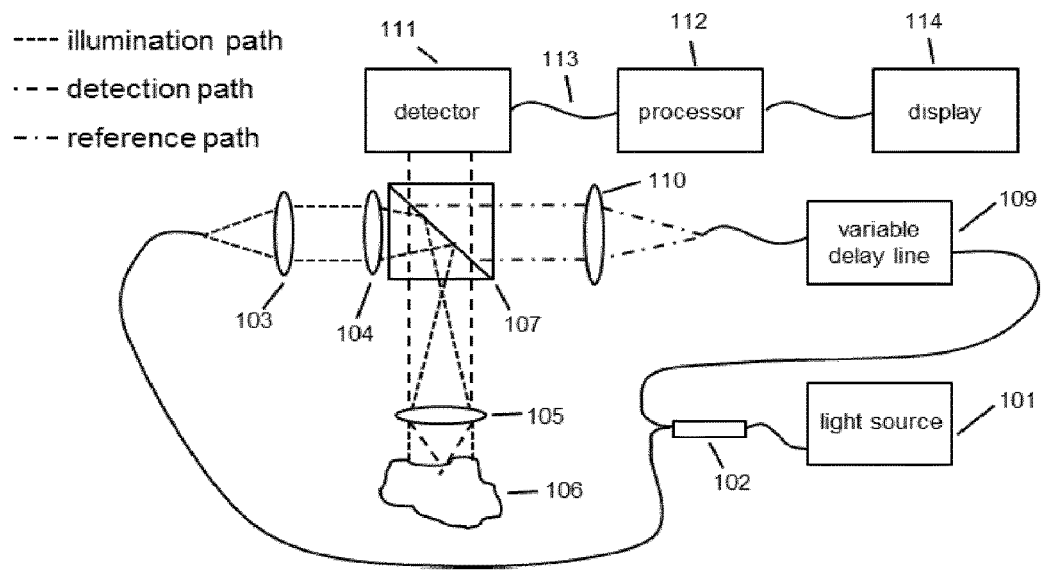
FIG. 1 illustrates a prior art swept-source based full-field holoscopy system.

Various aspects of interferometric and holoscopic systems have been described in some of our co-pending applications (see for example US Patent Publication No. 2014/0028974, US Patent Publication No. 2015/0092195, PCT Publication No. WO 2015/052071, PCT Publication No. WO 2015/024663, U.S. application Ser. No. 14/613,121, the contents of all of which are hereby incorporated by reference). A split aperture processing for interferometric systems has been described in US Patent Publication No. 2014/0218684 hereby incorporated by reference.

a. Definitions

The following definitions may be useful in understanding the detailed description:

Interferometric system: A system in which electromagnetic waves are superimposed, in order to extract information about the waves. Typically a single beam of at least partially coherent light is split and directed into different paths. These paths are commonly called sample path and reference path, containing sample light and reference light. The difference in optical path length creates a phase difference between them, which results in constructive or destructive interference. The interference pattern can be further analyzed and processed to extract additional information. There are special cases of interferometric systems, e.g. common path interferometers, in which the sample light and reference light travel along a shared path.

OCT System: An interferometric imaging system that determines the scattering profile of a sample along the OCT beam by detecting the interference of light reflected from a sample and a reference beam creating a three-dimensional (3D) representation of the sample. Each scattering profile in the depth direction (z) is reconstructed individually into an axial scan, or A-scan. Cross-sectional images (B-scans), and by extension 3D volumes, are built up from many A-scans, with the OCT beam moved to a set of transverse (x and y) locations on the sample. The axial resolution of an OCT system is inversely proportional to the spectral bandwidth of the employed light source. The lateral resolution is defined by the numerical aperture of the illumination and detection optics and decreases when moving away from the focal plane. OCT systems exist in time domain and frequency domain implementations, with the time domain implementation based on low coherence interferometry (LCI) and the frequency domain implementation based on diffraction tomography. OCT systems can be point-scanning, multi-beam or field systems.

Holoscopy: An interferometric frequency-domain computational imaging technique that detects backscattered light from multiple angles, in order to reconstruct a 3D representation of a sample with spatially invariant resolution. If the angular information from a single point, line, or two-dimensional area acquisition is insufficient for successfully reconstructing said 3D representation of a sample, two or more adjacent acquisitions can be combined to reconstruct said 3D representation of a sample. Holoscopy systems can be point-scanning, multi-beam or field systems.

Spatially invariant resolution: A lateral resolution that is to first order independent of the axial position of the optical focal plane. Optical aberrations and errors in the reconstruction may lead to a slight loss of resolution with depth. This stands in contrast to Gaussian optics where the lateral resolution decreases when moving away from the focal plane.

Computational adaptive optics: The computational correction of aberrations with a higher order than defocus.

Point-scanning system: A confocal scanning system that transversely scans the sample with a small spot and detects the backscattered light from the spot at a single point. The single point of detection may be spectrally dispersed or split into two channels for balanced detection. Many points have to be acquired in order to capture a 2D image or 3D volume. Cirrus™ HD-OCT (Carl Zeiss Meditec, Inc. Dublin, CA) as well as all other commercial ophthalmic OCT devices, are currently point-scanning systems.

Multi-beam system: A system that transversely scans the sample with multiple confocal points in parallel. A multi-beam system typically employs a dedicated interferometer for each parallel acquisition channel. The backscattered sample light of each parallel acquisition channel is typically coupled into a dedicated single mode fiber for each parallel acquisition channel.

Field illumination system: An interferometric imaging system wherein the sample is illuminated with a contiguous field of light which is then detected with a spatially-resolved detector. This is in contrast to imaging systems which use a focused spot or multiple spatially-separated focused spots with a single detector for each spot. Examples of field illumination systems include line-field, partial-field and full-field systems.

Line field system: A field illumination system that illuminates the sample with a line and detects backscattered light with a spatially resolved detector. Such systems typically allow capturing a B-scan without transverse scanning In order to acquire an enface image or volume of the sample, the line has to be scanned across the sample in one transverse direction.

Partial-field system: A field illumination system that illuminates an area of the sample which is smaller than the desired field of view and detects the backscattered light with a spatially resolved detector. In order to acquire an enface image or volume of the entire desired field of view one requires transverse scanning in two dimensions. A partial field illumination could be e.g., a spot created by a low NA beam, a line, or any two-dimensional area including but not limited to a broad-line, an elliptical, square or rectangular illumination.

Full-field system: A field illumination system that illuminates the entire field of view (FOV) of the sample at once and detects the backscattered light with a spatially resolved detector. In order to acquire an enface image or volume, no transverse scanning is required.

Photosensitive element: An element that converts electromagnetic radiation (i.e. photons) into an electrical signal. It could be a photodiode, phototransistor, photoresistor, avalanche photodiode, nano-injection detector, or any other element that can translate electromagnetic radiation into an electrical signal. The photosensitive element could contain, on the same substrate or in close proximity, additional circuitry, including but not limited to transistors, resistors, capacitors, amplifiers, analog to digital converters, etc. When a photosensitive element is part of a detector it is also commonly referred to as pixel, sensel or photosite. A detector or camera can have an array of photosensitive elements.

Detector: We distinguish between 0D, 1D and 2D detectors. A 0D detector would typically use a single photosensitive element to transform photon energy into an electrical signal. Spatially resolved detectors, in contrast to 0D detectors, are capable of inherently generating two or more spatial sampling points. 1D and 2D detectors are spatially resolved detectors. A 1D detector would typically use a linear array of photosensitive elements to transform photon energy into electrical signals. A 2D detector would typically use a 2D array of photosensitive elements to transform photon energy into electrical signals. The photosensitive elements in the 2D detector may be arranged in a rectangular grid, square grid, hexagonal grid, circular grid, or any other arbitrary spatially resolved arrangement. In these arrangements the photosensitive elements may be evenly spaced or may have arbitrary distances in between individual photosensitive elements. The 2D detector could also be a set of 0D or 1D detectors optically coupled to a 2D set of detection locations. Likewise a 1D detector could also be a set of 0D detectors or a 1D detector optically coupled to a 2D grid of detection locations. These detection locations could be arranged similarly to the 2D detector arrangements described above. A detector can consist of several photosensitive elements on a common substrate or consist of several separate photosensitive elements. Detectors may further contain amplifiers, filters, analog to digital converters (ADCs), processing units or other analog or digital electronic elements on the same substrate as the photosensitive elements, as part of a read out integrated circuit (ROIC), or on a separate board (e.g. a printed circuit board (PCB)) in proximity to the photosensitive elements. A detector which includes such electronics in proximity to the photosensitive elements is in some instances called "camera."

Light beam: Should be interpreted as any carefully directed light path.

Coordinate system: Throughout this application, the X-Y plane is the enface or transverse plane and Z is the dimension of the beam direction.

Enface image: An image in the X-Y plane. Such an image can be a discrete 2D image, a single slice of a 3D volume or a 2D image resulting from projecting a 3D volume or a subsection of a 3D volume in the Z dimension. A fundus image is one example of an enface image.

b. System Descriptions

A prior art swept source based full-field holoscopy system (Hillmann, D. et al., Opt. Express 20, 21247-63, 2012) is illustrated in FIG. 1. Light from a tunable light source 101 is split into sample and reference light by a fused fiber coupler 102. Light in the sample path or arm is collimated by a spherical lens 103. Spherical lenses 104 and 105 are used to illuminate a sample 106 with a field of light that is capable of illuminating the entire FOV. Before the light reaches the sample 106, it passes a beam splitter 107. Sample light scattered by the sample travels back towards the beam splitter 107. Light in the reference path or arm first passes a variable delay line 109 which allows adjustment of the optical path length difference between sample and reference light. It is then collimated by a spherical lens 110 to a reference beam. By the time the scattered light returning from the sample passes the beam splitter 107, the reference light travelled close to the same optical path length as the sample arm light did. At the beam splitter 107 reference light and the light backscattered by the sample are recombined and coherently interfere with each other. The recombined light is then directed towards a 2D detector 111. In some full-field holoscopy system implementations, the position of the detector 111 can correspond to a conjugate plane of the pupil, a conjugate plane of the sample, or lie in between a conjugate plane of the pupil and a conjugate plane of the sample.

The electrical signals from the detector 111 are transferred to the processor 112 via a cable 113. The processor 112 may contain for example a field-programmable gate array (FPGA), a digital signal processor (DSP), an application specific integrated circuit (ASIC), a graphic processing unit (GPU), a system on chip (SoC) or a combination thereof, which performs some, or the entire holoscopy signal processing steps, prior to passing the data on to the host processor. The processor is operably attached to a display 114 for displaying images of the data. The sample and reference arms in the interferometer could consist of bulk-optics, photonic integrated circuits, fiber-optics or hybrid bulk-optic systems and could have different architectures such as Michelson, Mach-Zehnder or common-path based designs as would be known by those skilled in the art.

Full-field interferometric systems acquire many A-scans in parallel, by illuminating the sample with a field of light and detecting the backscattered light with a 2D detector. While the tunable laser sweeps through its optical frequencies, several hundred acquisitions on the detector are required in order to be able to reconstruct a cross-section or volume with a reasonable depth (>500 µm) and resolution. Instead of using transverse scanning to image a desired FOV, full-field systems illuminate and detect the entire FOV at once. A desired minimum FOV size for imaging the human retina in-vivo is 6 mm×6 mm Previously published frequency-domain full-field systems exhibited so far somewhat smaller FOVs, for example Bonin et al. demonstrated a full-field system with a 2.5 mm×0.094 mm FOV (Bonin, T. et al., Opt. Lett. 35, 3432-4, 2010) and Povazay et al. demonstrated a full-field system with a 1.3 mm×1 mm FOV (Povazay, B. et al., Opt. Express 14, 7661, 2006). Also time domain full-field OCT implementations have been published (Laubscher, M. et al., Opt. Express 10, 429, 2002; Jain, M. et al., Journal of pathology informatics 2, 28, 2011; Boccara, C. et al., SPIE Newsroom 2013).

Figure 2:
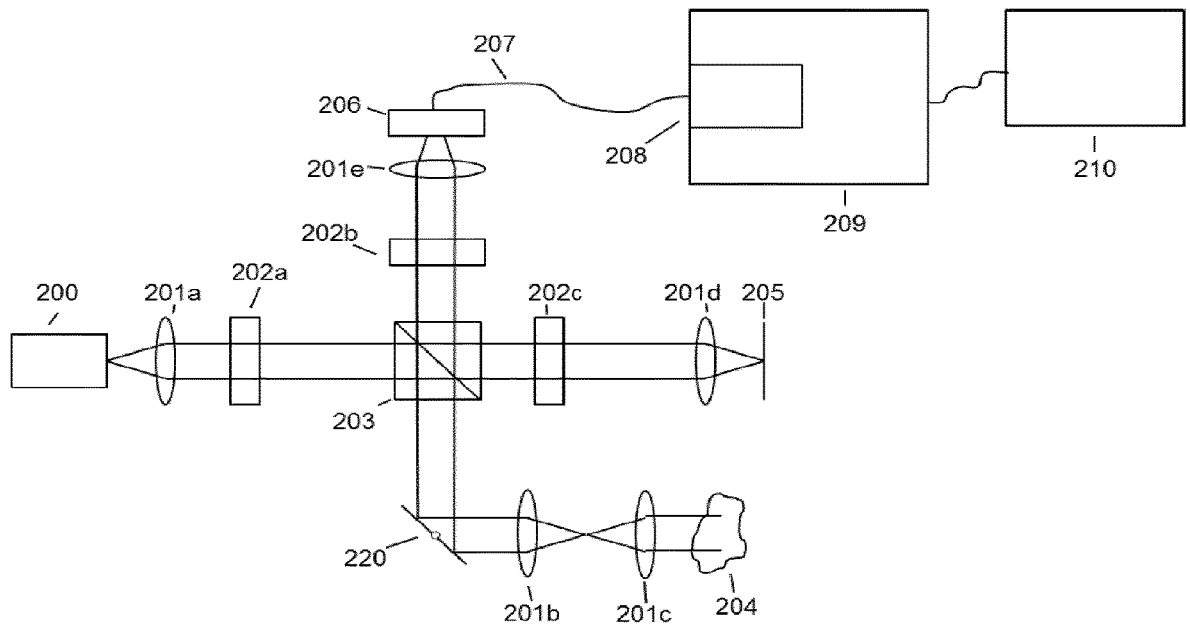
FIG. 2 illustrates a prior art swept-source based line-field holoscopy system.

A prior art swept source based line-field holoscopy system (US Patent Publication No. 2014/0028974) is illustrated in FIG. 2. Light from a tunable light source 200 is collimated by a spherical lens 201a. A cylindrical lens 202a creates a line of light from the source, and the light is split into sample arm and reference arm by a beam splitter 203. A 1-axis scanner 220 adjusts the transverse location of the line of light on the sample in the direction perpendicular to the line. A pair of spherical lenses 201b and 201c images the line onto the sample 204. The light in the reference arm is transferred back to a collimated beam by a cylindrical lens 202c before it is focused on a mirror by a spherical lens 201d and reflected back along its path by mirror 205. By the time it reaches the beam splitter 203, the reference light travelled close to the same optical path length as the sample arm light did. At the beam splitter 203 light reflected back from the reference arm and light backscattered by the sample are recombined and coherently interfere. The recombined light is then directed towards a 1D detector 206 after passing through a spherical lens 201e. In the line-field holoscopy system illustrated here, the line of light on the line detector 206 is significantly defocused along the line. The additional astigmatism is introduced by a cylindrical lens 202b in the detection path as described in US Patent Publication No. 2014/0028974 Tumlinson et al. "Line-field Holoscopy" hereby incorporated by reference. In general, the detector position of the 1D detector in a line-field holoscopy system may correspond to a conjugate plane of the sample, a conjugate plane of the pupil, or a position corresponding to a plane in between the two afore mentioned planes.

The electrical signals from the 1D detector 206 are transferred to the processor 209 via a cable 207. The processor 209 may contain a field-programmable gate array (FPGA) 208, or any other type of parallel processor well known to one skilled in the art, which performs some, or the entire holoscopy signal processing steps, prior to passing the data on to the host processor 209. The processor is operably attached to a display 210 for displaying images of the data. The interferometer could consist of bulk-optics, photonic integrated circuits, fiber-optics or hybrid bulk-optic systems and could have different architectures such as Michelson, Mach-Zehnder or common-path based designs as would be known by those skilled in the art. Alternative holoscopy interferometer configurations involving the use of planar waveguides are described in PCT Publication WO 2015/052071 hereby incorporated by reference.

Similar to full-field systems, line field swept-source interferometric systems typically acquire multiple A-scans in parallel, by illuminating the sample with a line and detecting the backscattered light with a 1D detector. Unlike full-field, in order to acquire a volume, the line of light on the sample is scanned across the sample using a 1-axis scanner 220 and multiple spatially separated cross-sections are acquired. While the tunable laser sweeps through its optical frequencies, several hundred line acquisitions are required in order to be able to reconstruct a cross-section with a reasonable depth (>500 µm) and resolution.

Details of the processing carried out on the signals for the holoscopy systems illustrated in FIGS. 1 and 2 will now be considered. In typical holoscopy systems, the detected light fields are sampled linearly in x and y as a function of optical wavenumber k, with $k=2\pi/\lambda$, for the case where the detector is placed at a conjugate plane of the sample, and linearly in $k_x$ and $k_y$ as a function of optical wavenumber k, for the case where the detector is placed at a conjugate plane of the pupil. Wolf recognized that the three-dimensional distribution of the scattering potential of the object can be computationally reconstructed from the distribution of amplitude and phase of the light scattered by the object (Wolf, E., Opt. Commun. 1, 153-156, 1969). The so-called Fourier diffraction theorem, relates the Fourier transform of the acquired scattering data with the Fourier transform of the sample's structure. A correct, spatially invariant volume reconstruction by a 3D Fourier transform of the acquired scattering data is only obtained if the acquired data $k_x$ and $k_y$ are sampled on a rectangular lattice $\{k_x, k_y, k_z\}$. Holoscopy systems however generate spatial frequency domain samples over circular arcs (Kak, A. C. et al., Principles of Computerized Tomographic Imaging 1988):

$$k_z = \sqrt{k^2 - k_x^2 - k_y^2}$$

It is therefore necessary to apply an interpolation in the frequency domain in order to resample the acquired data from being uniformly sampled in $\{k_x, k_y, k\}$ to be uniformly sampled in $\{k_x, k_y, k_z\}$ prior to the 3D Fourier transform (Kak, A. C. et al., Principles of Computerized Tomographic Imaging 1988). In optical coherence tomography the resampling in the spatial frequency domain is skipped (Fercher, A. F., J. Biomed. Opt. 1, 157-73, 1996). Not resampling the data in the spatial frequency domain to the proper lattice results in reconstructions with out of focus blurring.

Prior to the resampling step, the acquired data is transformed to the spatial frequency domain using a 2D Fourier transform (FT). Note, if the data was acquired in the spatial frequency domain (detector position corresponds to a conjugate plane of the pupil) one can skip this step. For an efficient implementation of the FT one would likely make use of the fast Fourier transform (FFT), which is why we will from here on use the term FFT interchangeably with the term FT. Someone skilled in the art can further recognize that one may alternatively choose to use other transforms to transform signals between the spatial domain (or time domain) and the frequency domain, such as wavelet transforms, chirplet transforms, fractional Fourier transforms, etc. In the spatial frequency domain, the measured field at each optical frequency is then computationally propagated to the reference plane. Note, this step can be skipped in case the detector is placed at a conjugate plane of the sample and the optical path length difference between the focal position in the sample arm and the reference mirror is matched, i.e. the focal position corresponds to the zero-delay position. One then applies the above mentioned resampling in order to obtain data uniformly sampled in $\{k_x, k_y, k_z\}$. This now allows applying a 3D FFT to transform the data from the frequency domain to the spatial domain and therefore obtain a 3D representation of the sample's scattering potential with spatially invariant resolution.

Alternative reconstruction techniques, which can be used to obtain similar results were described for example by Ralston et al. (Ralston, T. S. et al., Opt. Lett. 31, 3585, 2006), Nakamura et al. (Nakamura, Y. et al., Jpn. J. Appl. Phys. 46, 1774-1778, 2007) and Kumar et al. (Kumar, A. et al., Opt. Express 21, 10850-66, 2013; Kumar, A. et al., Opt. Express 22, 16061-78, 2014) and US Patent Publication No. 2014/0218684.

Note, especially in reconstruction methods, where the sampling in the spatial frequency domain is corrected by the application of a phase filter in the $\{k_x, k_y, z\}$-space, this phase filtering step can be skipped for the plane corresponding to the optical focal plane (Kumar, A. et al., Opt. Express 21, 10850-66, 2013; Kumar, A. et al., Opt. Express 22, 16061-78, 2014).

A prerequisite for a successful holoscopic reconstruction is the availability of angle diverse scattering information. In holoscopy systems a dense spatial sampling typically ensures that light for each point within the FOV is captured from multiple angles. In full-field systems this is realized by employing a vast number of photosensitive elements, in line-field or point-scanning systems this is typically realized by overlapping adjacent line or point acquisitions.

II. Partial Field Frequency-Domain Interferometric Imaging

So far point scanning, multi-point scanning, line-field, and full-field interferometric imaging systems have been used to create 3D representations of the human retina. While in point-scanning systems and multi-point scanning systems the field of view (FOV) is typically scanned transversely in X and Y and detected at one or multiple points, the FOV in line-field systems has so far only been scanned perpendicular to the line, and full field systems have not employed a scanner at all. The reduced system cost and complexity due to the lack of scanners suggests in principle an advantage of full-field imaging methods over scanning methods. However, for in-vivo holoscopic 3D imaging, one typically needs to acquire ideally more than 500 2D images with different wavelengths in order to be able to reconstruct the 3D depth information over a reasonable depth (>500 µm). In the case of imaging living tissue, involuntary motion or the blood flow may introduce significant artifacts if these images are not acquired with sufficiently fast sweep rates.

Figure 3A:
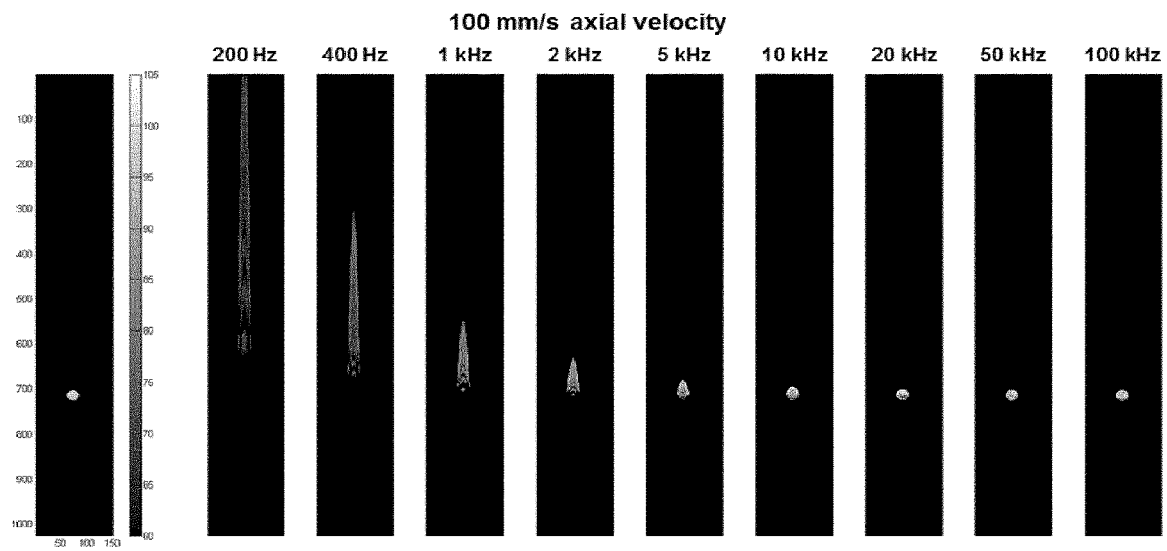
FIG. 3A shows a simulation of motion artifacts caused by a blood vessel with 100 mm/s axial flow speed for sweep rates ranging from 200 Hz to 100 kHz.

To illustrate the impact of motion on the image quality at different imaging speeds, we simulated in FIG. 3A, the expected motion artifacts caused by a blood vessel with 100 mm/s axial flow speed for sweep rates from 200 Hz to 100 kHz. In the most left image of FIG. 3A we see a simulated B-scan of a vessel with 100 mm/s axial flow velocity, imaged with an infinitely fast OCT system, i.e. an artifact free image. In the images to the right, for 200 Hz to 100 kHz sweep rates, one can observe what impact the axial motion has on systems with limited sweep speed. Especially up to 10 kHz one can notice two effects: an axial position shift, caused by a Doppler shift, as well as a broadening of the axial point spread function (PSF). The broadening of the axial PSF has the secondary effect of reduced signal intensity, because the energy is spread over a larger area. The color bar indicates the logarithmically scaled intensity for the motion artifact free image as well as the images on the right.

While 100 mm/s axial motion represents an extreme case, it illustrates the need for relatively high sweep rates. For instance, in order to acquire 500 wavelengths per sweep at a sweep rate of 10 kHz, a full-field system would require a 2D detector with a frame rate of 5 MHz with a sufficient number of photosensitive elements to appropriately sample the full FOV (e.g. at least 512×512 photosensitive elements). Cameras capable of achieving such frame rates with a sufficiently high number of photosensitive elements are, to the best of our knowledge, so far not commercially available, and would likely be highly expensive if they were to become available because of the resulting data rate requirement. Using the example above of a detector with 512×512 photosensitive elements and a frame rate of 5 MHz would result in a sample rate of 512×512×5 MHz=1.31 THz. With a bit depth of 12 bit per sample, this would correspond to 1.97 TB/s.

Figure 3B:
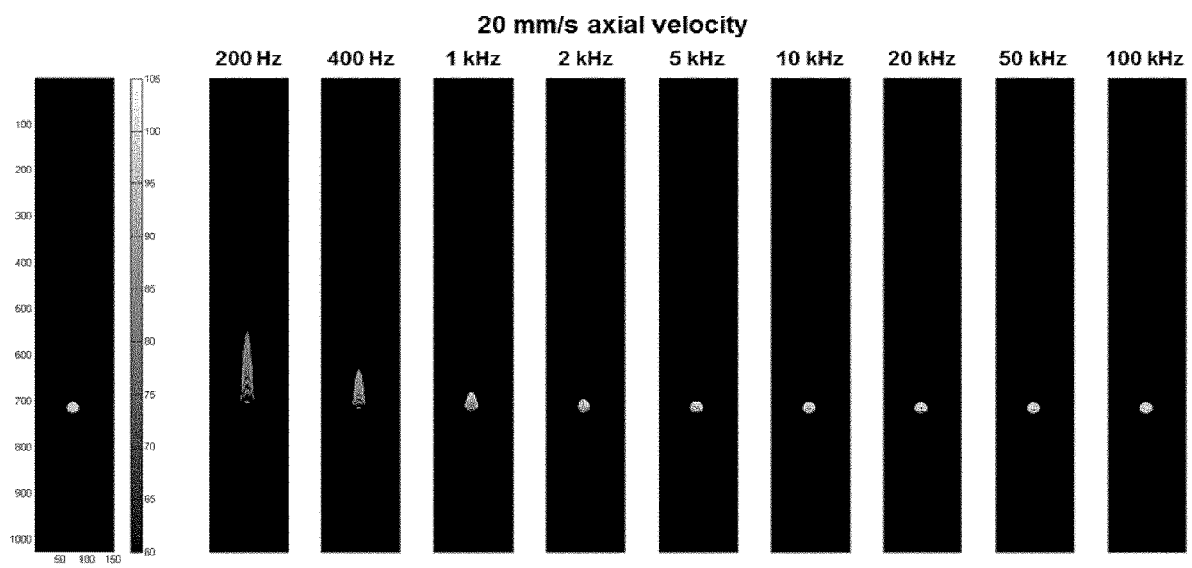
FIG. 3B shows a simulation of motion artifacts caused by a blood vessel with 20 mm/s axial flow speed for sweep rates ranging from 200 Hz to 100 kHz.

To illustrate the impact of slower axial velocities, we simulated in FIG. 3B, the impact of a blood vessel with an axial velocity of 20 mm/s FIG. 3B is of the same format as FIG. 3A, with an artifact free image on the left side, and a series of simulated images representing data collected at different sweep rates ranging from 200 Hz to 100 KHz proceeding from left to right. It can be recognized that even in this case sweep rates below 2 kHz can cause significant motion artifacts. Using the same specification as above, one would in order to acquire 500 wavelength samples per sweep, require a detector with a frame rate of at least 1 MHz. Even though the minimum frame rate is in this case significantly reduced, we are not aware of a commercially available detector which can reach such frame rates with a sufficiently large number of photosensitive elements (e.g. 512×512). The data rate of such a detector with 512×512 photosensitive elements, 1 MHz frame rate, and 12 bit per sample would still correspond to 393.2 GB/s data rate, which is not manageable with today's consumer grade computers.

We therefore describe herein partial-field interferometric imaging systems using a spatially resolved detector with fewer photosensitive elements, with which it is generally easier to achieve higher frame rates. Because the number of photosensitive elements on the detector correlates with the resolution and/or FOV on the sample, in a partial field system, one would reduce the FOV and scan this FOV transversely across the sample. In a similar fashion, a line of light can be scanned not only in the direction perpendicular to the line as in traditional line field systems, but also in the direction along the line, in order to increase the FOV. Different ways of how to scan the FOV of a partial-field or a line-field system are described under "Scanning of a two-dimensional area or line in X&Y." While the embodiments described herein are focused on swept-source systems employing a tunable laser, the concepts would also apply to spectral domain interferometric imaging systems.

If one reduces the number of photosensitive elements relative to the roughly 250,000 elements of a full-field system to for example to 2500, which could for example be arranged in a 50×50 configuration, the data rate for a detector with 1 MHz and 12 bit per sample, would be 3.75 GB/s. Such a data rate can be transferred and processed in real time with today's standard data transfer interfaces (e.g. PCIe, CoaXpress, etc.) and a consumer grade personal computer (PC). Bonin et al. reduced the number of pixels, which were read out by the camera of their Fourier-domain full-field OCT system from 1024×1024 pixels to 640×24 pixels, in order to increase the camera frame rate for in-vivo imaging (Bonin, T. et al., Opt. Lett. 35, 3432-4, 2010). This system however did not contain any scanners and it was not recognized that the FOV could be regained by transverse scanning.

In another preferred embodiment one uses a spatially resolved detector with 7 pixels in a hexagonal arrangement (one photosensitive element in the center, surrounded by 6 photosensitive elements). Such a low number of pixels enable frame rates in the MHz or GHz range, while still enabling the advantages and applications of partial field holoscopy described herein. At such frame rates the sweep rate of the laser can be increased and more frames can be acquired per sweep. This increases the spectral sampling and therefore the imaging depth as well as reduces the impact of sample motion.

Figure 4:
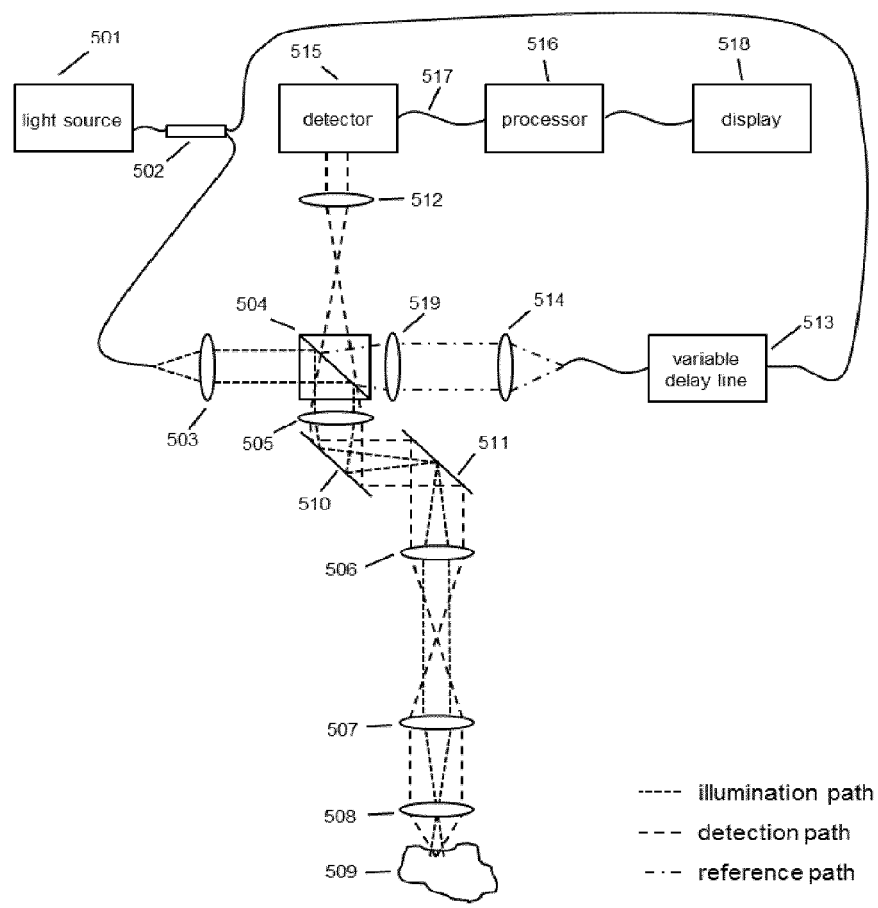
FIG. 4 illustrates one embodiment of a swept-source based partial-field frequency-domain imaging system.

One embodiment of a swept source based partial-field interferometric frequency-domain imaging system according to the present application is illustrated in FIG. 4. A light beam from a tunable light source 501 is split into sample light and reference light by a beam divider, in this case, fused coupler 502. A series of sample optics are used to deliver the light beam in the sample arm to the sample, a light scattering object. First, the sample light is collimated by a spherical lens 503 and reflected towards the sample 509 by a beam splitter 504. A set of spherical lenses, 505, 506, 507, and 508, creates a region of illumination on the sample 509. The region could be a spot, a line or a two-dimensional area. The sample could be any light scattering object, but a common sample is the human eye. The location of the area illumination on the sample is adjusted transversely by scanners 510 and 511. In the detection path (path from sample 509 to the detector 515), light scattered by the sample is detected in a conjugate plane of the pupil of lens 508. A group of return optics are responsible for combining the light scattered from the sample and light from the reference arm and directing the combined light to the spatially resolve detector 515. Lenses 507, 506, 505 and 512 relay the light from the pupil to the spatially resolved detector 515. On this path, the light passes the beamsplitter 504 a second time, where the backscattered sample light and reference light are recombined. At this point, the reference light has travelled through a variable delay line 513 which allows the adjustment of the optical path length difference between the sample and reference light, before it was collimated by a spherical lens 514. Lens 519, in combination with lens 512, creates a planar reference wavefront on the detector 515. Typically the variable delay line 513 is adjusted so that sample and reference light travel close to the same optical distance before they coincide on the spatially resolved detector 515. The combined light is collected at each scanned location on the object by the detector which generates signals in response thereto.

The electrical signals from the detector 515 are transferred to the processor 516 via a cable 517. The processor 516 may for example contain a field-programmable gate array (FPGA), a digital signal processor (DSP), an application specific integrated circuit (ASIC), a graphic processing unit (GPU), a system on chip (SoC) or a combination thereof, which performs some, or the entire Fourier domain imaging signal processing steps, prior to passing the data on to the host processor, or may be the host processor. The processor generates image data of the object from the detected signals. This could be a direct 3D representation of the light scattering object in the case of OCT or it could involve the holoscopic reconstruction steps outlined in the section "System Descriptions" with further enhancements described in the section entitled "Reconstruction and Computational Adaptive Optics" to create a 3D representation of the object having a spatially invariant resolution. The processor can be operably attached to a display 518 for displaying images of the data. The sample and reference arms in the interferometer could consist of bulk-optics, photonic integrated circuits, fiber-optics or hybrid bulk-optic systems and could have different architectures such as Michelson, Mach-Zehnder or common-path based designs as would be known by those skilled in the art. While a transmissive delay line is shown in FIG. 4, those skilled in the art would appreciate that a reflective delay line could also be used. Cable 517 could be replaced with a wireless data transmission.

Unlike prior art systems, partial-field interferometric imaging systems as described herein acquire several A-scans in parallel, by scanning the sample with a spot, line or two-dimensional area and detecting the backscattered light with a spatially resolved detector. For swept-source systems as illustrated in FIG. 4, while the tunable laser sweeps through its optical frequencies, several hundred detector acquisitions are required in order to be able to reconstruct a volume with a reasonable depth (>500 µm) and resolution. In the case of FIG. 4, in order to acquire a volume, the illumination area on the sample is scanned across the sample using two 1-axis scanners 510 and 511 and multiple spatially separated, but possibly overlapping, volumes are acquired. Alternatively a single 2-axis scanner could be used to fulfill the task of the two 1-axis scanners, all or a portion of the optical components of the system could be rotated relative to the sample, or the sample could be moved transversely relative to the system instead of steering the illumination across the sample using scanners. Other alternative embodiments of spatially scanning the 2D illumination are described under the section entitled "Scanning related improvements."

Partial field interferometric systems have the advantage compared to multi-beam systems, that they can easily be implemented with a single bulk optics interferometer, as illustrated in FIG. 4 and described above. Multi-beam systems on the other hand rely on dedicated interferometers for each parallel detection channel and couple the light backscattered by the sample into a dedicated single mode fiber for each parallel detection channel (Wieser, W. et al., Opt. Express 18, 14685-704, 2010; Potsaid, B. et al., Opt. Express 18, 20029-48, 2010; Klein, T. et al., Biomed. Opt. Express 4, 619-34, 2013; Werkmeister, R. M. et al., Opt. Lett. 33, 2967, 2008).

The use of single-mode fibers in multi-beam systems also limits the collection efficiency of the system when compared to directly illuminating photosensitive elements. This concept is schematically illustrated in FIG. 18. In FIG. 18A, reference and sample light are incident on an array of lenses that couple the light into a set of single-mode fibers. The fibers then deliver the light to a set of photosensitive elements. The Gaussian collection efficiency of these fibers is shown as a dashed line. In terms of light collection, given strong enough reference light, FIG. 18A can be seen as equivalent to the case where individual fiber interferometers are used for each collection fiber. FIGS. 18B and 18C then show cases where reference and sample light directly illuminate the set of photosensitive elements. In FIG. 18B, single-mode fibers are not used and the reference beam intensity has assumed Gaussian profiles. In this case, the reference light profiles are the same as the collection efficiency profiles in FIG. 18A, but the photosensitive elements have a uniform spatial collection efficiency. As the amount of reference light away from the center of the photosensitive elements is low compared to the center, the interference with the sample light incident upon the detectors away from their center is reduced, therefore reducing the effective collection efficiency of this light. Thus, if one provides a uniform reference intensity as shown in FIG. 18C, the overall collection efficiency of the system can be improved as compared to FIG. 18A and FIG. 18B. Finally, FIG. 18D shows a configuration where light is optically coupled to the photosensitive elements via multi-mode fibers. These fibers would again have a more uniform collection efficiency as compared to single-mode fibers.

Figure 5:
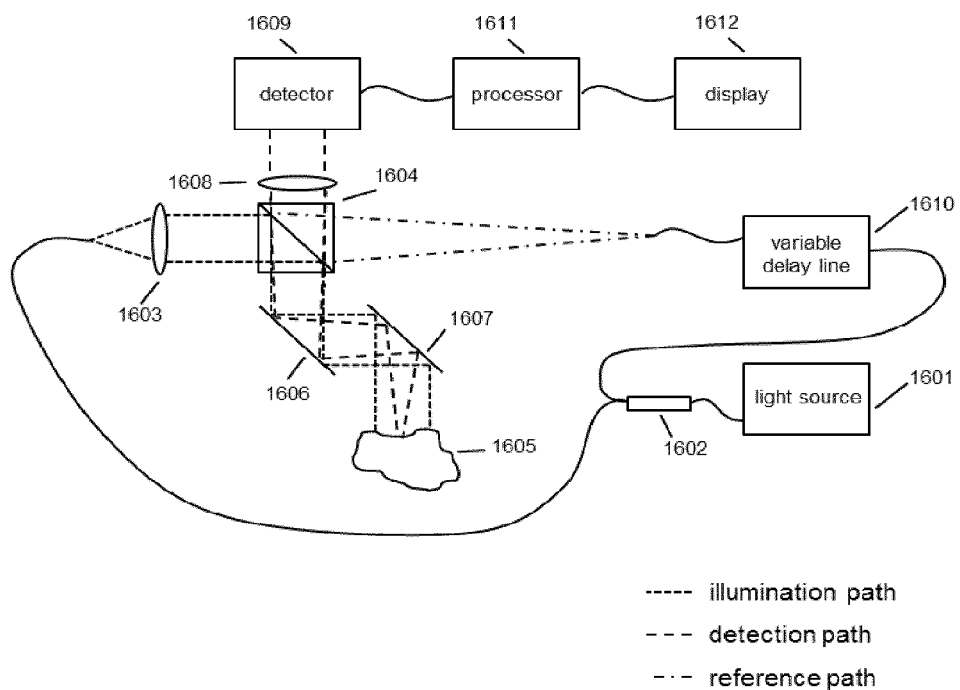
FIG. 5 illustrates one embodiment of a swept-source based partial-field frequency-domain imaging system with collimated sample illumination.

In the described exemplary partial field interferometric imaging implementation shown in FIG. 4, the sample is illuminated with a diverging beam. The light incident on the sample can, however, also be converging or be collimated. An exemplary partial field implementation with a collimated sample illumination is schematically illustrated in FIG. 5. The light from a light source 1601 is split into reference and sample light by a fused fiber coupler 1602. Light in the sample path or arm passes through collimating lens 1603 to create a collimated beam, which is reflected by beam splitter 1604, before it illuminates an area on the sample 1605. Similar to FIG. 4, the area could be a spot, a line or a two-dimensional area. The location of the beam on the sample can be adjusted by scanners 1606 and 1607. The sample light is then backscattered by the sample 1605 and recombined with the reference light at the beam splitter 1604, where they coherently interfere and the interfering light travels along the detection path to the spatially resolved detector 1609. Prior to being combined with the backscattered light, the reference light passes through a variable delay line 1610, which allows the adjustment of the optical path length difference between reference and sample light. A lens 1608 places the detector 1609 in a pupil plane (far field of the sample) and creates a flat reference wavefront. Similar to the other embodiments, the output from the detector is supplied to a processor 1611. The processor can generate image data of the sample based on the output from the detector. The resulting images can be stored in the processor or displayed on a display 1612. The processing functions may be localized within the instrument or functions may be performed on an external processing unit to which the collected data is transferred. This unit could be dedicated to data processing or perform other tasks which are quite general and not dedicated to the imaging device. A data processing system may consist of one or more processors, not necessarily located in close proximity to one another, and associated peripherals such as displays. One or more of the processors can be of the parallel processing type such as GPUs, FPGAs, or multi-core processors.

While in the above described embodiments, the detector is placed at a position corresponding to the pupil plane or a conjugate plane of the pupil, a partial field system has several options for the imaging relationship between the sample and the detector. The detector can be placed at a position corresponding to a conjugate plane of the sample, or the detector could be placed at a position corresponding to an intermediate plane between a sample conjugate plane and pupil conjugate plane.

A smaller FOV on the sample and smaller number of photosensitive elements may lead in some cases to a higher confocality compared to a full field system. While this has significant advantages with respect to the suppression of multiply scattered light, it also reduces the depth of field (DOF) for an individual partial field acquisition. The concept of a partial field system as described above is however to acquire multiple adjacent or overlapping partial-fields in order to build up the full FOV. Therefore light from multiple angles is captured for each sample point and out of focus light which was not detected in one partial field acquisition will be picked up by one or more of the adjacent partial field acquisitions. If one then applies a holoscopic reconstruction not individually to a single partial field acquisition, but rather combining multiple adjacent partial field acquisitions prior to the reconstruction, one is able to also correct for the out of focus resolution loss in any depth plane. The out of focus signal loss in a partial field system is therefore solely defined by the NA of the illumination. With an illumination NA of 0 (illumination by a perfectly collimated beam of light), one is theoretically able to create volumes with an infinite DOF (spatially invariant transverse resolution and no out of focus signal loss). It is therefore desirable to combine a low NA illumination with a large NA detection in order to maximize the DOF, collection efficiency and transverse resolution. The number of photosensitive elements on the detector however, has to support the desired resolution and FOV, and should be chosen accordingly. In cases where the number of photosensitive elements on the detector is too low to support at least Nyquist sampling, adjacent partial fields can be placed in a manner that they partially overlap each other.

In full-field systems, the practical imaging depth and the FOV over which one is able to reconstruct a volume with spatially invariant resolution, can be limited by vignetting introduced by the optics in the detection path (Marks, D. L. et al., J. Opt. Soc. Am. A 24, 1034, 2007). Because the size of an instantaneous FOV in a partial field system is typically smaller, and two or more smaller adjacent FOVs are combined for the reconstruction of the full volume, the effects of vignetting are eliminated or greatly reduced. This enables a larger volume over which a spatially invariant resolution can be obtained which is why it is particularly well suited for wide field and large depth imaging.

With the help of zoom optics in the sample arm, one can change the magnification and thereby trade-off resolution for FOV by changing the area of the illumination field on the sample as well as the magnification of the sample or pupil plane on the way to the detector. One preferred embodiment is using adaptive optics, such as fluidic adaptive lenses (Zhang, D.-Y. et al., Opt. Lett. 29, 2855, 2004) to implement a variable magnification of the imaging system. With adaptive lenses one is able to change the magnification of the imaging system by varying the focal length of the lenses instead of the distance between the lenses. This enables more compact systems and allows switching the magnification significantly quicker than with traditional zoom optics, where often times three or more lenses have to be translated over several centimeters.

Partial field systems are a cross between full-field and point scanning systems, which can vary in their degree of parallelism. The configuration closest to the full-field case would be a partial-field system where the full FOV is obtained by only four spatially displaced parallel volume acquisitions (2×2). The configuration closest to the point-scanning case would be a partial-field system, where the full FOV is build up by several displaced acquisitions with a spatially resolved detector containing two photosensitive elements. In the broadest sense a partial-field frequency-domain imaging system can be characterized as an interferometric frequency domain system, which scans a light beam across a sample in two dimensions and collects the light backscattered from the sample using a spatially resolved detector. In order to be able to support an increase in detection NA without losing the above described advantages of depth invariant resolution and absence of out of focus intensity loss in a system with as little as 2×2 photosensitive elements, one would scan the illumination across the sample in a manner that would create an oversampling (each scatterer of the sample is effectively sampled at least twice). Convenient ways to generate an appropriate oversampling through scanning of a partial field are described under the section entitled "Scanning related improvements".

Figure 6:
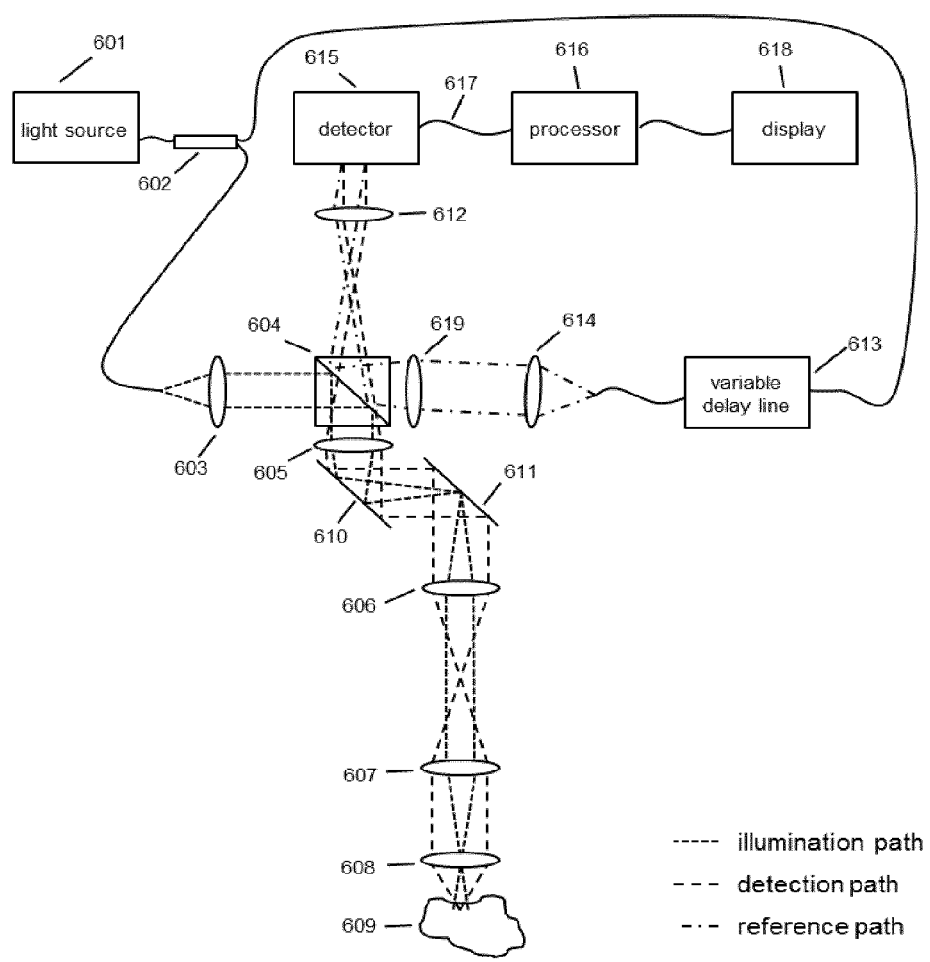
FIG. 6 illustrates one embodiment of an off-axis partial-field frequency-domain imaging system.

The field illumination systems so far described herein are in-line embodiments, where the sample light and reference light propagate on the same optical axis. However, field illumination systems have the advantage of a spatially resolved detector, which enables an off-axis configuration of reference and sample arm and therefore the filtering of the mirror image, DC, and autocorrelation terms in the spatial frequency domain (Cuche, E. et al., Appl. Opt. 39, 4070, 2000; Pavillon, N. et al., Appl. Opt. 48, H186-95, 2009). FIG. 6 schematically illustrates one embodiment of an off-axis partial field system, where reference and sample light illuminate the detector 615 under different angles as indicated by the separate light paths of the two beams between the beam splitter 604 and detector 615.

In FIG. 6, light from a tunable light source 601 is split into sample light and reference light by a fused coupler 602. The sample light is collimated by a spherical lens 603 and reflected towards the sample 609 by a beam splitter 604. A set of spherical lenses 605, 606, 607, and 608 creates an area illumination on the sample 609. The location of this area illumination on the sample can be adjusted transversely by scanners 610 and 611. In the detection path (path from sample 609 to the detector 615), the light backscattered by the sample is detected in a conjugate plane of the pupil of lens 608. Lenses 607, 606, 605 and 612 relay the light from the pupil to the spatially resolved detector 615. On this path, the light passes the beamsplitter 604 a second time, where backscattered sample light and reference light are recombined. At this point, the reference light has travelled through a variable delay line 613 which allows the adjustment of the optical path length difference between the sample and reference light, before it was collimated by a spherical lens 614. In this embodiment the off-axis illumination is achieved by rotating the collimation lens 614. Lens 619, in combination with lens 612, creates a planar, but tilted reference wavefront on the detector 615. Typically the variable delay line 613 is adjusted so that sample and reference light travel close to the same optical distance before they coincide on the detector 615, where they coherently interfere. Due to the tilted reference wavefront, lateral interference fringes are created across the detector 615.

The electrical signals from the detector 615 are transferred to the processor 616 via a cable 617. The processor 616 may for example contain a field-programmable gate array (FPGA), a digital signal processor (DSP), an application specific integrated circuit (ASIC), a graphic processing unit (GPU), a system on chip (SoC) or a combination thereof, which performs some, or the entire Fourier domain imaging signal processing steps, prior to passing the data on to the host processor. The processor is operably attached to a display 618 for displaying images of the data. The sample and reference arms in the interferometer could consist of bulk-optics, photonic integrated circuits, fiber-optics or hybrid bulk-optic systems and could have different architectures such as Michelson, Mach-Zehnder or common-path based designs as would be known by those skilled in the art. While a transmissive delay line is shown in FIG. 6, those skilled in the art would appreciate that a reflective delay line could also be used.

Note that by introducing an angle between the reference and sample arms, one creates interference fringes at higher spatial frequencies than those in the image itself, thus requiring higher resolution detection in the dimension in which the angle was introduced. This increases the number of required photosensitive elements in the direction of the off-axis illumination by at least a factor of two for minor image and DC term elimination, assuming that the transverse resolution and the width of imaging on the tissue is kept constant. A somewhat higher spatial count of photosensitive elements is required if one wishes to also suppress the auto-correlation term. This further increase can however be minimized or avoided by applying a non-linear spatial frequency filter as for example described for full-field digital holography by Pavillon et al. (Pavillon, N. et al., Appl. Opt. 48, H186-95, 2009). Instead of having a higher number of photosensitive elements in one dimension, one can reduce the spatial extent of the partial field in the direction of the off-axis imaging. In some cases it may be desirable to use a detector with rectangular photosensitive elements, resulting in a spatially resolved detector with different spatial resolution in the two dimensions. Alternatively it may be desirable to magnify the image in the x direction relative to the y direction so as to reduce the spatial frequency of the fringes (and image structure) in the direction of the magnification.

In the following we describe preferred detector configurations for off-axis embodiments of partial field frequency-domain imaging systems for different imaging relationships between the sample and the detector:

1) Detector Placed at a Position Corresponding to a Conjugate Plane of the Pupil
   a. Symmetric FOV—photosensitive elements should be significantly narrower (at least 1.5×, typically 2-3×) in the off-axis dimension relative to the other dimension in order to support high spatial frequencies generated by the off-axis illumination. Note, this could also be achieved by magnifying the pupil in the dimension of the off-axis illumination on the way to the detector or by demagnifying the pupil in the dimension perpendicular to the off-axis illumination on the way to the detector.
   b. FOV significantly longer (at least 1.5×, typically 2-3×) in the dimension perpendicular to the off-axis illumination—photosensitive elements would typically be square, although depending on the ratio of the dimensions, rectangular ones could also be used.

2) Detector Placed at a Position Corresponding to a Conjugate Plane of the Sample
   a. Symmetric transverse resolution—photosensitive elements should be significantly narrower (at least 1.5×, typically 2-3×) in the off-axis dimension relative to the other dimension in order to support high spatial frequencies generated by the off-axis illumination. Note, this could also be achieved by magnifying the FOV in the dimension of the off-axis illumination on the way to the detector or by demagnifying the FOV in the dimension perpendicular to the off-axis illumination on the way to the detector.
   b. Resolution significantly lower (at least 1.5×, typically 2-3×) in the dimension of the off-axis illumination—one would typically use square photosensitive elements and reduced numerical aperture in the direction of the off-axis illumination, although depending on the relative dimensions, rectangular ones could also be used.

In general an off-axis partial field system can, just like an in-line partial field system, employ a detector with equal numbers of photosensitive elements in both dimensions, different numbers of photosensitive elements in the two dimensions, or configurations of photosensitive elements which are not a square or rectangle (e.g. hexagonal, octagonal, or circular configurations to just mention a few examples). Further the detector employed in an off-axis partial field system can, just like the detector employed in an in-line partial field system, contain square, rectangular, hexagonal, diamond, circular or arbitrarily shaped photosensitive elements.

Rectangular photosensitive elements may be beneficial regardless of whether one chooses an off-axis or an in-line configuration. One example is a partial-field system with a rectangular illumination area. To illustrate the possible difficulties arising from a detector with square photosensitive elements in such a system, we here give an example of a partial-field system in which a detector containing 128×8 photosensitive elements is placed at a position corresponding to a conjugate plane of the pupil and an area of 4 mm×4 mm in the pupil is supposed to be detected by said detector. The common size of a single photosensitive element in a high speed detector is 7 um×7 um, resulting in a detector size of 896 um×56 um for the 128×8 detector mentioned above. One can recognize that the image of the pupil has to be minified on the way to the detector by different amounts in both dimensions. This can in principle be realized with cylindrical or astigmatic lenses. In the long dimension the image has to be minified by 4000 um/896 um=4.46, which is a straightforward task. In the other dimension the image of the pupil however has to be minified by 4000 um/56 um=71.4, which is much more difficult and would likely involve a complex optical design. We therefore suggest to use in such cases, a detector with rectangular pixels. The benefit can be illustrated by the same example: The detector has an aspect ratio of 16:1, while the image has an aspect ratio of 1:1. The use of a detector, where each photosensitive element has an aspect ratio of 1:16, would result in a detector with an aspect ratio of 1:1, albeit with different resolution in the two dimensions. With such a detector one can avoid the use of cylindrical optics, because the image can now be minified identically in both dimensions. In order to limit the demagnification factor, one would ideally choose to increase the size of the photosensitive elements in one dimension instead of reducing the size in the other dimension. While one would ideally choose to use a detector with an aspect ratio that corresponds to the aspect ratio of the area to be imaged as described above, it may already be beneficial to increase the size of the photosensitive elements with the goal to increase the image size on the detector, regardless of the aspect ratio.

III. Scanning Related Improvements

Point-scanning systems scan a spot across the sample in two-dimensions at very high speeds (e.g. 1200 mm/s). To do so reliably without creating image distortions or wearing out the scanner motors, one usually chooses to use a pair of galvanometric scanners. Due to the parallel detection of multiple points on the sample simultaneously, line- and partial-field systems typically do not need to scan the illumination field across the sample as fast as point scanning systems. The requirements on the scanners in line- and partial-field systems, are therefore significantly relaxed. This enables the use of non-galvanometric 1-axis and multi-axis scanners, such as polygon mirror scanners, electric motor scanners, piezoelectric scanners, magnetostrictive mirrors, electrostatic scanners, MEMS scanners, electro optic deflectors, acousto-optic deflectors, phased-arrays, etc. The scanning of a partial field, may however have significant implications on the data acquisition and reconstruction methods.

a. Scanning of a Two-Dimensional Area or Line in X&Y

As previously described, in order to complete a full volume acquisition in a line-field system, the line of a line field image has been traditionally scanned in the dimension perpendicular to the line. Here it is described how a line of light can also be scanned in the direction along the line in order to increase the FOV in this dimension. While a small volume could be acquired with a partial field illumination without transverse scanning, in the partial field systems described herein, the partial field is scanned in both lateral dimensions in order to capture a full volume with a reasonable FOV. There are several ways to realize two-dimensional scanning of a line of two-dimensional area as will now be described.

The scanning can be realized "step wise", where an entire sweep of the frequencies of the source is acquired at a fixed position on the sample, before the scanners move the illumination and detection field to the next adjacent position, where again an entire sweep is acquired at the same position. This scan mode puts a high strain on the scanners during the transitions between positions. The transitions also cause "dead-times", because one isn't able to acquire meaningful data during the transitions. The fast scanner movement during the transition and the abrupt stop may also cause the scanner to oscillate and therefore require a certain settling time before the start of the acquisition at the new position, effectively increasing the dead-time. In order to minimize the oscillations one can chose to slow the scanner down more smoothly, e.g. by a sinusoidal velocity curve.

An alternative scanning mode, which significantly reduces the strain on the scanners, would be a "continuous" scan mode, which is also known from point scanning OCT. In this case the scanners are continuously moving, avoiding abrupt accelerations and stops. To make this scan mode work for line- and partial-field scanning, adjustment to the data acquisition and/or processing are required. I.e. in order to obtain the full axial resolution the spectral information for each lateral point has to be resorted according to the apparent motion occurring during one sweep. The continuous scan mode can further be distinguished in a "continuous-fast" scan mode, a "continuous-averaging" scan mode, and a "continuous multi-acquisition" scan mode.

The preferred embodiment for the majority of applications is the "continuous-fast" scan mode. Here the field (partial or line) would be displaced laterally by up to one resolution point during one Nth of the time of one sweep, where N is the number of photosensitive elements in the scanning direction. In this mode one would collect fewer wavenumber samples around the edges of the FOV, which would result in lower axial resolution in these regions. The full axial resolution would be reached after a number, N, A-scans from the edge. Various approaches could be used to address this loss of resolution at the edges; for example scanning beyond the desired FOV, parking the scanner for a sweep at the edge of the scan, etc.

Because in the continuous-fast scan mode, different parts of the sweep of a single location are acquired by different photosensitive elements, special care has to be taken for the image reconstruction, i.e., the data has to be rearranged or resorted in order to produce continuous spectral fringe signals for each location. FIG. 7 shows a schematic which illustrates the order in which the data is acquired and how it should be grouped for reconstruction in continuous fast scanning. The Roman numerals indicate sections of the sweep. In this example each sweep is divided into 8 sections. One section can contain a single wavenumber sample or a range of wavenumber samples. The Arabic numerals indicate the pixel numbers of the detector. To keep this illustration simple, we chose to use for this example a 1D detector, but the basic concept extends to 2D detectors. The line on the sample would be continuously scanned along the direction of the line. The dashed boxes indicate how the samples should be grouped for processing. One can recognize that the initial 7 A-scans along the scan direction do not contain all the sweep sections and therefore do not contain the entire spectral information. These A-scans would have reduced axial resolution. The first A-scan with full axial resolution consists of I.8, II.7, III.6, IV.5, V.4, VI.3, VII.2, VIII.1; the second A-scan with full axial resolution consists of II.8, III.7, IV.6, V.5, VI.4, VII.3, VIII.2, I.1; the third A-scan with full axial resolution consists of III.8, IV.7, V.6, VI.5, VII.4, VIII.3, I.2, II.1; and so on. One can further recognize that also at the end of the scan one obtains 7 A-scans with reduced axial resolution, similar to the A-scans at the start of the scan.

The maximum scan speed is defined by two requirements:
1. In order to avoid phase-washout in the continuous-fast scan mode, the displacement during each individual frame acquisition of the detector should not exceed one resolution point.
2. In order to avoid varying axial resolution throughout the FOV (not including the above described effects at the edges), the displacement during one sweep should not exceed one partial-field size.

An alternative embodiment is the "continuous averaging" mode, in which the field is continuously scanned and displaced by not more than one resolution point within the time frame of one sweep. This mode creates (M*N(N+1)/2)–M*N additional A-scans per displacement by one partial field size, when scanned in one direction, with N being the number of photosensitive elements in the scanning direction and M the number of photosensitive elements in the direction perpendicular to the scanning direction. The additional A-scans would most likely be averaged with A-scans acquired at a similar transverse position. We therefore chose to call it "continuous-averaging" mode. The number of additional A-scans quickly becomes very large with increasing number of photosensitive elements, which is why this mode is less practical for most applications compared to the "continuous-fast" mode.

Another alternative embodiment is the "continuous multi-acquisition" mode, in which the field is continuously scanned, and displaced by one Mth of the partial field width within the time frame of one sweep. This mode creates M copies of each A-scan acquired sequentially in time, which could either be averaged or used for generating motion contrast images.

A continuous scan mode and a step wise scan mode would typically be used in conjunction in the case of two-axis scanning. In a preferred embodiment, one would choose to continuously scan in one direction, while scanning stepwise in the other direction. Note that if the step-wise scanning axis is slightly rotated relative to the continuous scanning direction, the slow scanner may be moving continuously as the step is created by the fast scanner returning to its scan start position. In an alternative embodiment, one could choose to continuously scan in both directions in order to create arbitrary scans.

b. Creating a Spatial Oversampling Through Scanning

As mentioned previously, it may in some cases be desirable to design the system in a way that the optical resolution of the system is higher than the resolution defined by the detector. A system employing a 2×2 or a 3×3 detector may, for example, be desirable due to the relative simplicity compared to systems with larger number of photosensitive elements. A 2×2 array system, where adjacent acquisition fields are placed right next to each other, and a FOV of two resolution elements is imaged, provides all the above mentioned partial field advantages. That is, an increase of NA would not lead to an increase in resolution because it would not be supported by the sampling density. It would further suffer from out of focus intensity loss in the detection because the sampling would be too sparse. Insufficient resolution of the detector can however be compensated by only shifting the illumination during the timeframe of one sweep by a distance that corresponds to less than one photosensitive element on the detector. This creates a so called oversampling, meaning that each point on the sample is sampled at least twice. This is commonly done by point-scanning systems in order to support the optical resolution. Creating a similar oversampling with a spatially resolved detector is however more complex because, for example, a shift by half the detector resolution does not create an oversampling of ×2. Although it creates a sampling where the sampling resolution is improved by a factor of two, it results in additional samplings at the exact same sample locations, which therefore do not further improve the sampling resolution. Such a sampling can however be useful for phase sensitive methods as for example Doppler OCT or OCT Angiography, where one ideally needs to sample the same sample location twice in order to measure a difference in the signals over time.

To realize a ×2 oversampling, which increases the sampling resolution, one has to alternatingly shift the illumination by half the size of a photosensitive element and twice the size of a photosensitive element. Instead of interleaving these within one scan, the same sampling density can be achieved by repeating two scans, where the displacement between two sweeps corresponds to the size of two photosensitive elements, however with an offset between each scan which corresponds to half the size of a photosensitive element. A ×3 oversampling can be more easily achieved by simply shifting the illumination between sweeps by a distance, which corresponds to the size of a third of one photosensitive element. To realize a ×3 oversampling with a 3×3 detector one has to shift the illumination between sweeps by a distance which corresponds to the size of 1.5 photosensitive elements.

c. Use of DMD in Parallel Frequency-Domain Imaging

The scanning of the light on the sample need not be realized by traditional mechanical scanners. A partial field interferometric imaging system without scanners can be implemented with the help of a digital micro minor device (DMD). A DMD is considered to be a spatial light modulator (SLM). While the system herein described uses a DMD, the method can also be implemented with the help of other types of SLMs, like for example translucent or reflective liquid crystal micro displays in combination with polarizers. DMDs are used in digital light processing (DLP) systems found in projection devices. The DMD is an optical semiconductor with an array of many microscopic minors, which can switch between two mirror positions; an on-position and an off-position, which typically differ by +/−12 degrees of mirror rotation. In the on position, light from the projector's light source is directed through the lens on the screen, making the corresponding projection image pixel appear bright. In the off-position, the light does not reach the projection screen, and therefore leads to a dark pixel. The same concept can be used to illuminate a partial field on the sample. In such a system the DMD would be imaged to the sample. The size of the image of the DMD on the sample would correspond to the maximum FOV. By setting only a certain number of mirrors of the DMD in the on-position, one is able to reduce the size of the illumination on the sample to a limited region of interest (ROI). At this region of interest, one or more wavelength sweeps would be acquired, before the DMD switches the current minors to the off-position and in exchange switches another group of pixels in an on-position, therefore illuminating a different ROI on the sample. Because the light field does not have to be scanned from one position to the next, as described above for mechanical scanning mirrors, it also avoids the above described implications on the reconstruction. Since there are no limitations on which mirrors can be switched on and off at a given time, successive ROIs do not necessarily have to be adjacent to each other. Instead, they could also overlap or be spatially separated. One could therefore envision a system, where only certain spatially separated ROIs of the entire possible FOV are illuminated. One example for such an operation mode would be a blood flow imaging mode, where one would only be interested in imaging certain ROIs where blood vessels are present, potentially with a high repetition rate, while other ROIs where no blood vessels are present are not of interest. Another example for an application of such a mode is to build up the full FOV by non-adjacent successive ROIs including the case where many small disjoint ROIs are illuminated simultaneously and vary over time to cover the full FOV. This may enable higher illumination powers for biological tissue samples, because the heat generated by the current illumination of one ROI may dissipate into surrounding tissue, which is not illuminated directly after the current illumination.

In a DMD based system where the detector is placed at a position which corresponds to a conjugate plane of the sample, the light on the detector moves according to the illumination on the sample. However one can use a detector with a large amount of photosensitive elements, of which only those which are currently illuminated are being read out. In such a system, the entire detector would correspond to the maximum FOV on the sample, or for that matter to the entire DMD. The instantaneously illuminated photosensitive elements of the detector correspond to the instantaneous FOV on the sample or the minors of the DMD in the on-position. Note, in a system where the detector is placed at a position which corresponds to a conjugate plane of the pupil, no changes between a system with mechanical scanners and a DMD frequency-domain imaging system have to be implemented in the detection path. Another advantage is that DMDs are, compared to galvanometric scanners, significantly cheaper and may enable significantly smaller system designs.

The drawback of a DMD based frequency-domain imaging system is that one likely requires a more powerful light source, because the entire DMD would be illuminated at all times, while only a portion of this light reaches the sample. With advances in light source technology this should become a manageable problem. One solution for this problem is to use a light source array in combination or instead of a DMD in order to illuminate arbitrary parts of the sample, which is described further in the section entitled "Illumination—Light source arrays."

Another possible embodiment, which addresses the increased illumination power requirement to some extent, is to use a DMD based frequency-domain imaging system in combination with a scanner. For example one can choose to use the above described DMD illumination for the fast "scanning" direction and use "step wise" scanning as described above in the slow scanning direction. Such an embodiment avoids the difficulties inherent to continuous scanning of a partial-field, while minimizing the power requirement, because the illumination area on the DMD no longer corresponds to the entire FOV on the sample. For example, a completely DMD based frequency-domain imaging system with N×M individual partial fields requires approximately a N×M times more powerful light source than a completely scanner based system, where N and M are the numbers of effective individual partial-fields in the fast and slow scanning directions respectively. A frequency-domain imaging system which employs a DMD for the fast scanning direction and a traditional mechanical scanner for the slow scanning direction requires only a N times more powerful light source than a completely scanner based frequency-domain imaging system.

Structured illumination is known to provide a resolution enhancement in microscopy (Dan, D. et al., Sci. Rep. 3, 1116, 2013; Heintzmann, R. et al., 3568, 185-196, 1999; Gustafs son, M. G. L., J. Microsc. 198, 82-87, 2000). A DMD in the illumination path, as described above, may therefore be advantageous in a system which combines multiple imaging modalities, for example holoscopy and a fluorescence imaging modality. In such a configuration, the DMD can be used to create super-resolution (resolution beyond the diffraction limit) fluorescence images by structured illumination (Dan, D. et al., Sci. Rep. 3, 1116, 2013). To create such a super resolution image for example a sinusoidal illumination pattern is used to create Moiré fringes. These fringes contain high spatial frequency information, which can be extracted computationally. The achievable resolution is dependent on the number of acquisitions with different orientations of the sinusoidal illumination pattern. A DMD is therefore well suited for this task, because it enables the illumination with different patterns with very short switching times. This is not only true if it is used to replace the scanner in the holoscopy system, because one can also use a DMD for the sole purpose of creating structured illuminations and implement the scanning with a second device, which could either be a DMD or a scanner.

Further, structured illumination can be used to improve imaging quality in scattering media, where multiple-scattering affects the images in a negative way. Tajahuerce et al. recently published a method based on disorder-assisted single-pixel image-retrieval, which makes it possible to overcome the fundamental limitation imposed by multiple scattering even when imaging through dynamically scattering media (Tajahuerce, E. et al., Opt. Express 22, 16945, 2014).

One challenge in creating structured illumination is the need for the structured illumination to be maintained over a large depth of field and in the presence of aberrations. This can be addressed by using coherence effects to generate the structured illumination, for instance by creating two plane waves entering the sample at an angle relative to one another. This creates a sinusoidal illumination across the sample from the spatially varying constructive and destructive interference.

A DMD can not only be used to adjust the region of illumination on the sample, but also to modify the illumination and or detection in the pupil plane. For the purpose of controlling the illumination of the pupil, one can place a DMD in the illumination path at a position which corresponds to a conjugate plane of the pupil. For the purpose of controlling the detection area in the pupil, one can place a DMD in the detection path at a position which corresponds to a conjugate plane of the pupil. In case one does not wish to separate the illumination and detection control, one may place a single DMD in the sample arm at a position which corresponds to a conjugate plane of the pupil.

The ability to control and possibly separate the illumination and detection area in the pupil can enable system designs which reduce unwanted reflexes as described under the section entitled "Illumination—Separation of illumination and detection path" or improve the applications described in the section entitled "Applications."

Since DMDs can generate arbitrary patterns at very high rates, it is also possible to modify the illumination and detection area in the pupil very rapidly, for example from sweep to sweep. This allows for the dynamic modification of the collection of light from different areas in the pupil, i.e. collection of light scattered by the sample in different directions, as a function of time. Respectively it enables the illumination of the sample from different angles as a function of time. The ability to use this is further discussed under the section entitled "Illumination—Continuous scanning with time-varying illumination".

Although the use of DMDs in frequency-domain imaging was herein described for the example of partial-field systems, they can be applied in a similar fashion to line-field and even point-scanning interferometric imaging systems. The ability to use DMDs for point-scanned confocal systems has previously been shown for multi-point confocal microscopy (Liang, M. et al., Opt. Lett. 22, 751, 1997).

d. Scanning with MEMS Mirror Array

Microelectromechanical systems (MEMS) minors are believed to be a promising alternative for point scanning systems (Sun, J. et al., Opt. Express 18, 12065-75, 2010). They have the potential to achieve significantly lower cost and size than galvanometric scanners. One of their drawbacks is that they are so far limited to relatively small mirror sizes and therefore limit the size of the illumination and collection pupil. In partial-field frequency-domain imaging, one can work around this limitation by employing an array of MEMS minors similar to the DMD embodiment previously described. In this case the DMD employs MEMS minors, which can not only switch between an on- and an off-illumination position, but are able to gradually change their orientation over a desired angular range. In the following we will call such a device a MEMS micromirror device (MMD). The MMD would be placed in the sample arm at a position corresponding to a conjugate plane of the pupil. In order to scan the field of light across the sample, the mirrors of the MMD would synchronously be tilted. While this method would, in a point-scanning system, result in signal degradation due to phase wash-out, it does not impact the signal in a partial field-system, because the light in the pupil is acquired with a spatially resolved detector. The only requirement is that each photosensitive element should not receive light from multiple mirrors, meaning that the image of an individual mirror in the pupil corresponds to the same area, or an integer multiple of the area, in the pupil as the image of an individual photosensitive element in the pupil.

Because MEMS minors are often 2-axis scanners, one typically needs only one MMD for scanning the field of light across the sample in two dimensions, compared to a galvanometric scanner based system, where one needs two scanners for the same task.

A MMD can also be used in part as a DMD, where some of the MMD's mirrors would be moved into an off-position, while other mirrors of the same MMD are still used to scan light across the sample. While the use of MMDs was herein only described for partial-field scanning, it can also be used for scanning a line illumination.

e. Scanning with a Single MEMS Mirror

As described in the section "Scanning Related Improvements—Scanning with MEMS mirror array", using a single MEMS mirror conjugate to the pupil plane of the sample will result in reduced illumination and collection apertures. These reduced apertures, though, are only a problem for the collection where a large numerical aperture is desired. Illumination on the other hand, does not require a large aperture. One could then imagine separating the illumination and collection paths such that only the illumination path uses the MEMS mirror which performs partial-field scanning. The detection path would then bypass the MEMS minor and the spatially resolved detector could be placed conjugate to either the image plane or the pupil plane.

In the case where the detector is conjugate to the image plane, a large detector would be necessary which covers the maximum FOV and the ROI on the camera would be scanned along it with the MEMS minor. In the case where the detector is conjugate to the pupil plane, a smaller 2D detector could be used with a constant ROI. These two instances are similar to what was discussed in section "Use of DMD in parallel frequency-domain imaging".

f. Orthogonal Scan Patterns

Field illumination systems may have a different NA along the two illumination dimensions. This can for example be helpful for reducing the confocal out of focus intensity loss. The drawback however, is that it creates an asymmetric point spread function (PSF). Here we describe a method for creating a volume with isotropic resolution in the X-Y plane out of two or more volumes, each with anisotropic resolution.

The method involves acquiring at least a second volume of data at the same positions, but rotated by 90 degree in the X-Y plane. In one example, the first volume has high resolution (high spatial frequencies) in the X-Z plane and low resolution (low spatial frequencies) in the Y-Z plane. The second volume is rotated by 90 degree (the point spread function is rotated as well) and therefore has low resolution in the X-Z plane and high resolution in the Y-Z plane. In one embodiment, the 90 degree offset between acquisitions is realized by placing a dove prism in the sample arm of the system and rotating it by 45 degree in between acquisitions. By combining the two volumes in post processing as will be described in more detail below, it is possible to create a volume with isotropic resolution in the X-Y plane. Similar methods are known from magnetic resonance imaging (MRI), to deal with similar issues, because MRI volumes often have anisotropic resolution, due to slices being thicker than the in-plane resolution (Aganj, I. et al., Magn. Reson. Med. 67, 1167-72, 2012; Museth, K. et al., Visualization 179-186, 2002; Tamez-Pena, J. G. et al., Medical Imaging 4322, 87-97, 2001; Roullot, E. et al., Signal Process. 84, 743-762, 2004; Hamilton, C. A. et al., Radiology 193, 276-9, 1994).

The two volumes with anisotropic resolution can be combined using a wavelet based image fusion method which takes the actual PSF of the imaging system into account (Aganj, I. et al., Magn. Reson. Med. 67, 1167-72, 2012). Wavelet fusion techniques are particularly well suited because they collect all useful information from each of the input images, whereas parts which only contain meaningless information are rejected, i.e. the wavelet transform divides the image into blocks of low and high frequencies for each direction, which then allows picking the low and high frequencies of the high resolution planes, while discarding the missing high frequencies of the low resolution planes. Other applicable image fusion methods, such as Fourier image fusion techniques, can be envisioned by a person skilled in the art of image processing (Museth, K. et al., Visualization 179-186, 2002; Tamez-Pena, J. G. et al., Medical Imaging 4322, 87-97, 2001; Roullot, E. et al., Signal Process. 84, 743-762, 2004; Hamilton, C. A. et al., Radiology 193, 276-9, 1994).

The same method can be applied to volumes where a holoscopic reconstruction was only applied to one of the dimensions in each of the volumes. This may for example be the case in volumes where the phase is only stable enough to apply a holoscopic reconstruction in one dimension but not the other dimension. Examples for such a case would be a line field system, which is inherently phase stable along the line, but may not be as phase stable in the scanning direction. Other examples are partial field scanning systems or point scanning systems, where the phase is quite stable in the fast scanning direction, however not stable enough in the slow scanning direction to enable a holoscopic reconstruction. In this case one would acquire two volumes, where the fast scanning direction is switched between the two volumes. A holoscopic reconstruction is then applied only to the dimension of the fast scanning direction in each of the volumes, resulting in one volume with high depth invariant resolution in the X-Z plane, but lower depth variant resolution in the Y-Z plane, and one volume with high depth invariant resolution in the Y-Z plane, but lower depth variant resolution in the X-Z plane. These two volumes can then be combined to a single volume with isotropic resolution with the methods described above.

Please note that the method of applying the holoscopic reconstruction only in the more phase stable dimension can as well be applied to a single volume. In this case one would obtain a volume with anisotropic resolution, which would still be sufficient for diagnostics using cross-sectional scans. Such a mode may be desirable for use in ophthalmic patients which have a lot of difficulties fixating, causing strong motion artifacts in the final volumetric data. Often times this is the case in elderly patients, for which the scans may be uncomfortable. One therefore may keep the number of scans to a minimum and skip the above described second volume scan.

The use of orthogonal scan patterns for point scanning OCT systems has been described to improve image registration (see for example U.S. Pat. No. 7,365,856 and Kraus et al. (Kraus, M. F. et al., Biomed. Opt. Express 3, 1182-99, 2012)). The orthogonal volumes collected from parallel interferometric systems for resolution enhancement as described above may also have benefit for registration purposes. The parallel acquisition will create truly motion artifact free scans in at least one dimension and will therefore create better results than using image data acquired with point-scanning systems.

g. Wide Field Scanning—Non-Raster Scan to Reduce Scan Depth Variability

When scanning the posterior or anterior segment of the eye or other spherical samples, one may observe significant path length variations between the edges and the middle of the FOV. Since the imaging window is often limited to a few millimeters, it may occur that the edges of the FOV may already be outside the depth imaging window, while the center of the FOV is well within the depth imaging window. Axial tracking methods are known from OCT (Pircher, M. et al., Opt. Express 15, 16922, 2007). They are however typically not applicable to high speed wide field OCT scans, because the path length difference within a single scan changes too rapidly. The path length variation can however be slowed down, by moving from a raster scan pattern to, for example, a spiral scan pattern as illustrated in FIG. 8A. In a spiral scan pattern one moves relatively slowly from the center of the FOV to the edge of the FOV. The path length when imaging a spherical sample therefore also varies much more slowly. In fact one would only have to adjust the delay by delta z per volume compared to +/− delta z in a single B-scan of a raster scan pattern, where delta z is the path length difference between the center of the FOV and the edge of the FOV. Other scan patterns with similar behavior such as for example a square spiral (FIG. 8B) or a series of concentric circles (FIG. 8C) can be envisioned by a person skilled in the art. These improvements are applicable to point scanning systems, partial field systems, as well as all others where a beam or a field of light is scanned in two dimensions.

h. Wide Field Scanning—Reflective Delivery Optics

A partial field frequency-domain imaging system with reflective optics such as convex or aspherical mirrors, instead of refractive optics, in the sample arm may enable larger FOVs on the retina. For telecentrically scanning large FOVs in the eye, one typically requires a large diameter, but short focal length lens in front of the patient's eye. The diameter can however not be arbitrarily increased and is approximately limited to d f, where d is the diameter of the lens and f is the focal length of the lens. With reflective optics, it is possible to create significantly steeper angles, as for example described in U.S. Pat. No. 5,815,242 for a point scanning laser ophthalmoscope. We recognize that a similar design is also beneficial for wide field partial field scanning.

Another significant advantage of reflective optics over refractive optics is that they don't reflect light back into the detection path. This is particularly important for non- or partially-confocal systems, such as parallel holoscopy systems which are more susceptible to such back reflections. When employing light sources, which create so-called coherence revival artifacts, in an interferometric frequency-domain imaging device, reflective optics provide a way of avoiding serious image artifacts, which are otherwise caused by reflexes from lenses in the sample path.

i. High Speed Scanning

Scanning systems typically use a raster scan, where the light is scanned quickly in one direction and slowly in a perpendicular direction. This however has two drawbacks in terms of maximum scan speed and laser safety. The scan speed is limited because one scanner might be used at its performance limit in terms of speed, while the other scanner is far from its performance limit. For example in a point scanning system with a field of view of 10 degree by 10 degree, 1000×1000 sampling points and a total acquisition time of 1 s, the fast scanner has to be rotated +/−5 degree at a frequency of 1 kHz, resulting in an angular speed of 10 degree/ms, while the slow scanner only has to be rotated at an angular speed of 5 degree/s. This makes very poor use of the slow scanner, which typically has the same speed capability as the fast scanner.

We therefore propose to distribute the workload among the two scanners by scanning at an angle. At an angle of 45 degree, the workload is equally distributed, resulting in a $2^{0.5}$ lower maximum angular speed. Using the same example as above, the formerly faster scanner is now only moving at an angular speed of 7.07 deg/ms, while the formerly slower scanner is now moving at the same speed. Hence, if the acquisition speed is limited by the scanner speed, one is able to increase the speed of the system by a factor of $2^{0.5}$.

For the laser safety it is advantageous because now both scanners are moving fairly fast. Hence, if the fast scanner fails and stops moving, the light will still be scanned fairly quickly. Whereas in traditional raster scan systems, with a fast and a slow scanner, the light would be scanned extremely slowly in case the fast scanner stops moving.

If a FOV rotated by for example 45 degree is undesirable, one could mount the scanners at the corresponding angle, in order to effectively create a horizontal/vertical raster pattern. Instead of mounting the scanners at an angle one could also employ a dove prism subsequent to the scanners in order to rotate the FOV by a desired angle.

j. Scanner-Less Systems

The need for only a single one axis scanner in line field systems has been identified in the prior art as a cost saving potential. It has however not been recognized that one can create an even simpler low cost line field device by not using a scanner at all and rotating the optics head or the entire instrument relative to the sample. Especially hand held devices would be well suited for such a design. The device could for example be designed like a hand held telescope, which the patient himself rotates either in between line acquisitions or during a series of line acquisitions. The simplest case would only involve one rotation by 90 degrees, creating two B-scans with 90 degree offset. It would however also be possible to create a volume scan this way by continuously rotating the device by 180 degrees. In such a case, the device could contain accelerometers, gyros or other motion and orientation tracking elements, which collect information about the current location and/or orientation, which will then be used to either trigger the acquisition or for registration during post processing.

This method is not limited to rotations but can also involve tip/tilt and translations and not only applies to line field systems but also partial field systems. e.g. partial field systems, where the partial field resembles a broad line. In such a system one may potentially avoid the use of additional orientation tracking hardware elements by using computational motion tracking methods for determining the rotation position over time. Suitable computational motion tracking methods are described in section "VI. Motion correction".

The motion detection methods described under "Motion correction" or speckle tracking methods, where changes of the speckle pattern over time are evaluated to estimate motion of an object (Liu, X. et al., Opt. Express 20, 16567, 2012), further enable scanner less partial field devices even with rectangular or circular partial fields. In such a device one could also keep the device fixed, move the fixation pattern and ask the patient to follow the fixation pattern with his eye. The speckle tracking provides information about the speed and distance of the eye movement and therefore enables the reconstruction of volumetric data by placing the acquired data at its correct position, effectively "painting" a volumetric image of the patient's retina.

IV. Acquisition Related Improvements a. Streak Mode Line Field Frequency-Domain Imaging

The speed of parallel frequency-domain imaging systems is today mainly limited by the available detection hardware. Cameras are limited in their line rate or frame rate. One method to achieve higher camera speeds is to operate the photosensitive elements in a non-integrating or continuous time mode as described in PCT Publication No. WO 2015/024663. Another method for avoiding the line or frame rate limit for swept source based line field frequency-domain imaging is to use a streak camera configuration, in which a streak scanner is placed in front of a 2D detector and the line of light is swept across the 2D array of photosensitive elements during each wavelength scan. The spectral information in such a system is acquired as a function of time and space, unlike in a normal swept source based line field system, where the spectral information is acquired solely as a function of time.

Figure 16:
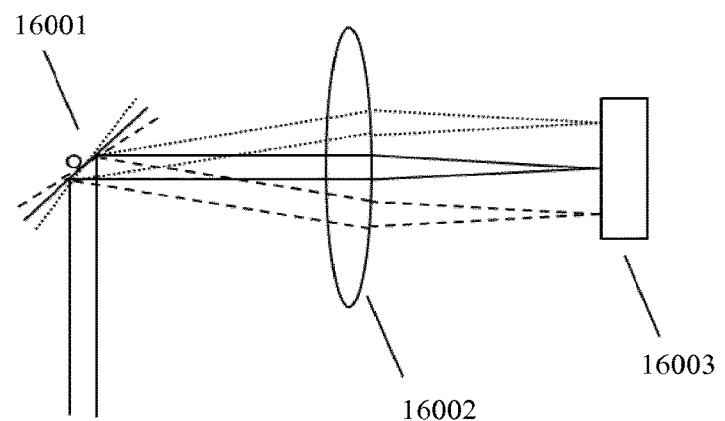
FIG. 16 is a schematic side view of a streak mode line field detection set-up according to one embodiment.

FIG. 16 schematically illustrates this concept. It is a schematic side view of a portion of streak mode line field detection set-up, where a streak scanner 16001 directs the line of light through a lens 16002 to different positions on the detector 16003 over time. The high frequency dashed lines represent the scanner orientation and light path at the beginning of the sweep, the solid lines in the middle of the sweep, and the low frequency dashed lines at the end of the sweep.

This method shifts the speed limitation, at least for a single line-field B-scan, from the detection electronics to the streak scanner, because the time for a single B-scan in such a system solely depends on the angular velocity of the streak scanner. Another significant change compared to a swept source based line-field system with a 1D detector, is that the number of spectral samples and imaging depth is not dependent on the frame rate, but rather on the number of photosensitive elements in the streak scanning direction.

Many commercially available 2D detectors can reduce the number of photosensitive elements which they read out in order to increase the frame rate. In many cases the number of rows of photosensitive elements is the main limitation for the frame rate. One could therefore envision a swept source based line-field frequency-domain imaging system which employs a 2D detector operated in two different modes:

1. A line-scan or partial-scan mode, in which only a single or a low number of rows of photosensitive elements is read out, in order to achieve very high frame rates. In this mode the streak scanner would be switched off, i.e. not moving, and the acquisition method would correspond to the typical swept source based line-field or partial-field method, where the spectral data is acquired as a function of time.
2. A full-area-streak mode, in which the full or a large portion of the detector's photosensitive elements is read out, in order to acquire B-scans within very short time periods, by using a streak scanner in front of the detector as described above.

A system which can switch between those modes could be used to acquire relatively low depth volumes or en-face images in the line-scan or partial-scan mode, as further described in the section entitled "Applications—Fundus imaging and enface imaging", while the full area-streak mode could be used to acquire motion artifact free B-scans with larger imaging depth.

When switching from line-scan or partial-scan mode to the full-area-streak mode, the integration time increases while the illumination time decreases. To compensate for the increased detector noise and reduced shot noise that results, one should increase the reference power in order to maintain the shot noise to be the limiting noise source.

The streak scanner can be used "bi-directionally", meaning that the forward as well as the backward sweep can be used to illuminate the detector. In case the detector has a long dead time, one can also choose to only use either forward or backward sweeps in order to let the scanner return to its initial position during the detector's dead time.

Wang et al. presented in 2011 a related approach for single point-scanning SD-OCT (Wang, R. et al., J. Biomed. Opt. 16, 066016, 2011). Since their system was not a parallel system, they however required two very fast scanners, one which scanned the imaging beam across the sample and one, which simultaneously scanned the spectra across a 2D detector.

b. Optical Fiber Bundles

An optical fiber bundle is a cable which contains more than one optical fiber. Optical fiber bundles which contain a large number of optical fibers are often used for transmitting optical images from one end of the bundle to the other. Such bundles are also known as image bundles. The optical fibers used for these bundles are typically multimode fibers. Optical fiber bundles are commonly used in endoscopes for medical, veterinary and industrial applications, but have also been proposed for the use in holography and parallel OCT (Zuluaga, A. F. et al., Opt. Lett. 24, 519-521, 1999; Coquoz, O. et al., Holography, Interferometry, and Optical Pattern Recognition in Biomedicine III 1889, 216-223, 1993; Coquoz, O. et al., Microscopy, Holography, and Interferometry in Biomedicine 2083, 314-318, 1994). The fiber arrangements can have different configurations. They can for example be arranged next to each other in a single row in order to create a linear array, or they can be arranged to create a square or rectangular grid, or other arbitrary configurations. It is also possible to have a certain configuration on one end of the fiber bundle and another configuration on the other end of the fiber bundle. Zuluaga et al. showed that fiber bundles can be used as an optical delivery probe (Zuluaga, A. F. et al., Opt. Lett. 24, 519-521, 1999). Optical fiber bundles can also be used to physically separate the detector from the interferometer, e.g. in an ophthalmological holoscopy system, where the interferometer resides in the optics head of the instrument and the detector is located in close proximity to a PC underneath the table. Another example for the case where the fiber bundle is used to separate the detector from the interferometer is in an endoscope, where the interferometer resides in the distal end of the endoscope, while the light source and detector however reside for example outside the endoscope. Another use for optical fiber bundles in frequency-domain imaging is to translate a distinct optical sampling lattice to a geometry which matches the detector configuration, e.g. transform a rectangular optical sampling lattice to a linear array of output fibers, to be used with a 1D detector.

c. Pupil Camera

OCT systems typically provide the user a video feed of the patient's pupil and iris during alignment (see for example US Publication No. 2007/0291277 hereby incorporated by reference). Since this video is being acquired on the optical axis of the OCT system, it helps the user to align the imaging beam relative the patient's pupil. In order to put the pupil camera on the optical axis of the OCT system, one typically places a dichroic minor in the OCT imaging path. This is undesirable because it introduces two additional optical surfaces, which cause losses and potentially impact the beam quality. The dichroic mirror and the necessary mechanical fixture also add to the cost of the system.

In a partial- or full-field frequency-domain imaging system, where the pupil is imaged to the detector, one is able to overcome both of these drawbacks. Instead of using an additional pupil camera, one can use the already existing frequency-domain imaging detector. Since the frequency-domain imaging detector ideally only acquires light from inside the pupil, it provides only a limited amount of information in its typical state. One however could use a detector with a larger number of photosensitive elements than necessary for the frequency-domain imaging system, of which only a portion is read out in frequency-domain imaging mode at very high frame rates. A larger area of the detector or the full detector, which for example provides a FOV of the entire eye and eye lid, is read out during pupil imaging mode. Since a pupil image is only required a few times per second (<30 Hz), one would be able to interleave the pupil imaging mode with the frequency-domain imaging mode, without significantly impacting the frequency-domain imaging mode. Since the pupil view is only needed for alignment, one would not necessarily need to interleave pupil images during the actual acquisition. The actual acquisition could therefore remain completely unaffected.

In order to maximize the use of the detector's dynamic range and to improve contrast, one could block the reference light during pupil imaging mode. This could be either achieved by a beam shutter, or by switching the laser off during pupil imaging mode.

The interleaved pupil image mode could also be used by the instrument to capture information necessary for automated pupil tracking to determine the best location for imaging and/or maintain that imaging location overtime as described in US Publication No. 2012/0274897 hereby incorporated by reference.

V. Reconstruction and Computational Adaptive Optics

The use of hardware based adaptive optics for wavefront correction is well established in astronomy and microscopy for point like objects to achieve diffraction limited imaging (Platt, B. C., J. Refract. Surg. 17, S573-S577, 2001; Beverage, J. L. et al., J. Microsc. 205, 61-75, 2002; Rueckel, M. et al., Proc. Natl. Acad. Sci. U.S.A. 103, 17137-42, 2006). It is currently an active field of research in optical coherence tomography and optical coherence microscopy (Hermann, B. et al., Opt. Lett. 29, 2142-4, 2004; Zawadzki, R. J. et al., Opt. Express 13, 8532, 2005; Sasaki, K. et al., Biomed. Opt. Express 3, 2353-70, 2012). Recently it has been shown that the phase information in the original detected data set can be mathematically manipulated to correct for known spherical aberrations in optical imaging techniques (Kumar, A. et al., Opt. Express 21, 10850-66, 2013; Colomb, T. et al., J. Opt. Soc. Am. A 23, 3177, 2006; Montfort, F. et al., Appl. Opt. 45, 8209, 2006; Kuhn, J. et al., Opt. Lett. 34, 653, 2009; Tippie, A. E. et al., Opt. Express 19, 12027-38, 2011; Adie, S. G. et al., Proc. Natl. Acad. Sci. U.S.A. 109, 7175-80, 2012).

a. Computational Chromatic Aberration Correction

In holoscopy, one typically illuminates the sample with many different wavelengths spanning over a broad spectral band. This provides challenges for refractive optics because they typically cannot be optimized to be perfectly achromatic over the full spectral range. One can therefore, even in a nominally achromatic system, expect a slight wavelength dependent focal shift (chromatic aberration). In holoscopy, each wavelength is acquired separately as a function of time or space, and since holoscopic reconstructions typically involve a propagation step of each wavelength, one is able to adapt this step in order to compensate for the chromatic aberration. Instead of propagating the acquired data $D(k_x, k_y,$ k) using a multiplication by a factor $\exp(-iz_0(k+k_z(k_x,k_y,k)))$, one can correct for the chromatic focal shift by propagating the acquired data $D(k_x, k_y, k)$ by a modified propagator, $\exp(-i(z_0+\Delta z(k))(k+k_z(k_x,k_y,k)))$, where $\Delta z(k)$ is the chromatic focal shift. Someone skilled in the art will recognize that other propagators may also be adjusted to take a wavelength dependent focal shift into account.

This method is also applicable to SD-OCT and SS-OCT with non-holoscopic reconstructions. In this case one can introduce a dedicated wavelength dependent propagation step prior to the traditional reconstruction.

b. Hybrid Hardware/Computational Adaptive Optics

In hardware based adaptive optics, one commonly uses a wavefront sensor, (e.g. a Shack-Hartmann sensor) to detect the wavefront and correct it accordingly using a deformable minor or a spatial light modulator (SLM) (Hermann, B. et al., Opt. Lett. 29, 2142-4, 2004; Zawadzki, R. J. et al., Opt. Express 13, 8532, 2005; Fernandez, E. J. et al., Vision Res. 45, 3432-44, 2005). In computational adaptive optics, one uses the phase information available in interferometric imaging methods such as holoscopy, in order to extract information about the shape of the wavefront of the light detected at the detector (Kumar, A. et al., Opt. Express 21, 10850-66, 2013; Adie, S. G. et al., Proc. Natl. Acad. Sci. U.S.A. 109, 7175-80, 2012; Adie, S. G. et al., Appl. Phys. Lett. 101, 221117, 2012). One then compensates for the detected higher order wavefront aberrations computationally. Here, we describe hybrid adaptive optics systems, which either use a wavefront sensor to detect wavefront shape and use this information as an input for the computational wavefront correction, or vice versa, systems which extract the wavefront shape computationally and compensate for it with e.g. a deformable mirror or a SLM. The preferred combination is likely to be the former case, because wavefront detectors are relatively inexpensive in contrast to a deformable minor or a SLM.

A plenoptic camera, also known as light field camera, is essentially a Shack-Hartmann sensor (Ng, R. et al., Computer Science Technical Report CSTR 2, 2005; Rodriguez-Ramos, L. F. et al., Astronomical and Space Optical Systems 7439, 743901-743901-9, 2009). Both consist of a microlens array in front of a 2D detector, which is why a plenoptic camera can also be used as a wavefront sensor (Rodriguez-Ramos, L. F. et al., Astronomical and Space Optical Systems 7439, 743901-743901-9, 2009). In such a system one can dual-purpose the light field camera as both a wavefront detector and a fundus imaging modality. For a description of the use of a light field camera in fundus photography, see US Patent Publication No. 2013/0010260 hereby incorporated by reference. In such a hybrid device, one can use the light field camera for color fundus imaging, fundus-auto-fluorescence imaging (FAF), fluorescence angiography (FA), etc. These images could then be combined with the holoscopy volumes, where e.g. the holoscopy image data is displayed in grey scale, while the fundus image data is overlaid in color.

Aside from using a light field camera, a holoscopy device can also be combined with other imaging modalities to create a multi-modality imaging device. Such a multi-modality device could be a holoscopy device, which in addition contains color fundus imaging capability, FAF capability, or FA capability, to only name a few examples. The integration of multiple modalities in a single device would have the advantage that the patient does not have to move from device to device for each imaging modality. It would also have a cost advantage over multiple separate devices, because a lot of the device's infrastructure, such as processor, display screen, common optical paths, packaging, table, etc. is shared among two or more imaging modalities.

c. Sub-Aperture Auto Focusing

In the section above, a combination of computational and hardware adaptive optics for the correction of higher order aberrations was described. A holoscopy system is also able to detect plain defocus for example by the split aperture method described by Kumar et al. (Kumar, A. et al., Opt. Express 21, 10850-66, 2013). By the offset between at least two sub-aperture images, one is able to tell the amount of defocus, i.e. the distance between the sample and the focal position as well as whether the sample is in front of the focal position or behind the focal position. This is all the information needed to bring the sample immediately (non-iteratively) optically into focus, e.g. by translating a lens or changing the focal length of an adaptive lens. This method has the advantage of significantly faster focusing compared to today's commercially available OCT systems, which typically use active autofocusing methods, where the focus is scanned and the optimum focus position is determined by detecting a maximum in intensity and/or contrast in the image throughout the focus scan.

It should be mentioned that although the sub-aperture method can be used to reconstruct images with depth invariant focus for any point scanning or parallel holoscopic system, it is in some cases advantageous to acquire close to the optical in-focus position in the first place. This is for example the case in high NA point-scanning systems where one observes not only an out of focus resolution loss but also a significant out of focus intensity loss. The high speed split aperture auto-focusing can in such a case for example be used to continuously track the focus in the presence of axial sample motion.

The described split-aperture auto-focusing method is related to the phase detection auto-focus method known from traditional photography. In phase detection auto-focusing, the pupil is split physically by apertures and/or microlenses, whereas in a holoscopy system, we are able to computationally propagate between image plane and pupil plane and are therefore able to split the aperture computationally. This has the advantage that no additional hardware such as focus pixels is needed to implement this auto-focusing technique.

d. Taking Image Distortions into Account for Reconstruction

Inhomogeneous refractive index distribution throughout the sample or non-telecentric scanning distorts the assumed $k_x, k_y, k_z$ sampling grid, and therefore also compromises the result of holoscopic reconstructions. We therefore describe here how to measure or estimate the distortions introduced by variations of the refractive index as well as non-telecentric scanning and take them into account by modifying the resampling in the spatial frequency domain accordingly.

Figure 9:
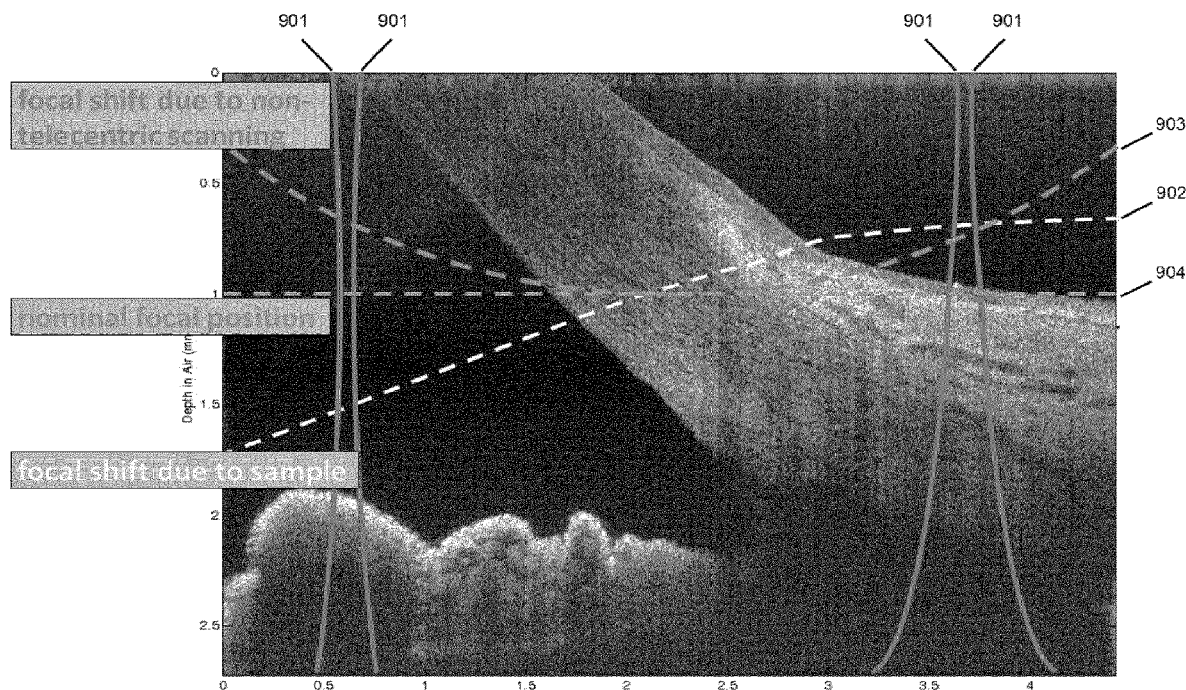
FIG. 9 shows an OCT B-scan of the human anterior chamber angle to illustrate the types of optical distortions that can be evident in OCT B-scans due to refractive index variations.

In the retina, one typically only observes moderate refractive index variations, which do not have a significant impact on the reconstruction result. However, in the anterior segment, the situation is different due to the large refractive index differences between the cornea and other tissue as well as the curved surface of the cornea. This can certainly cause the holoscopic reconstruction to fail. FIG. 9 shows an OCT B-scan of the human anterior chamber angle as an example where it would be especially beneficial to correct for varying focal positions and varying refractive indexes throughout the image in order to obtain a correct holoscopic reconstruction. The nominal focal position is indicated by line 904. The large refractive index difference between air and the cornea however causes a significant shift in optical path length and focal position throughout the B-scan, which is schematically illustrated by the lines 901, which represent the beam waist of Gaussian beams in two different locations, as well as line 902, which indicates the focal position throughout the B-scan. Line 902 scales inversely with the surface of the cornea. To correct for these effects, one would ideally first correct for any image distortions caused by the cornea, and then apply a reconstruction which also takes the different focal positions into account.

Line 903 illustrates the effect non-telecentric scanning has on the focal position and optical path length. Both the spatially varying focal position as well as the spatially varying optical path length has a significant impact on the reconstruction result. The standard holoscopic reconstruction typically applies a resampling in the spatial frequency domain, which assumes a constant focal position and a constant optical path length difference throughout the scan.

We previously mentioned that some holoscopic reconstructions involve a propagation step of the measured fields to the reference plane at each optical frequency in the spatial frequency domain by a diffraction kernel $\exp(-iz_0(k+k_z(k_x, k_y,k)))$. The same step can also be implemented by a circular shift in the spatial domain as for example described by Ralston et al. (Ralston, T. S. et al., Opt. Express 16, 2555, 2008). In this case, the data in the spatial domain is circularly shifted so that the nominal focal plane coincides with the plane that represents the zero optical path length difference. This circular shift was so far always applied to at least a full B-scan. It was not recognized that in acquisitions where the focal position varies throughout the acquisition, it is beneficial to apply a tailored circular shift for each A-scan. The magnitude of this circular shift is adapted for each A-scan in order to shift the actual focal position at each individual transverse location in a way that it matches the zero optical path length difference plane. This enables a correct reconstruction even in cases where the actual focal position varies throughout the acquisition from the nominal focal position used for the reconstruction. For reconstructing a 3D representation of a sample with strong refractive index variations, one first has to apply a more complex image correction in the spatial domain, or apply a modified resampling function in the spatial frequency domain, which takes the image distortions and/or refractive index variations into account.

e. Stacking of Holoscopy Acquisitions

Figure 10:
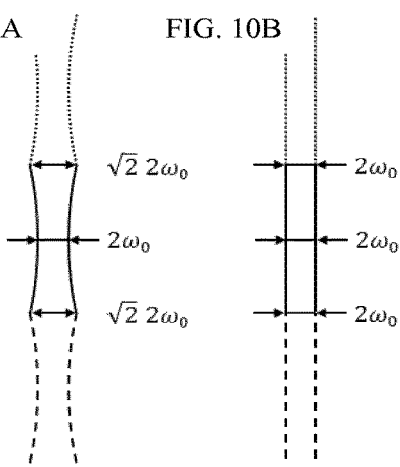
FIG. 10A illustrates a plurality of OCT data volumes stacked in the axial direction according to the Prior Art in which the transverse resolution varies with depth.
FIG. 10B illustrates an embodiment in which multiple partial-field holoscopy volumes are stacked in the depth direction in which the final volume has depth invariant resolution.

Focus stacking of OCT and single plane holography acquisitions have been previously proposed with the goal of creating an extended depth of field (DOF) (Huber, R. et al., Opt. Express 13, 10523, 2005). By applying a holoscopic reconstruction, one is able to obtain a DOF which extends over several Rayleigh ranges, without the need for stacking multiple acquisitions with shifted focus. Aside from attempting to increase the DOF (Huber, R. et al., Opt. Express 13, 10523, 2005), stacking of multiple volumes has previously been proposed for increasing the depth range of OCT acquisitions (see for example U.S. Pat. No. 8,125,645 hereby incorporated by reference). In both cases, one however obtained a final volume where the transverse resolution varies with depth (FIG. 10A). In FIG. 10A this is illustrated by the three stacked Gaussian beams (dotted, solid and dashed beams), which exhibit an increasing beam waist away from their individual foci.

In one embodiment of this application, multiple partial-field holoscopy volumes are stacked in the depth direction. The multiple partial filed volumes are acquired with different reference arm positions, and therefore correspond to different imaging depths. Each partial field volume is reconstructed with a holoscopic reconstruction in order to obtain depth invariant resolution within each individual volume as well as within the final larger volume, regardless whether each individual acquisition is focused or not (FIG. 10B). In FIG. 10B this is illustrated by showing three beams (dotted, solid and dashed beams) with depth invariant resolution; in contrast to FIG. 10A the beam waist of each individual beam does not increase away from its focus. The stacking of the volumes can, for example, be realized by stitching multiple reconstructed volumes with the help of image fusion techniques. Among other things, this makes it beneficial to take depth stacked images without adjusting the focus of the individual acquisitions.

A coherent reconstruction method for point-scanning multifocal holoscopy has recently been published by Xu et al. (Xu, Y. et al., Opt. Express 22, 16606, 2014). While Xu's published method of stacking point-scanning holoscopy acquisitions has the advantage of increased SNR over a larger depth, the stacking of parallel holoscopy acquisition as described herein serves mainly the purpose of reducing the sweep time. Each shallow individual volume can be acquired more quickly and is therefore less susceptible to motion artifacts. The acquisition time of each individual volume is reduced by acquiring less samples or frames per sweep. Because the imaging depth scales with the number of spectral samples acquired over one wavelength sweep, one receives shallower individual volumes, which can then be stacked in order to achieve a desired total imaging depth. Off-axis parallel holoscopy systems are particularly suited for this method because they do not suffer from overlapping minor images, and therefore enable placing the point where the sample arm matches the length of the reference within the area of interest in the sample without having to deal with scattering signal from beyond this point folding back into the image and creating artifacts. In an off-axis parallel holoscopy system, one would ideally design the data acquisition system's analog bandpass filters in a way that aliasing artifacts are greatly suppressed and only frequencies within the digitization bandwidth are permitted.

f. Reconstructions for Preview and Alignment Mode

A system with a spatially resolved detector typically automatically collects volumetric data. Often times it is more convenient to use cross-sectional images (B-scans) for aligning the system relative to the patient's eye. For this purpose, some of the data can be discarded creating a B-scan out of a volume. It may however be more desirable to make use of all the acquired data. To do so, one can combine part of the data or the entire data set in one dimension (for example by summing or averaging) in order to transform the volumetric data into a B-scan.

In case only one or multiple B-scans instead of volumes are displayed for alignment or preview modes, it is desirable to only apply the holoscopic reconstruction on the B-scans (or average B-scans as described above) in this mode. This reduces the computational load by avoiding unnecessary real time data processing.

g. Synthetic Aperture Off-Axis Holoscopy

An off-axis acquisition scheme creates a carrier frequency across the detector which creates a shift in the spatial frequency spectrum. One side of the spatial frequency spectrum experiences an up shift in spatial frequency, and the other side is actually getting downshifted. This downshift can be used to resolve higher frequency content which would otherwise lie outside of the detectable spatial frequency space. Since the downshift however only occurs in the direction of the off-axis angle, one ideally acquires multiple data sets with varying off-axis-angle-direction in order to increase the spatial frequency space in all directions. For example a set of 4 acquisitions with off-axis angles from "north", "east", "south" and "west" should be sufficient to provide sufficient information to create a combined data set with a significantly enlarged spatial frequency space and hence improved resolution in all directions.

Such a method could be implemented by using for example a spatial light modulator (SLM) as the reference mirror. On the SLM one would then display gratings with different orientations. One could even choose to vary the grating frequency on the SLM to create different off-axis angles in order to adapt to the spatial frequency content of the sample.

Alternatively the grating could be rotated in between acquisitions in order to generate off-axis angles from different orientations. To address the higher spatial frequencies, the reference beam would typically enter at a steeper off-axis angle than in a design where only one off-axis acquisition was obtained.

VI. Motion Correction

S. H. Yun et al. investigated the influence of axial and transverse motion artifacts on the PSF and SNR in SS-OCT (Yun, S. H. et al., Opt. Express 12, 2977, 2004). They identified three effects sample motion has on the SS-OCT image: 1) a Doppler shift, 2) an axial PSF broadening and 3) transverse PSF broadening. We previously described the necessity for short sweep times in order to minimize the impact of sample motion on the image quality. If motion artifacts cannot be avoided, one can correct for motion artifacts computationally. One approach for the compensation of axial motion artifacts in swept-source based OCT systems has been described by Hillman et al. (Hillmann, D. et al., Opt. Express 20, 6761-76, 2012). It however only describes global corrections, i.e. corrections which are applied to the entire depth of the acquisition. Since some samples may only exhibit moving particles in some layers and not in others, for example blood flow in a blood vessel within retinal tissue, it is desirable to apply local computational motion corrections. Local motion corrections can be applied either in the spatial domain or in the frequency domain In the frequency domain they can be applied in the form of frequency dependent motion corrections, for example by a fractional Fourier transform or a frequency dependent phase correction. One example of how a fractional Fourier transform can be used to correct depth dependent axial PSF broadening was recently described by Lippok et al. for the application of a depth dependent dispersion correction in optical coherence tomography data (Lippok, N. et al., Opt. Express 20, 23398-413, 2012). It was however not recognized that the axial PSF broadening introduced by motion in swept source based frequency-domain imaging techniques, which is a similar effect as PSF broadening due to a dispersion mismatch, however with a different root cause, could also be locally corrected with this method.

Another example for a depth dependent (or frequency dependent) motion correction method is to create several band-pass filtered copies of the original data, where each copy represents a different frequency band, and apply methods traditionally known from OCT dispersion correction to each individual copy (Wojtkowski, M. et al., Opt. Express 12, 2404, 2004). After each copy has been optimized individually for example according to parameters like sharpness or contrast, they are synthesized to a recombined single volume, which again contains the entire frequency information or a frequency dependent phase correction.

a. Tracking and Correction of Motion and Rotation Occurring During Acquisition of Parallel Frequency-Domain Imaging Data There are six degrees of sample motion that can occur during the acquisition. These motions can be described by the orthogonal sets of:

1) Three degrees of motion of the sample along the x, y, and z axis
2) Three degrees of rotation of the sample about the x, y, and z axis.

Note that other orthogonal sets could also be used to describe these six degrees of freedom. One can track the x, y, and z motion by tracking the position of any region of the tissue during the acquisition. For simplicity, we will define this first position P1 as being at the x, y, z origin (x=0, y=0, z=0). However, tracking this point will not give us information about the three degrees of rotation about the origin. Tracking the position of a second point, P2, will provide information about rotation in two dimensions, but still not provide information about rotation about the axis defined by a line between the two points. For instance, if this point is on the x axis at x=1, y=0, z=0, we can obtain information regarding rotation about the y axis and z axis, but no information about rotation about the x axis. In this case, rotation about the z axis is given by relative displacements between the two points along the y axis. And rotation about the y axis is given by relative displacements between the two points along the z axis. Note that, to first order, one should get minimal relative displacements between these two points along the x axis, at least for small rotations, $\gamma$, where $\gamma$ is the amount of rotation about the y or z axis. The displacement is given by $(1-\cos[\gamma])$, which is approximately $\gamma^2$ for small angles.

The position of a third point, P3, should be tracked in order to obtain information on the rotation about the axis defined by the first two points (the x axis in this case). As an example, if the point x=0, y=1, z=0, is selected, then displacements between point P3 and point P1 along the z direction will provide the information about the last degree of freedom, rotation about the x axis. Here we see that by measuring the x, y, and z position of three points, we have a total of nine measurements. There are three parameters measured that are redundant (displacement along the line connecting any two of the three points), resulting in the measurement of the six degrees of freedom. Ideally these three points should be as far apart as possible to accurately measure rotations, as long as there is significant signal (back scattering of light by tissue) in the areas being measured, so that accurate position measurements can be made.

Figure 17:
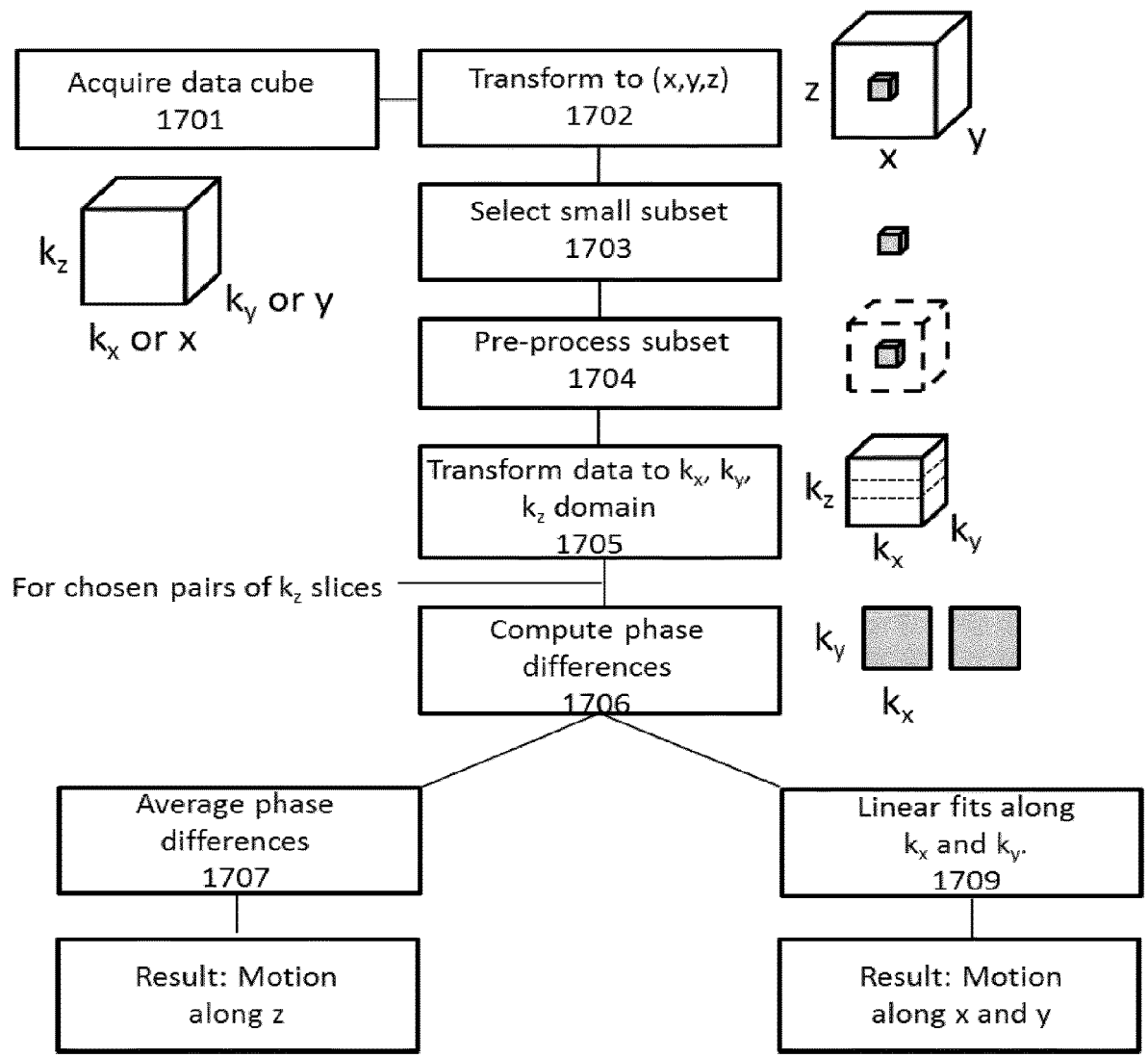
FIG. 17 is a flow chart illustrating the steps involved with a motion correction technique according to one embodiment of the present application.

A method for tracking one of these three locations is illustrated in FIG. 17 and described as follows:

1. Acquire a 3D data set (step 1701) and transform it into an (x, y, z) coordinate space (step 1702) where there are no lenses between the sample and this space. Note that this coordinate space could be shifted axially from the sample. For instance, if one collected the light with a flat reference wavefront in a lensless holoscopy system like that described by Hillman (Hillmann, D. et al., Opt. Lett. 36, 2390-2, 2011), one would only need to do a transformation from ($k_x$, $k_y$, $k_z$) to reach an acceptable coordinate space
2. Select a reasonably small 3D sub-region (step 1703) in this 3D space (say for instance 64×64×64 voxels) that has significant signal, and zero out all the other data. Note that one could also just copy the 64×64×64 sub-region into another array and work on this new array. Due to motion during acquisition, significant smearing along the axial dimension may be apparent. The sub-region should be chosen to capture a sufficient fraction of PSF in all three dimensions.
3. Preprocess the data (step 1704). In one type of preprocessing, the data is apodized so that the central photosensitive elements carry more weight than the edge photosensitive elements (one apodizing approach here for the 64×64×64 array would be to multiply the array by: $(\sin[\pi x/63]\sin[\pi y/63]\sin[\pi z/63])^2$, where x, y, and z are the three indices in the array, each varying from 0 to 63). An alternative preprocessing step is to pad the array with zeroes, for example dropping the array into the center of a 128×128×128 array of zeros.
4. Fourier transform the array in x, y, and z, so as to be in the $k_x$, $k_y$, $k_z$ space (step 1705).
5. Determine phase shifts between $k_z$ planes as a function of $k_x$ and $k_y$ (step 1706). As the data was originally taken sequentially in $k_z$, each plane in $k_z$ corresponds to a point in time. The phase shifts between two $k_z$ planes (step 1706) can be measured by taking the complex conjugate of one of the planes, and then multiplying each element in the first plane with the corresponding complex conjugated element in the second plane. This results in a plane of data, where the phase of each element corresponds to the difference in phase between the two planes, and the amplitude at each location corresponds to the strength of the signal.
6. Axial shifts (in z) between acquisitions will lead to a uniform phase shift across the $k_x$, $k_y$ plane. The axial motion can thus be extracted, for example, by averaging the phase differences (step 1707).
7. Lateral motion in x will lead to a phase shift proportional to $k_x$, and motion in y will lead to a phase shift proportional to $k_y$. The lateral motion can thus be extracted, for example, by performing linear fits along $k_x$ and $k_y$ (step 1709). If the axial location of the (x, y, z) coordinate space has a path length that is displaced relative to the reference arm path length, then there will also be a relatively uniform phase shift between detector acquisitions due to the Doppler change in wavelength.

The detected sample motion can be used to either correct motion artifacts in post processing or to provide feedback to the scanners, allowing them to follow the sample motion in real-time and thereby avoid motion artifacts in the image. One way of correcting for the detected sample motion is to apply phase shifts opposite to the detected phase shifts. Another method is to calculate the absolute motion in space and translate, tilt, rotate and/or transform the acquired data in a way that compensates for the detected motion.

b. Off-Axis Detection for Tracking and Correction of Motion and Rotation

In the section "Motion correction—Tracking and correction of motion and rotation occurring during acquisition of parallel frequency-domain imaging data", the phase for each $k_x$, $k_y$ plane was accessed by use of Fourier transforms along $k_z$ which was part of the parallel frequency-domain data processing. Obtaining the phase in this manner implicitly performs a Hilbert transform along $k_z$ and uses data acquired over a range of wavelengths to measure the phase at a single point. Alternatively, one could consider an off-axis configuration parallel frequency domain interferometric imaging system, such as a line field, partial field or full field system, where the reference beam is at an angle to the sample beam which allows for heterodyne detection in the spatial data acquired. By demodulating the signal (either in hardware or software), the relative phase for each spatial point can be obtained for each individual wavelength. By Fourier transforming the data appropriately into the ($k_x$, $k_y$, $k_z$) domain, a dataset equivalent to that described in step 4 in section "Motion correction—Tracking and correction of motion and rotation occurring during acquisition of parallel frequency-domain imaging data", can be obtained. This technique implicitly uses the data acquired over a range of spatial locations (rather than a range of wavelengths) to measure the phase at a single point. The same techniques to measure motion along x, y, and z can then be followed.

Acquiring and processing data in this manner has several benefits over in-line detection. Some of these benefits include the ability to efficiently perform motion correction in parallel with acquisition, as the phase of each $k_z$ plane can be independently determined. Furthermore, off-axis detection could provide a more sensitive measurement than relying on a Hilbert transform along $k_z$, for instance in the presence of lateral motion which could make the comparison of two $k_z$ planes unreliable for phase determination. The benefits of off-axis detection also extend beyond motion correction and provide more robust removal of artifacts such as insufficient reference background subtraction or a strong autocorrelation of the sample itself.

Again, the detected sample motion can be used to either correct motion artifacts in post processing or to provide feedback to the scanners, allowing them to follow the sample motion in real-time and thereby avoid motion artifacts in the image.

c. Tracking and Correction of Motion and Rotation Using a Single Contiguous Patch By tracking the (x,y,z) position of a reasonably small subset of the full dataset of a partial field system, motion in x, y, and z is naturally provided. As described previously in section "Motion correction—Tracking and correction of motion and rotation occurring during acquisition of parallel frequency-domain imaging data", by performing similar measurements of two other subsets, one can determine motion in all six degrees of motion. It is also possible to use a single 3D subset, albeit possibly somewhat larger, to track all six degrees of freedom. Using the above methods described in "Tracking and correction of motion and rotation occurring during acquisition of parallel frequency-domain imaging data" and "Off-axis detection for tracking and correction of motion and rotation", motion in x, y, and z can readily be detected. Then, by numerically propagating the 3D subset into the (x, y, $k_z$) domain, and again taking the complex conjugate of one plane, and multiplying each element in the first plane with the corresponding complex conjugated element in the second plane, rotations about the x and y axes will result in phase shifts proportional to x and y respectively. The amplitude of the motion can then be quantitatively measured again, for instance, by curve fitting or averaging phase differences. We note that, in these measurements, the pivot point for rotation will be assigned as the center of the ROI. This does not cause any problems, though, as a rotation about a pivot point, $p_0$, can be defined as a combination of translations and rotations about any other pivot point, p. Therefore some conversions will be necessary if the ROI changes from acquisition to acquisition. Lastly, rotations about the optical axis can be measured in either the ($k_x$, $k_y$, $k_z$) or (x, y, $k_z$) domains, and can be measured in many ways such as tracking edges or peaks between consecutive planes.

The detected sample motion can be used to either correct motion artifacts in post processing or to provide feedback to the scanners, allowing them to follow the sample motion in real-time and thereby avoid motion artifacts in the image.

d. Tracking of Motion by Absolute Angle Resolved Velocity Measurements

The phase resolved Doppler based absolute velocity measurement method described under "Applications—Absolute angle resolved velocity measurements" can be used to track sample motion. By measuring the velocity of scatterers at a single point of the sample, only translations in x, y, and z of the sample can be determined, while tip, tilt and rotation of the sample are not detectable. By instantaneously acquiring a partial field with at least 3 spatially separated sample points also these degrees of freedom can be detected. In order to increase the sensitivity to tip, tilt and rotation, one can also choose to monitor the velocity of at least three different further spatially separated locations in the sample by successively acquiring three different partial fields. In order to minimize a potential error, the time difference between these partial field acquisitions should be as small as possible.

The detected sample motion can then be used to either correct motion artifacts in post processing or to provide feedback to the scanners, allowing them to follow the sample motion in real-time and thereby avoid motion artifacts in the image.

e. Errors in Motion Measurements

The above motion measurement techniques do have limitations. First, if axial motion between adjacent wavelength acquisitions is too large, phase wrapping will occur and fringe-washout will also reduce the SNR and affect the reliability of the motion measurements. If lateral motion is too large, any speckle or features previously used for tracking could also washout, leaving minimal features to track. As motion is somewhat continuous (i.e. acceleration cannot be infinite), one can also use the motion between the previous acquisitions as a predictor of the motion in the current acquisition. For instance, one could shift the data to compensate for this predicted motion prior to the motion calculation to reduce phase wraps (positive or negative phase shifts with a magnitude greater than $\pi$).

In an in-line configuration, further complications arise when sample structure appears near the zero optical path length depth. In this situation, the mirror image may overlap the desired image. These two images will move in equal and opposite directions axially destroying any phase information for axial motion measurements. Thus, if image structure is detected to be close to the zero optical path length depth, a ROI in the image free of any mirror image should be selected for motion measurements. We note that although the mirror image will affect axial motion measurements, lateral motion measurements can still be made in an ROI containing both the minor and real image.

When a small ROI is selected to measure motion, this measurement only reflects the local motion and may not be applicable over the entire data set. To overcome this, multiple ROIs can be chosen, and knowledge about when in time each ROI was acquired can be used to interpolate/extrapolate motion over the entire dataset.

VII. Illumination a. 1060 nm Holoscopy

All published holoscopy systems so far used light in the 800 nm wavelength region. The use of longer wavelength light has been proven to be beneficial for retinal and anterior segment imaging with point-scanning systems (Povazay, B. et al., Opt. Express 11, 1980, 2003; Unterhuber, A. et al., Opt. Express 13, 3252, 2005). In particular, light in the wavelength range between 990 nm and 1110 nm can still be used for imaging of the human retina in-vivo, due to a minimum in the water-absorption spectrum at these wavelengths. In fact, it even enables imaging of deeper structures like the choroid and sclera, due to its lower scattering coefficient compared to light in the 800 nm wavelength region. It also significantly enhances the image quality in the presence of cataracts.

The use of longer wavelength light has also been demonstrated to provide superior image quality for imaging the anterior segment of the human eye. For imaging from the cornea down to the posterior lens surface, one often chooses to use light in the 1060 nm or 1310 nm wavelength band. With the introduction of 1060 nm swept sources with very long instantaneous coherence lengths, full-eye imaging even became feasible (Grulkowski, I. et al., Biomed. Opt. Express 3, 2733-51, 2012). The advantage of the larger penetration depth at longer wavelengths, and the larger coherence length of those light sources has not been fully exploited due to the limited depth of focus of the currently used non-holoscopic OCT reconstructions. We therefore include in the embodiments described herein, the use of longer wavelength light, in particular light in the 1060 nm, 1310 nm, and 1550 nm wavelength regions, for holoscopy. It is also possible to use holoscopic reconstructions with interferometric frequency domain systems which employ single longitudinal mode swept sources, such as MEMS tunable vertical cavity tunable lasers (VCSEL) or sampled grating distributed Bragg reflector (SG-DBR) lasers. Since silicon (Si) detectors are not very sensitive to the 1060 nm or 1310 nm wavelength band, Indium Gallium Arsenide (InGaAs) or Germanium (Ge) detectors can be used for holoscopy in the 1060 nm, 1310 nm, and 1550 nm wavelength bands.

b. Intentionally Aberrated Illumination Optics

Cylindrical lenses are often used to create a line focus from a collimated Gaussian beam. One drawback of this method is that the resulting line has a Gaussian intensity distribution along the direction of the line. This is undesirable for line field imaging because it also results in a Gaussian intensity distribution across the image. A common work around is to truncate the line to only a certain central portion, with a defined intensity variation. FIG. 11 shows a plot of a Gaussian normalized intensity distribution. The central red part of the bell curve indicates the region, where the intensity drop across the line is equal to or less than 20% of the maximum intensity. The total optical power falling outside of this region and therefore not used for imaging, corresponds in this example to 49.9% of the total power. This is especially problematic because currently available light sources provide still less than the desired optical output power.

The non-uniform distribution of light along the line created by a standard cylindrical lens is illustrated in FIG. 12C. Powell lenses resemble a round prism with a curved roof line (see FIG. 12A). The rounded roof is a two-dimensional aspheric curve that generates a large amount of spherical aberration that changes the intensity distribution along the line as illustrated in 12D. The intentionally introduced aberration is designed to create a line of light with a homogeneous intensity distribution as illustrated in FIG. 12B. Here we describe using such an arrangement in line field based interferometric imaging systems, particularly holoscopic line field imaging systems.

Powell lenses for line field holoscopy can create non-cylindrical wavefronts as illustrated in FIG. 13B in comparison to the cylindrical wavefronts created by cylindrical lenses as illustrated in FIG. 13A. In both cases a flat wavefront (illustrated by straight red lines) is moving towards the lens and is then focused (illustrated by curved red lines). The roof like shape of the focused wavefront in the case of the Powell lens (FIG. 13B) resembles the shape of the front surface of the Powell lens. Especially with prior knowledge of the expected wavefront, it may, if necessary, be possible to correct for the introduced wavefront aberrations in post processing as part of the holoscopic reconstruction, by taking the shape of the wavefront into account for the resampling in the spatial frequency domain as part of the holoscopic reconstruction. The sub-aperture based aberration measurement and correction technique presented by Kumar et al. is particularly well suited for detecting even higher order spherical aberrations and correcting them and may therefore be a natural fit for the here described optics (Kumar, A. et al., Opt. Express 21, 10850-66, 2013).

Combining illumination with the above described optics with a detection path containing only standard optics, may help to minimize the influence of the wavefront distortions on reconstruction when imaging scattering samples.

While the homogenizing illumination method was described for a line-field system and cylindrical lenses, it can also be applied to partial- or full-field illuminations by using specific beam shaping optics such as Gauss-to-top hat lenses.

c. Light Source Arrays

One of the advantages of parallel OCT systems is that they are able to increase the illumination power on the sample because the light is distributed over a larger area. In some cases one may even be able to increase the sample power to a level which is difficult to obtain with a single laser. It may therefore be beneficial to use multiple lasers or laser arrays in order to reach the desired illumination power on the sample for parallel frequency-domain imaging systems.

Electrically pumped MEMS tunable vertical cavity surface emitting lasers (VCSEL-Es) (Jayaraman, V. et al., Optical Coherence Tomography and Coherence Domain Optical Methods in Biomedicine XVIII 8934, 893402, 2014) are particularly well suited to be employed in laser arrays. Their cavities are very small and are grown next to each other on a common substrate. Due to their vertical cavity and light emission through the surface, they can be used without the need of dicing the wafer to individual lasers, enabling arrays of up to thousands of lasers.

Another laser type which may be well suited for a cost effective implementation of multiple parallel light sources, are sampled grating distributed Bragg reflector (SG-DBR) lasers (Bonesi, M. et al., Opt. Express 22, 2632, 2014). While their laser control electronics are relatively complex and expensive, the actual laser chip is rather inexpensive. One could therefore envision a source which shares the same control electronics for multiple laser chips.

Light source arrays can also be used to solve the above described problem of inhomogeneous intensity distributions. While each individual beam would exhibit a Gaussian intensity profile, the maximum intensity of the individual light sources does not tail off towards the edges of the light source array. If the detector configuration matches the light source array configuration, one will observe a Gaussian intensity distribution on each individual photosensitive element, however not across the entire detector.

Light source arrays can further be used to create a scanner-less partial field frequency-domain imaging system, similar to the above described DMD based scanner-less frequency-domain imaging system. In the case of a light source array based system, one does not necessarily require a DMD for switching on and off certain illumination regions. Instead, one can in such a system, where a light source array is imaged to the sample, simply switch parts of the array on and off. The size of the image of the entire light source array on the sample would define the maximum FOV, while the area of the light sources in the on position would correspond to the area of the instantaneous FOV on the sample Similar to the DMD based frequency-domain imaging system, one also does not have to modify the detection path in the case where the detector is positioned at a conjugate plane of the pupil. In the case where the detector is positioned at a conjugate of the sample, one can use a detector with a larger number of photosensitive elements and move the ROI which is being read out accordingly.

In case one wants to keep the number of light sources below the number of individual partial-fields, one can combine a light source array with a DMD based scanner-less frequency-domain imaging system. Such a configuration can for example be used to satisfy the high power requirement of a DMD based scanner-less frequency-domain imaging system. Each light source of the light source array would in this case be used to illuminate multiple partial-fields on the DMD. For example a 10×10 light source array would be used to illuminate the DMD, but the DMD would be used to display 100×100 patterns, which would then be imaged onto the sample. In such a case one individual source of the light source array would be used to illuminate one 100th of the total FOV or in other words, 100 individual partial fields.

d. Separation of Illumination and Detection Path

Point scanning OCT systems in the past have typically used a single mode fiber to illuminate and collect light from the sample so as to collect a single mode that matches the reference arm mode, also contained in a single mode fiber.

In partial-field systems, there is no mode matching requirement other than that the angle of incidence between reference and sample light must not generate spatial oscillations that are higher than the Nyquist frequency of the detector. This significantly simplifies the collection of the sample light as multiple modes of the light returning from the sample can be collected and interfered with the reference light. Elimination of the mode matching requirement enables many new optical designs for the system. One exemplary embodiment is schematically illustrated in FIG. 14 for a full-field imaging system. In FIG. 14 light from a swept source 1401 is split into sample light and reference light by a fiber coupler 1402. The sample 1403 is illuminated from the side by pointing the sample arm fiber tip at the sample. The sample arm light is shown as solid lines and the reference arm light is shown as dashed lines. The backscattered light from the sample is collected through separate detection optics (lenses 1404 and 1405) and collected by a detector (camera 1406). The reference light (dashed lines) illuminates the detector on its own optical axis. Sample and reference light then coherently interfere at the detector. One key aspect of such designs is that, as the backscattered sample light no longer needs to be coupled back into its original mode, the incident and returning sample light can be separated in space and travel different paths in the sample arm, making possible systems that illuminate and collect the sample light through different parts of a lens that has problematic reflexes, such as the human cornea. This then makes frequency-domain imaging systems in the form of fundus camera designs or broad line fundus imaging designs with pupil-splitting arrangements possible.

In one embodiment, illumination and detection path can be separated with the help of DMDs as described in the section entitled "Scanning related improvements—Use of DMD in parallel frequency-domain imaging."

The ability to spatially separate illumination and detection paths further allows interfering the reference light and sample light on the detector rather than at a beamsplitter. This has the advantage that all the sample light can reach the detector, since there is no beamsplitter that combines the interference and sample light and reflects a portion of the sample light.

While the method of separating illumination and detection path are herein described by an exemplary embodiment of a full field system (FIG. 14), the same method can be applied without restrictions to a partial field system. In the case of a line field system the method can be applied in one dimension, i.e. the non-confocal dimension along the line.

e. Continuous Scanning with Time-Varying Illumination

By separating the illumination and detection paths as described in section "Illumination—Separation of illumination and detection path", one can also vary the illumination pattern during imaging. In a continuous-fast scanning mode, where the partial field is scanned more than one resolution element over the time of a single laser sweep, a time-varying illumination would result in a changing speckle pattern for each frame of acquisition (each wavelength). After processing, the different speckle patterns in each frame would result in speckle reduction of the final volume. Further embodiments of this could include non-continuous wavelength sweeping to further ensure speckle decorrelation of neighboring wavelengths as previously described in U.S. application Ser. No. 14/613,121.

Time-varying illumination of the sample could be achieved by, for instance, allowing the x-y scanners used for scanning of the partial field to vary the angle of the incident light. In physical systems, such a situation may naturally exist due to the impossibility of making perfect optical elements. Other hardware elements such as a DMD, deformable mirror, or SLM placed either in an image-plane or Fourier-plane of the sample may be able to vary the illumination significantly to provide the necessary speckle decorrelation. Depending on the particular implementation, this technique may or may not be compatible with motion correction techniques such as those discussed in Section "Tracking and correction of motion and rotation occurring during acquisition of parallel frequency-domain imaging data" and Hillmann D. et al., "*Common approach for compensation of axial motion artifacts in swept-source OCT and dispersion in Fourier-domain OCT*," Optics Express 2012, which both rely on correlated speckle patterns between multiple wavelengths acquisitions.

f. Variable Optical Power

The optical power of parallel systems or very fast scanning systems can reach very high levels without causing any risk of damaging the retina. However, in the anterior segment of the eye, these systems may create a stationary beam with high power densities. While the cornea and lens can tolerate quite high power levels due to their low absorption in the visible wavelengths up to ~900 nm as well as in the 1060 nm wavelength region, it may not be desirable to expose the iris to beams with very high power densities for an extended amount of time. Especially during alignment, which typically takes significantly longer than the actual acquisition itself, there is a great chance that the beam hits the iris. There are several methods of avoiding the exposure of high power beams to the iris:

Because image quality and acquisition speed can be sacrificed during alignment mode, the system can reduce the optical power during alignment mode. In order to regain some of the sensitivity loss caused by the reduced illumination power, the system can reduce its acquisition speed. This is in particular possible because one often only scans a few B-scans during alignment mode and not entire densely sampled volumes, the reduction in acquisition speed will therefore not be noticeable for the operator.

During the actual data acquisition, which typically only takes a fraction of a second up to 3-4 seconds, the illumination power is then increased to the maximum eye safe exposure. Because the illumination beam can in such a system never illuminate a single spot of the iris for longer than the acquisition time of a single acquisition, the maximum permissible exposure is significantly higher.

In systems with multiple illumination beams, the reduction in illumination power can be realized by only switching all beams on during the actual acquisition, while operating the system with only one or a reduced number of beams during alignment mode.

Information about the location of the beam in the anterior segment of the eye can be used to reduce the power in case the beam hits the iris. This information can for example be obtained by a pupil camera or by analyzing the OCT/holoscopy data (see "Pupil Camera"). Because the OCT/holoscopy scan will lose intensity and eventually vanish as soon the beam is clipped by the iris, this information can be directly used to determine whether all or part of the illumination light is exposed to the iris. Since modern OCT/holoscopy systems provide B-scans at very high repetition rates, the time between light hitting the iris and a reduction in illumination power can be kept very short, resulting in even higher maximum permissible exposures.

Active pupil tracking (US Publication No. 2012/0274897 hereby incorporated by reference) can be used to keep the beam centered in the pupil. In such a system, images of the iris and pupil of the eye are used to control the entry location of the light into the eye.

While each of these methods can be used separately it is beneficial to combine them, because it creates several safety levels and therefore minimizes the risk of damaging the eye, e.g. using high power only during short periods of acquisition in addition to having pupil tracking may be more desirable than using pupil tracking alone.

In systems with a large detection and/or illumination NA, pupil tracking is not only beneficial for eye safety but also to maintain optimum imaging performance, i.e. to avoid clipping of the illumination or detection light by the pupil.

VIII. Reference Signal and Reference Arm Design Related Improvements a. Record Reference Signal at Edge of Detector

Swept source based frequency-domain interferometric imaging is based on the principle that the inverse Fourier transform of the recorded spectral interferogram represents the backscatter profile of the sample as a function of depth. For a correct transformation from the frequency-domain to the spatial domain, the spectral interferogram needs to be sampled linearly in wavenumber, k. Some swept sources used for interferometric imaging methods do not sweep perfectly linearly in k. To compensate for that, one typically either clocks the data acquisition at times corresponding to linear k intervals, or one records in parallel a reference signal which contains information about the sweep's k non-linearity. This information is then later used to resample the acquired data to be spaced linear in wavenumber. The parallel acquisition of a second signal typically adds to the system complexity, because it requires an additional detector and analog to digital converter (ADC).

Figure 15:
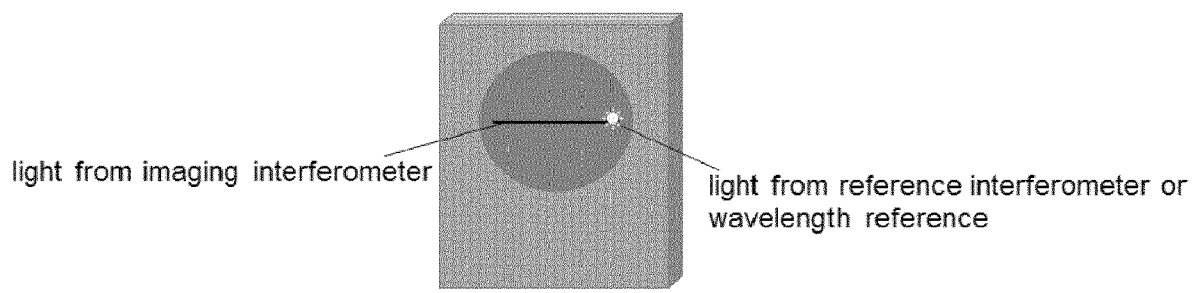
FIG. 15 illustrates an embodiment in which a portion of a 1D detector is used to collect a reference signal while another portion of the detector is used to collect the interference light.

Here we describe a method applicable for swept source based parallel frequency domain imaging systems, which removes the need for a separate detector and ADC. Parallel frequency-domain imaging systems, such as field illumination systems use spatially resolved detectors instead of individual point detectors. A line field system typically uses a 1D detector, full-field systems use 2D detectors and partial field systems use either 1D or 2D detectors. All of these detectors can contain a fairly large number of photosensitive elements. One can therefore easily use one or more of the photosensitive elements for the acquisition of the reference signal without significantly altering the system complexity or efficiency. Ideally one would use one or more photosensitive elements at the edge of the detector as schematically illustrated for a 1D detector in FIG. 15. This helps to avoid any crosstalk between the reference signal and the imaging signal, which is acquired by the other photosensitive elements. For placing the reference signal at that location, one would typically use optics to focus the light on one or a small number of photosensitive elements.

b. Record Source Light at Edge of Detector

The optical power of light sources is, in reality, never completely stable, but exhibits some optical power fluctuations, which we call intensity noise. When this intensity noise is normalized to the average power level, it is called relative intensity noise (RIN). In SS-OCT, the intensity noise represents a significant noise source, which is why one typically takes additional measures, such as dual balancing, to suppress it. The intensity noise is a noise source which is not affected by the optical system. In parallel frequency-domain imaging systems, the RIN is therefore identical in all instantaneous signals from parallel photosensitive elements, and only varies over time. Frequency-domain imaging systems, especially systems for imaging biological tissue, which can only tolerate limited sample power, are designed to have a high optical power from the reference arm shining on the detector, while the light from the sample only accounts for a very small portion of the light incident on the detector. This minimizes the auto-correlation terms created by reflexes in the sample arm. Because the reference intensity is much higher than the intensity of the light returning from the sample, one can assume that the reference light is basically the sole contributor to the overall intensity noise. The two important facts that the RIN is identical on all parallel photosensitive elements at an instantaneous point in time, and that the reference light is the main contributor to the overall RIN, enables the suppression of the RIN by recording the reference light with a detector and subtracting it from the imaging signal.

In point-scanning systems this could be done by tapping the source light from the source or reference arm (for example with a fused coupler), and then digitizing it with a separate detector and analog to digital converter (ADC). One however has to ensure two things; first that the optical path length between this channel and the imaging interferometer is well matched in order to acquire the source light at the same instance in time as the imaging signal; second that the intensity level of the recorded light and the reference light is matched. Matching of the optical path lengths can be done either optically, for example by adjusting the lengths of the fibers, or electronically, for example by introducing a delay in the detection electronics. Matching of the intensities can be done either optically, for example by adjusting the intensity levels by optical attenuators or in post-processing, by normalizing the intensity of the recorded light to the intensity of the reference light of the imaging interferometer prior to the subtraction.

The implementation of this RIN suppression method in parallel frequency-domain imaging systems is significantly simpler. One can here make use of the presence of a large number of photosensitive elements. Instead of tapping of light with the help of an additional fused coupler, one can record the instantaneous reference light by simply blocking the sample light incident on one or more of the photosensitive elements. In order to be able to block the sample light for only one or a few photosensitive elements, without affecting the signal on the other photosensitive elements, one would choose one or more photosensitive elements at the edge of the detector for this purpose. Aside from lower system costs and complexity, this approach has the advantage that the optical path length is inherently matched. If the intensity of the reference light is identical across the detector, one can subtract the signal from the reference photosensitive elements directly from the signals of all the other photosensitive elements. In case the intensity of the reference light varies across the detector, one would first have to normalize the recorded reference intensity to the reference light intensities measured by all the other photosensitive elements prior to each subtraction.

The blocking of the sample light on the reference photosensitive elements at the side can, for example, be achieved by a simple aperture which limits the sample light to a certain region on the detector. In order to assure that only sample light is blocked, the aperture could for example be placed in the sample arm, prior to the beam splitter where the sample light and reference light are combined.

c. Lensless Line Field Reference Arm

In a line field system, one typically focuses the reference light to a line of light on a 1D detector using cylindrical lenses as illustrated in FIG. 2. However, instead of having line forming optics in the reference arm for focusing the reference light on a 1D detector, one can also choose to simply put the fiber tip of a fiber guiding the reference light in front of the detector. This would create a spherical reference wave incident onto the detector. Alternatively, one could use a spherical lens instead of line forming optics in order to collimate the reference light and therefore create a flat wave front incident onto the detector. Both approaches are not very power efficient compared to having a line focus of the reference light on the detector, but significantly simplify the optical design and potentially reduce optical aberrations of the reference light.

IX. Applications a. Fundus Imaging and Enface Imaging

Line-field, partial-field, and full-field interferometric imaging systems can also be used as fundus imaging devices. In fact, a line field interferometric imaging system and a line scanning ophthalmoscope (LSO) are quite similar. Both illuminate the sample, in this case an eye, with a line of light, which is scanned perpendicular to the line. The analogous fundus imaging modality for a partial-field system would be a broad line fundus imager (BLFI) (see for example PCT Publication No. WO 2014/140256) and for a full-field system a fundus camera. Using the frequency-domain imaging system at times also as a fundus imaging device instead of adding a separate dedicated fundus imaging subsystem, has the advantage of reduced system cost and complexity.

Iftimia et al. previously demonstrated a hybrid SD-OCT/LSO device (Iftimia, N.V. et al., Opt. Express 14, 12909, 2006). It combines a SD-OCT system with a LSO by sharing the same camera, but still requires several optical elements in addition to the SD-OCT system in order to bypass the dispersing optics of the spectrometer. Here on the other hand, we describe the use of a swept source based line field system at particular times as a LSO. It does not require any additional components to function as a LSO.

Compared to confocal scanning laser ophthalmoscopes (CSLOs), line and partial field systems provide reduced depth sectioning due to their reduced confocality. In interferometric methods, one can however use the coherence gate to achieve comparable or better depth sectioning capability. In the following text, the concept is described for a line-field holoscopy system in order to maintain simplicity. The same concept can however be applied in a similar fashion to partial- and full-field interferometric frequency-domain imaging systems.

In one embodiment of a line-field holoscopy system (e.g. FIG. 2) one could, during alignment, choose to run the instrument mainly in the LSO mode and interleave one or several line field holoscopy alignment B-scans within each fundus image frame. This can be realized by stopping the wavelength sweep and scanning the line across the sample faster during operation in the LSO mode, and scanning slower or halting the scan across the sample, but starting the wavelength sweep to acquire one or multiple spectral sweeps at each alignment B-scan location. Once the alignment is finished and the operator starts the acquisition of the line field holoscopy volume, the instrument could switch into a line field holoscopy only mode.

In this embodiment, the coherence gate would be defined by the bandwidth of the illumination light, which would in many lasers correspond to the instantaneous line width in case the laser sweep is halted during LSO mode. If one would like to reduce the coherence gate, one could increase the spectral bandwidth of the instantaneous line during LSO mode or choose to use a separate broader light source for this imaging mode. In cases where one would not want a coherence gate at all, one can block the light coming from the reference arm and operate the system in a true non-interferometric LSO mode. If one did not want to add the extra components to enable blocking of the reference arm, one could also adjust the reference arm path length to be different from the sample arm so as to avoid coherent interference, and then optionally use a high pass filter on the signal. The high pass filter would remove the constant light from the reference arm, resulting in an image generated from the varying light returning from the sample without DC offset.

Using the holoscopy system in an interferometric LSO mode is advantageous over conventional, non-interferometric LSO's because one can benefit of the depth sectioning capability provided by the limited coherence length of the light source and gain access to the phase and therefore apply holoscopic focusing and aberration correction techniques. In order to gain access to the phase in cases where one chooses to acquire only one spectral sample per transverse location on the sample, one has to generate a carrier frequency. This carrier frequency can be generated by optical modulators, Doppler shifting the reference and/or sample light or use an off-axis configuration, which generates a carrier frequency across the detector (for more details on off-axis configurations please also refer to section "partial field frequency-domain interferometric imaging"). An off-axis configuration in such a time domain interferometric system however creates a tilt of the coherence plane in the sample proportional to the off-axis angle. To avoid this one can use a grating to generate the off-axis angle. This generates a tilt of the coherence plane of the reference wave, in contrast to the wavefront, which is always perpendicular to the propagation direction of the wave (Maznev, A. A. et al., Opt. Lett. 23, 1378, 1998). Liu et al. recently demonstrated an off-axis line field confocal microscope, however did not recognize that a source with a reduced coherence length could provide the additional depth section capability necessary for successfully applying holoscopic reconstructions and computational adaptive optics methods in thick scattering samples (Liu, C. et al., Opt. Express 22, 17830-9, 2014).

Figure 19:
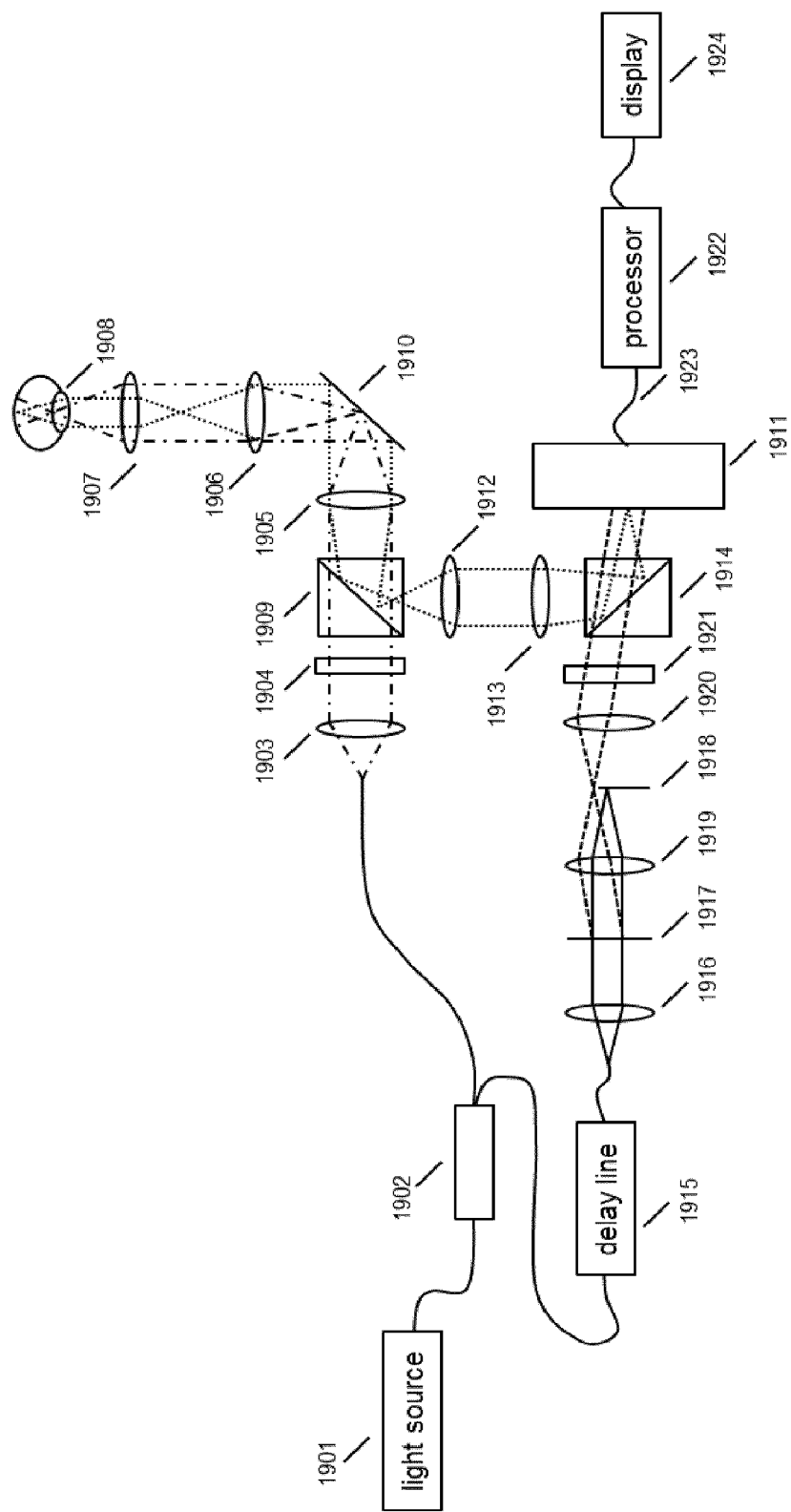
FIG. 19 illustrates one embodiment of an off-axis line field holoscopy system, which can also be used as a line scan ophthalmoscope with computational adaptive optics capabilities.

An off-axis line field holoscopy system, which can also be used as an interferometric LSO with computational adaptive optics capabilities is schematically illustrated in FIG. 19. Light from a light source 1901 is split by a fiber coupler 1902 into sample and reference light. In cases where the device is intended to be used as a enface/fundus imaging device as well as a tomographic imaging device, light source 1901 would be a swept source. In cases where the device is only intended to be used as a enface/fundus imaging device, one can replace the swept source by any at least partially coherent light source. The light source could be a swept laser or another at least partially coherence light source. The sample light (on the illumination path indicated by a dashed-dotted line) is collimated by a fiber collimator 1903 and then focused to a line by a cylindrical lens 1904. The line is relayed to the retina by spherical lenses 1905, 1906, and 1907 and the optics of the eye 1908. Although the system is here described as a system for imaging the retina, it can be modified to image any light scattering sample. On the way to the sample the light passes a beam splitter 1909 in transmission mode. In order to obtain an enface or fundus image the line of light is scanned by a scanner 1910. The detection light path of the light backscattered from the retina is illustrated by the dotted lines. A point on the retina is imaged to the detector 1911 by the optics of the eye 1908 and spherical lenses 1907, 1906, 1905, 1912, and 1913. Before it reaches the detector 1911, it is descanned by the scanner 1910, reflected by the beamsplitter 1909 and combined with the reference light by beamsplitter 1914. The reference light first passes a delay line 1915 and is then collimated by a fiber collimator 1916. In order to generate an off-axis angle between reference and sample light, the reference light passes a transmission grating 1917. To block the zero order beam (solid lines) by a beam block 1918 and only let the first order beam (dashed line) pass, the reference light passes a telescope consisting out of 2 spherical lenses 1919 and 1920. A cylindrical lens 1921 then focuses the light onto the detector 1911. Before it reaches the detector, the reference light passes the beamsplitter 1914 where reference and sample light are recombined. The delay line 1915 is typically adjusted so that sample and reference light travel close to the same optical distance. If this is the case, sample and reference light coherently interfere on the detector 1911.

The electrical signals from the detector 1911 are transferred to the processor 1922 via a cable 1923. The processor 1922 may for example contain a field-programmable gate array (FPGA), a digital signal processor (DSP), an application specific integrated circuit (ASIC), a graphic processing unit (GPU), a system on chip (SoC) or a combination thereof, which performs some, or the entire signal processing steps, prior to passing the data on to the host processor. The processor 1922 generates image data of the object from the detected signals. This could be an enface image, a fundus image or a 3D representation of the retina. The processor can be operably attached to a display 1924 for displaying images of the data. The sample and reference arms in the interferometer could consist of bulk-optics, photonic integrated circuits, fiber-optics or hybrid bulk-optic systems and could have different architectures such as Michelson, Mach-Zehnder or common-path based designs as would be known by those skilled in the art. While a transmissive delay line is shown in FIG. 4, those skilled in the art would appreciate that a reflective delay line could also be used. Cable 1923 could be replaced with a wireless data transmission.

One can choose not to stop the wavelength sweep during the times of LSO mode operation. In this case switching between modes only involves operating the scanner at different speeds. Again, faster for the LSO mode and slower or stopped for the line field holoscopy mode. The advantage of this implementation is that it allows using lasers which cannot easily switch between a static output wavelength and a wavelength sweep. A drawback is that each line of the LSO fundus image is acquired with a different wavelength band, which may alter the look of the fundus image. A related imaging mode for swept source based point-scanning systems was described in US Patent Publication No. 2013/0301000 hereby incorporated by reference.

In another embodiment, one can increase the sweep speed during the enface imaging mode. It can be increased up to the extent that the time of one sweep is equal to the time of one detector exposure. In this particular case, one can acquire a single enface image with a coherence gate which is defined by the total spectral sweep range. This allows tuning of the coherence gate with lasers which are not able to easily adjust the coherence length of the instantaneous line. The broader the spectral sweep during one exposure time is, the shorter is the coherence gate.

In order to obtain multiple enface images at different depths, one can adjust the sweep speed to cover several detector exposures. Such a mode corresponds to a shallow depth interferometric Fourier domain imaging mode, where the coherence gate is again defined by the total spectral sweep range of the sweep, while the number of enface planes is defined by the spectral resolution of the acquisition (i.e. the number of detector exposures per sweep).

Since the coherence gate, unlike the confocal gate, is independent of the NA of the imaging system, this method provides a convenient way of adjusting the depth sectioning without any mechanical changes to the system. The full adjustment can instead be done electronically as described above by adjusting the instantaneous line width, the spectral sweep range of the laser and/or the scan speed. Variable depth sectioning may be especially desirable for alignment purposes, because an image is only obtained if the path length difference between sample and reference arm is smaller than the coherence length. It is therefore helpful to start the alignment with a longer coherence length, i.e. larger coherence gate, and then dial it down after the path length mismatch between reference and sample arm has been properly adjusted. This can also be implemented as an iterative process, where the path length mismatch and coherence length are adjusted in an alternating fashion.

Above we described the fundus imaging mode to be an alignment aid for the tomographic imaging mode. This relationship can however be reversed, where a tomographic mode is used as alignment mode for a coherence gated enface imaging modality. One could even envision an alignment mode where the user can pick a specific layer in a tomogram and the instrument then automatically sets the path length difference between the reference and sample arms, and potentially also the coherence gate, accordingly in order to acquire a high resolution enface image of the particular layer of choice.

While mechanically tuned lasers are typically limited in their flexibility of quickly varying parameters such as sweep speed, sweep range and coherence length of the instantaneous line, akinetic lasers, such as for example SG-DBR lasers, are typically well suited for these adjustments.

The above described interferometric fundus imaging method can be further improved when used in conjunction with the sub-aperture based aberration measurement and correction technique (see for example US Patent Publication No. 2014/0218684 hereby incorporated by reference). This combination would allow to numerically focus the fundus image after the image was already acquired and even correct for higher order aberrations introduced by imperfections of the human eye and the system's optics. Such a corrected image would then resemble a fundus image acquired with an adaptive optics fundus imaging system.

For all of the above described enface imaging embodiments, an imaging relationship between the sample and the detector is not necessarily required. In case a defocused image or an image in the far field is acquired, the acquired image can be numerically propagated to an image plane and/or a 2D FFT can be used to transform the acquired image from the frequency domain to the spatial domain.

The above described systems and methods can also be used for enface imaging and shallow depth imaging of other technical and biological samples outside the human eye. They could further be used for other applications, such as profilometry, phase microscopy and dispersion contrast imaging of technical and biological samples (Choma, M. A. et al., Opt. Lett. 30, 1162, 2005; Sarunic, M. V. et al., Opt. Lett. 31, 1462, 2006; Endo, T. et al., Opt. Express 13, 695, 2005; Grajciar, B. et al., Opt. Express 18, 21841-50, 2010; Grajciar, B. et al., Photonics Lett. Pol. 3, 2011).

b. Directional Scattering

Parallel holoscopy techniques involve detecting backscattered photons with a spatially resolved detector. One is therefore able to split the pupil in multiple sub-apertures, as described by Kumar et al. (Kumar, A. et al., Opt. Express 21, 10850-66, 2013) and in US Patent Publication No. 2014/0218684, either by imaging the pupil directly or by Fourier transforming the spatial image data numerically to access the spatial frequency space. Each sub-aperture then contains light backscattered under a different angle. One can therefore reconstruct multiple images or volumes, with lower lateral resolution, but different angular information. The gained angle dependent information can be of help for several applications as will be described in further detail below.

In single-point-scanning systems the pupil can as well be split computationally as described by Kumar et al. (Kumar, A. et al., Opt. Express 21, 10850-66, 2013) and in US Patent Publication No. 2014/0218684 hereby incorporated by reference, by first acquiring a volume and then applying the computational pupil splitting on the entire volume or a subvolume thereof. This method enables most directional scattering methods described in the following subsections. Since a single-point-scanning system however samples different spatial locations of the sample at different points in time, it lacks the ability to provide instantaneous directional scattering information as would be required for example for the application of absolute blood flow measurements described under "Absolute angle resolved velocity measurements".

The pupil can however also be split optically for example by the use of a pyramid mirror, which splits the detection beam into several sub beams, each containing light from different portions of the pupil and therefore light scattered at different angles. In one embodiment one uses a pyramid with a trilateral base to split the detection beam (after sample and reference light coherently interfered) into three subbeams. The three subbeams can then be collected using three separate fiber collimators. Since each of the three channels contains different angle dependent scattering information from a common sample location, the information can be used for holoscopic reconstructions as well as to enable the applications described in the following subsections.

c. Tissue Specific Directional Scattering

Some samples exhibit non-uniform scattering characteristics. In biological samples, the orientation of fibers may cause the light to scatter more in one direction than in another direction. Such a behavior is for example observable when imaging the human retina with OCT, where the Henle fibers are only visible if the light is detected from a certain angle (see for example US Patent Publication No. 2012/0274897 hereby incorporated by reference).

With a holoscopy system, one can numerically split the pupil in multiple sub-apertures as previously described. By reconstructing images from each of the sub-apertures individually, one is able to create separate images, which were created only by light backscattered under a corresponding angle. The scattering characteristics captured by these multiple images can then be used either to identify particular structures or tissue types within the sample, or to characterize these structures or tissue types. For instance one could characterize the nerve fiber layer health in the eye by how directional the scattering from this tissue layer is.

d. Dark Field Imaging

Optical systems, especially non-confocal systems, often suffer from specular reflexes from optical surfaces. For example in fundus cameras, a lot of care is taken to avoid reflexes from the cornea, or in microscopy, specific dark field microscopes are used, which only detect scattered light and block any reflections from the cover plate or the surface of the sample. Such dark field systems often also exhibit different contrast, which may provide additional information.

A holoscopy system can very easily be transformed to a dark field holoscopy system, without the need for additional physical aperture stops. In a system, where the pupil is imaged to the detector, it can be implemented the easiest, by simply setting the central photosensitive elements of the detector which detect only reflected light or light scattered at very low angles, to zero. In a holoscopy system where the detector is placed at a position corresponding to a conjugate plane of the sample, one first needs to Fourier transform the acquired frame from the spatial domain to the spatial frequency domain, in order to similarly filter the reflected light.

e. Absolute Angle Resolved Velocity Measurements

Doppler OCT velocity measurements are used to measure the blood flow inside vessels of the human retina because changes in the blood flow are believed to be an early indicator for several diseases (Leitgeb, R. et al., Opt. Express 11, 3116-21, 2003; Schmoll, T. et al., Opt. Express 17, 4166, 2009). By calculating the phase difference between successive measurements separated in time, one is able to calculate the axial velocity of a moving scatterer (e.g. a red blood cell (RBC)) (Leitgeb, R. A. et al., Opt. Lett. 29, 171, 2004). In order to determine the absolute velocity, one however also has to have knowledge about the angle between the detection axis and the scatterer's velocity vector:

$$v_{abs} = v_{axial}/\cos(\alpha) = \Delta\Phi/(2nkT\cos(\alpha)),$$

with n, being the refractive index, k, the central wavenumber, $\alpha$, the angle between the velocity vector and the detection axis, and T, the time difference between the two measurements. Gaining information about $\alpha$ is generally not very easy and often inaccurate, because volumetric data or several temporally separated cross-sections have to be acquired for further processing. This typically involves computationally expensive image processing techniques in order to extract the angle of a vessel in the human eye. For point scanning systems, it was therefore proposed to use at least two beams with different angles (Werkmeister, R. M. et al., Opt. Lett. 33, 2967, 2008; Pedersen, C. J. et al., Opt.

Lett. 32, 506, 2007; Iftimia, N. V. et al., Opt. Express 16, 13624, 2008), which then allow to calculate the absolute velocity independent of a:

$$v_{abs}=(v'_{axial}-v''_{axial})/(\Delta\gamma \cos(\Delta\beta))=(\Delta\Phi'-\Delta\Phi'')/(2nkT\Delta\gamma \cos(\Delta\beta))$$

with $\Delta\gamma$, being the separation angle between the two beams, $\Delta\beta$, the angle between the illumination plane subtended by the two beams and the scatterer's velocity vector. $v'_{axial}$, and $v''_{axial}$, are the axial velocities along the two beams calculated from the respective phase differences, $\Delta\Phi'-\Delta\Phi''$. One can recognize that it is possible to lose the dependency on a, but then knowledge about the angle, $\Delta\beta$, is required. $\Delta\beta$ is however typically easily measureable, e.g. in a fundus image. Since $\cos(\Delta\beta)$ becomes very small for angles close to 90 deg, this method only works for fairly low $\Delta\beta$.

Trasischker et al. recently introduced a method using 3 beams in order to measure absolute velocities without requiring any prior knowledge about the scatterer's traveling direction (Trasischker, W. et al., J. Biomed. Opt. 18, 116010, 2013; Haindl, R. et al., Biomedical Optics BT3A.74, 2014; Haindl, R. et al., J. Mod. Opt. 1-8, 2014). The three beams form an equilateral triangle-based pyramid, with the tip of the beam being the mutual focal spot and the base of the pyramid being the pupil plane. By knowing the distance between the beams in the pupil plane, and the distance from the pupil plane to the image plane, one is able to determine the exact spatial orientation of the three measurement beams (vectors ($e_x$, $e_y$, $e_z$)). One then ends up with a system of three equations with three unknown variables, $v_x$, $v_y$ and $v_z$:

$$v'_{axial}=e'_x v_x + e'_y v_y + e'_z v_z$$

$$v''_{axial}=e''_x v_x + e''_y v_y + e''_z v_z$$

$$v'''_{axial}=e'''_x v_x + e'''_y v_y + e'''_z v_z$$

A related approach can be implemented more simply with a holoscopy system as described herein by numerically splitting the pupil into three sub-apertures. These sub-apertures can then be treated as individual imaging beams and processed in a similar fashion as described above in order to obtain an absolute velocity vector, ($v_x$, $v_y$, $v_z$), which contains information about the velocity as well as the direction of the moving scatterer. Likewise, the two beam method described earlier can be accomplished by splitting the collection pupil into two sub-apertures. Absolute velocity vectors can also be calculated from pupils that have been split into more than three sub-apertures, where the additional sub-apertures give additional measures of the velocity, allowing an estimate of the accuracy of the measurement.

Another simpler implementation of the above described multidirectional multi-beam Doppler systems, which use multiple illumination and detection beams, is to illuminate with a single beam and then split the pupil optically for example by a pyramid mirror as described in "Directional scattering". This significantly simplifies the interferometer design, avoids difficulties with cross-talk and misalignment of the illumination spots on the sample.

The herein described method of computational pupil splitting can similarly be applied to bidirectional Doppler measurements, where the vessel cross-section within B-scans are evaluated to directly determine the absolute flow as described in US Patent Publication No. 2015/0092195 hereby incorporated by reference and (Blatter, C. et al., Opt. Lett. 38, 4433-6, 2013).

f. Stereoscopic Viewing

For some applications, like for example surgical microscopy, depth perception is an important factor when viewing image or volume data. With a holoscopic system, one can create stereoscopic images by splitting the pupil and reconstructing separate images for each of the viewer's eyes. For this purpose the pupil would be split in two sub-apertures. The two sub-apertures can each cover 50% of the pupil's total area. One may however also choose to use two sub-apertures which each cover less than 50% of the pupil's total area in the pupil, in order to reduce the numerical aperture. The dimension in which the pupil would be split (for example horizontally or vertically) would ideally correspond to the orientation of which the volume is viewed. The two separate images can then be assigned accordingly to the user's left and right eyes. As the full 3D directional scattering information is available in the data set, one can also provide great flexibility in viewing the data set, with possible adjustable viewing parameters including: parallax, depth of field, focal depth, gamma, tissue transparency, and magnification.

g. Functional Imaging

Currently, retinal diseases are only treated after pathological changes and loss of vision have already occurred. It is believed that probing retinal function in vivo, in a non-invasive way, could in the future provide a method for detecting ophthalmological diseases at a very early stage, even before pathological changes are detectable with current diagnostic tools. Several research groups have proposed methods where reflectivity changes of retinal tissue due to flash or flicker stimuli are detected (Tsunoda, K. et al., Invest. Ophthalmol. Vis. Sci. 45, 3820-6, 2004; Abramoff, M. D. et al., Invest. Ophthalmol. Vis. Sci. 47, 715-21, 2006; Bizheva, K. et al., Proc. Natl. Acad. Sci. U.S.A. 103, 5066-71, 2006; Sharon, D. et al., Cereb. Cortex 17, 2866-77, 2007; Hanazono, G. et al., Invest. Ophthalmol. Vis. Sci. 48, 2903-2912, 2007; Jonnal, R. S. et al., Opt. Express 15, 16141-16160, 2007; Inomata, K. et al., Invest. Ophthalmol. Vis. Sci. 49, 2193-2200, 2008; Machida, S. et al., Invest. Ophthalmol. Vis. Sci. 49, 2201-2207, 2008; Grieve, K. et al., Invest. Ophthalmol. Vis. Sci. 49, 713-719, 2008; Srinivasan, V. J. et al., Opt. Express 17, 3861, 2009; Schmoll, T. et al., J. Biomed. Opt. 15, 041513, 2010). In vivo studies of reflectivity changes in the human retina are however challenging due to various sources of error, such as eye motion and the presence of speckle. Especially point scanning systems where image points are not only separated spatially but also temporally, may suffer severely from motion artifacts (Schmoll, T. et al., J. Biomed. Opt. 15, 041513, 2010). With parallel frequency-domain imaging systems, one can make use of the simultaneous detection of spatially separated image points; for example by placing the instantaneous FOV in a way that it covers the stimulated and unstimulated area in one acquisition.

Phase sensitive detection may provide a way to increase the sensitivity of functional imaging approaches (Schmoll, T. et al., J. Biomed. Opt. 15, 041513, 2010). Holoscopy, being an interferometric method, provides easy access to the phase. Parallel holoscopy systems have the additional distinct advantage that they are inherently phase stable across the instantaneous FOV. By placing the FOV across a stimulated and unstimulated area simultaneously, one would be able to detect very small phase changes of the light backscattered from the stimulated area relative to unstimulated regions.

h. Angiography

OCT angiography is used to contrast the capillaries in the human retina in-vivo. In OCT Angiography, measurements are repeated at approximately the same transverse locations on the sample separated in time. Changes in the amplitude and/or phase of the repeated measurements can be determined and used to highlight motion, such as blood flow within vessels. There are multiple OCT Angiography data processing techniques that utilize inter-frame or intra-frame change analyses of the intensity, speckle, phase-resolved, or complex OCT data. One of the major applications of such techniques has been to generate enface vasculature images of the retina. Enface images are typically generated from three dimensional data cubes by summing pixels along a given direction in the cube, either in their entirety or from sub-portions of the data volume. Visualization of the detailed vasculature using functional OCT enables clinicians to obtain new and useful clinical information for diagnosis and management of eye diseases in a non-invasive manner. Any of the partial field systems and approaches described herein could be used to collect image data suitable for motion contrast analysis.

While OCT is able to produce very nice images of the capillary beds in the inner retina, it seems still to be challenging to contrast the network of the choriocapillaris. Its capillaries are only a few micrometers in diameter and are very densely packed. Resolving these capillaries therefore requires high resolution. Holoscopy in combination with its computational adaptive optics capabilities can provide the required resolution and thus enhance the quality of choriocapillaris images. Because the flow rates in the choriocapillaris are also typically higher than in the capillaries of the inner retina, the image quality can profit further from the very high frame rate of parallel holoscopy methods.

The superior motion correction capability of partial field systems, as described in the section "Motion correction", over other interferometric imaging modalities is also advantageous for contrasting moving scatterers with partial field systems.

i. Polarization Sensitive Holoscopy

Polarization-sensitive OCT has been demonstrated to provide additional contrast in biological and technical samples (Götzinger, E. et al., Opt. Express 13, 10217, 2005; Stifter, D. et al., Opt. Express 18, 25712-25, 2010; Everett, M. J. et al., Opt. Lett. 23, 228, 1998; Moreau, J. et al., Appl. Opt. 42, 3811, 2003; Schmoll, T. et al., Opt. Lett. 35, 241-3, 2010). Although fiber based polarization sensitive OCT systems have been presented in the past, it is generally easier to implement a polarization sensitive system using bulk polarization sensitive optics (Gotzinger, E. et al., Opt. Express 17, 22704-17, 2009). The interferometer of a parallel holoscopy system often consists of bulk optics and is therefore ideally suited for polarization sensitive holoscopy implementations.

Implementing polarization-sensitive OCT typically often requires multiple separate detection systems. Using only a small ROI on the 2D sensor lends itself to the possibility of splitting the detection light to illuminate multiple small patches on the 2D sensor simultaneously. Each patch would then correspond to a polarization-sensitive state and, together, would allow for polarization-sensitive measurements. The use of a single detector could allow for a less expensive setup. This same approach would also be compatible for setups as described in section "Scanning Related Improvements—Use of DMD in parallel frequency-domain imaging" and "Scanning Related Improvements—Scanning with a single MEMS mirror" where the detection area is scanned along the 2D sensor. In this situation, all the separate polarization-sensitive patches on the camera would move together. The only modification required would be a slightly larger 2D sensor corresponding to the union of the maximum FOVs for each of the polarization-sensitive patches.

In an alternative embodiment the different polarization states can be multiplexed in the spatial frequency domain. Off-axis systems have the advantage of suppression of the mirror image, as well as DC and auto-correlation terms. This however comes at the cost of poor usage of the spatial frequency space. In fact, off-axis systems commonly only use one quadrant of the spatial frequency space, which directly correlates to an inefficient use of the detectors photosensitive elements. The unused spatial frequency space can however be utilized to encode for example signals from an additional orthogonal polarization state. To do so one uses two reference arms with linear orthogonal polarization states and different off-axis angles. The off-axis angles should be chosen to separate the corresponding cross-correlation terms in the spatial frequency terms from each other as well as the auto-correlation and DC terms. This doubles the used spatial frequency space and hence makes better use of the photosensitive elements of the detector. It however comes at the cost of dynamic range on the detector, because it has to be divided among the two reference arms. This can however be neglected as long as each reference arm generates sufficient shot noise to overcome the detector noise limit and sufficient digitization depth is available in order to not be limited by quantization noise. While the spatial frequency multiplexing was described herein as a way to encode polarization diverse information in the spatial frequency space, this method can also be used to encode other additional information in the spatial frequency space. For example interference signals from a different depth, by having the pathlength of the second reference arm offset from the first reference arm. A related approach for polarization sensitive point-scanning OCT was presented by Schmoll et al. (Schmoll, T. et al., Opt. Lett. 35, 241-3, 2010). Point-scanning systems however cannot be operated in an off-axis configuration, which is why they had to use a phase modulator in at least one of the reference arms in order to introduce a carrier frequency, which separates one of the polarization states from the other.

The invention claimed is:

1. An optical coherence tomography (OCT) device, comprising:
    a light source configured for generating a beam of light;
    a beam divider configured for directing a first portion of the beam of light into a reference arm and a second portion of the beam of light into a sample arm;
    a first scanner configured for receiving the second portion of the beam of light and configured for providing scanning along a first linear direction;
    a second scanner configured for receiving a first output from the first scanner and configured for providing scanning along a second linear direction at an acute angle to the first linear direction,
    wherein the first scanner and the second scanner have substantially the same scan speed;

optics configured for directing a second output from the second scanner to one or more locations on a sample;

a detector configured for receiving light returning from the sample and the first portion of the beam of light from the reference arm and generating signals in response thereto; and a processor configured for converting the signals into image data.

2. The device of claim 1, wherein the first linear direction is at 45 degrees to the second linear direction.

3. The device of claim 1, wherein the first scanner and the second scanner produce a scan beam having a substantially linear scan path on the sample.

\* \* \* \* \*